(12) United States Patent
Charlesworth et al.

(10) Patent No.: US 12,186,547 B2
(45) Date of Patent: Jan. 7, 2025

(54) PERIPHERAL NERVE STIMULATION FOR RESTLESS LEGS SYNDROME

(71) Applicant: Noctrix Health, Inc., San Francisco, CA (US)

(72) Inventors: Jonathan David Charlesworth, San Francisco, CA (US); Shriram Raghunathan, Castro Valley, CA (US)

(73) Assignee: NOCTRIX HEALTH, INC., Pleasanton, CA (US)

( * ) Notice: Subject to any disclaimer, the term of this patent is extended or adjusted under 35 U.S.C. 154(b) by 480 days.

(21) Appl. No.: 17/389,551

(22) Filed: Jul. 30, 2021

(65) Prior Publication Data
US 2022/0088372 A1    Mar. 24, 2022

Related U.S. Application Data

(63) Continuation of application No. 17/062,010, filed on Oct. 2, 2020, now Pat. No. 11,103,691.
(Continued)

(51) Int. Cl.
*A61N 1/04*    (2006.01)

(52) U.S. Cl.
CPC ......... *A61N 1/0452* (2013.01); *A61N 1/0456* (2013.01); *A61N 1/0492* (2013.01)

(58) Field of Classification Search
CPC ... A61N 1/0452; A61N 1/0456; A61N 1/0492
See application file for complete search history.

(56) References Cited

U.S. PATENT DOCUMENTS

| | | |
|---|---|---|
| 5,487,759 A | 1/1996 | Bastyr et al. |
| 5,725,471 A | 3/1998 | Davey et al. |

(Continued)

FOREIGN PATENT DOCUMENTS

| | | |
|---|---|---|
| CN | 110603073 | 12/2019 |
| CN | 115087482 | 9/2022 |

(Continued)

OTHER PUBLICATIONS

"International Application Serial No. PCT US2018 012631, Invitation to Pay Add'l Fees and Partial Search Report mailed Mar. 27, 2018", 2 pgs.
(Continued)

*Primary Examiner* — Amanda K Hulbert
*Assistant Examiner* — Philip C Edwards
(74) *Attorney, Agent, or Firm* — SCHWEGMAN LUNDBERG & WOESSNER, P.A.

(57) ABSTRACT

Systems and methods for treating a patient having symptoms of restless legs syndrome (RLS) or Periodic Limb Movement Disorder (PLMD) using high-frequency stimulation by applying a high-frequency pulsed electrostimulation therapy signal to a peroneal nerve or a branch thereof, where the therapy signal is above a motor threshold of a muscle innervated by the peroneal nerve or branch thereof. Surface EMG (sEMG) response to neurostimulation can be used to evaluate patient responsivity to neurostimulation, or to evaluate neurostimulation efficacy, such as to compare various neurostimulation parameter settings and to select between such settings to meet or balance between one or more goals. The sEMG response can be obtained with the muscle at rest, or during muscle activation.

22 Claims, 17 Drawing Sheets

Related U.S. Application Data

(60) Provisional application No. 62/706,525, filed on Aug. 22, 2020, provisional application No. 62/910,241, filed on Oct. 3, 2019.

(56) References Cited

U.S. PATENT DOCUMENTS

| | | | |
|---|---|---|---|
| 5,759,198 | A | 6/1998 | Karell |
| 5,995,873 | A | 11/1999 | Rhodes |
| 6,001,861 | A | 12/1999 | Oertel et al. |
| 6,114,326 | A | 9/2000 | Schueler |
| 6,507,757 | B1 | 1/2003 | Swain |
| 6,602,868 | B2 | 8/2003 | McBrinn et al. |
| 6,958,048 | B2 | 10/2005 | Bonutti |
| 7,403,821 | B2 | 7/2008 | Haugland et al. |
| 7,774,068 | B1 | 8/2010 | Lozano |
| 7,783,348 | B2 | 8/2010 | Gill et al. |
| 8,145,317 | B2 | 3/2012 | Demarais et al. |
| 8,365,741 | B2 | 2/2013 | Hennings et al. |
| 8,938,303 | B1 | 1/2015 | Matsen |
| 8,983,617 | B2 | 3/2015 | Chavan et al. |
| 9,002,477 | B2 | 4/2015 | Burnett |
| 9,017,273 | B2 | 4/2015 | Burbank et al. |
| 9,205,264 | B2 | 12/2015 | Heruth et al. |
| 9,302,046 | B1 | 4/2016 | Giuffrida et al. |
| 9,327,121 | B2 | 5/2016 | Thacker et al. |
| 9,387,338 | B2 | 7/2016 | Burnett |
| 9,452,287 | B2 | 9/2016 | Rosenbluth et al. |
| 9,474,898 | B2 | 10/2016 | Gozani et al. |
| 9,504,827 | B2 | 11/2016 | DeGiorgio et al. |
| 9,561,371 | B2 | 2/2017 | Elborno |
| 9,566,470 | B2 | 2/2017 | Malizia |
| 9,604,056 | B2 | 3/2017 | Starr et al. |
| 9,610,448 | B2 | 4/2017 | Hou et al. |
| 9,656,070 | B2 | 5/2017 | Gozani et al. |
| 9,662,491 | B2 | 5/2017 | Yonce et al. |
| 9,662,502 | B2 | 5/2017 | Giuffrida et al. |
| 9,694,181 | B2 | 7/2017 | Bhadra et al. |
| 9,713,711 | B2 | 7/2017 | Hershey et al. |
| 9,737,709 | B2 | 8/2017 | Bachinski et al. |
| 9,750,933 | B2 | 9/2017 | Gregory et al. |
| 9,802,039 | B2 | 10/2017 | Palermo et al. |
| 9,802,041 | B2 | 10/2017 | Wong et al. |
| 9,808,620 | B2 | 11/2017 | Kent |
| 9,808,627 | B2 | 11/2017 | Gliner et al. |
| 9,814,880 | B2 | 11/2017 | Hershey et al. |
| 10,195,425 | B2 | 2/2019 | Ostroff et al. |
| 10,342,977 | B2 | 7/2019 | Raghunathan |
| 11,103,691 | B2 | 8/2021 | Charlesworth et al. |
| 11,266,836 | B2 | 3/2022 | Charlesworth et al. |
| 2003/0176822 | A1 | 9/2003 | Morgenlander |
| 2004/0093093 | A1 | 5/2004 | Andrews |
| 2006/0069415 | A1 | 3/2006 | Cameron et al. |
| 2006/0173074 | A1 | 8/2006 | Ellmen et al. |
| 2008/0262053 | A1 | 10/2008 | Reess |
| 2009/0062685 | A1 | 3/2009 | Bergethon et al. |
| 2009/0221943 | A1 | 9/2009 | Burbank et al. |
| 2010/0049111 | A1 | 2/2010 | Sorg |
| 2010/0160712 | A1 | 6/2010 | Burnett et al. |
| 2010/0191311 | A1 | 7/2010 | Scheiner et al. |
| 2010/0249637 | A1 | 9/2010 | Walter et al. |
| 2011/0054573 | A1 | 3/2011 | Mitchell |
| 2012/0101358 | A1 | 4/2012 | Boettcher et al. |
| 2013/0245486 | A1 | 9/2013 | Simon et al. |
| 2013/0325084 | A1 | 12/2013 | Lee |
| 2014/0046423 | A1 | 2/2014 | Rajguru et al. |
| 2014/0148725 | A1* | 5/2014 | Cadwell ............... A61B 5/296 600/546 |
| 2014/0277220 | A1 | 9/2014 | Brennan et al. |
| 2015/0066105 | A1 | 3/2015 | Elborno |
| 2015/0165202 | A1 | 6/2015 | Grandhe |
| 2015/0174002 | A1 | 6/2015 | Burbank et al. |
| 2015/0272815 | A1 | 10/2015 | Kitchens |
| 2015/0321000 | A1 | 11/2015 | Rosenbluth et al. |
| 2016/0030280 | A1 | 2/2016 | Jones |
| 2016/0106344 | A1* | 4/2016 | Nazari ............... A61B 5/6828 600/595 |
| 2016/0158542 | A1 | 6/2016 | Ahmed |
| 2016/0310741 | A1 | 10/2016 | Baru et al. |
| 2016/0354604 | A1 | 12/2016 | Kent |
| 2017/0157398 | A1 | 6/2017 | Wong et al. |
| 2017/0157404 | A1 | 6/2017 | Moffitt et al. |
| 2017/0216586 | A1 | 8/2017 | Kent |
| 2017/0266443 | A1 | 9/2017 | Rajguru et al. |
| 2018/0098046 | A1 | 4/2018 | Husak et al. |
| 2019/0001129 | A1* | 1/2019 | Rosenbluth ............... A61N 1/08 |
| 2019/0083784 | A1 | 3/2019 | Raghunathan |
| 2020/0108251 | A1 | 4/2020 | Raghunathan |
| 2021/0100998 | A1 | 4/2021 | Charlesworth et al. |
| 2021/0260379 | A1 | 8/2021 | Charlesworth et al. |
| 2022/0143393 | A1 | 5/2022 | Charlesworth et al. |
| 2022/0218993 | A1 | 7/2022 | Charlesworth et al. |

FOREIGN PATENT DOCUMENTS

| | | |
|---|---|---|
| JP | 2010246745 A | 11/2010 |
| JP | 2017503537 A | 2/2017 |
| JP | 2017524396 A | 8/2017 |
| JP | 2020505099 | 2/2020 |
| JP | 2022551604 | 12/2022 |
| WO | 2015109023 | 7/2015 |
| WO | 2017023864 | 2/2017 |
| WO | 2018129351 | 7/2018 |
| WO | 2021067751 | 4/2021 |

OTHER PUBLICATIONS

"International Application Serial No. PCT US2018 012631, International Search Report mailed May 30, 2018", 5 pgs.

"International Application Serial No. PCT US2018 012631, Written Opinion mailed May 30, 2018", 8 pgs.

"U.S. Appl. No. 16/196,863, Notice of Allowance mailed Feb. 20, 2019", 8 pgs.

"International Application Serial No. PCT US2018 012631, International Preliminary Report on Patentability mailed Jul. 18, 2019", 10 pgs.

"Chinese Application Serial No. 201880012637.9, Notification to Make Rectification mailed Sep. 10, 2019", w o English Translation, 1 pg.

"U.S. Appl. No. 16/416,330, Preliminary Amendment filed Dec. 26, 2019", 8 pgs.

"European Application Serial No. 18736570.5, Extended European Search Report mailed Sep. 30, 2020", 7 pgs.

"International Application Serial No. PCT US2020 054006, International Search Report mailed Dec. 21, 2020", 7 pgs.

"International Application Serial No. PCT US2020 054006, Written Opinion mailed Dec. 21, 2020", 8 pgs.

"U.S. Appl. No. 17/062,010, Non Final Office Action mailed Jan. 7, 2021", 11 pgs.

"Personalized medicine", https: web.archive.org web 20190417064230 https: www.nature.com subjectspersonalized-medicine, (Apr. 17, 2019), 5 pgs.

"National Institutes of Health", https: web.archive.org web 20190829044030 https: allofus.nih.gov , (Aug. 29, 2019), 6 pgs.

"U.S. Appl. No. 17/062,010, Response filed Apr. 7, 2021 to Non Final Office Action mailed Jan. 7, 2021", 14 pgs.

"U.S. Appl. No. 16/416,330, Non Final Office Action mailed Apr. 14, 2021", 7 pgs.

"U.S. Appl. No. 17/062,010, Notice of Allowance mailed Apr. 23, 2021", 5 pgs.

"U.S. Appl. No. 17/062,010, PTO Response to Rule 312 Communication mailed May 20, 2021", 2 pgs.

"U.S. Appl. No. 17/241,924, Non Final Office Action mailed Jul. 12, 2021".

"U.S. Appl. No. 17/241,924, Response filed Oct. 12, 2021 to Non Final Office Action mailed Jul. 12, 2021", 17 pgs.

"U.S. Appl. No. 17/241,924, Notice of Allowance mailed Oct. 28, 2021", 5 pgs.

(56) References Cited

OTHER PUBLICATIONS

Allen, R P, "Restless Legs Syndrome Willis-Eckbom Disease Pathophysiology", Sleep Med Clin., 10(3), (2015), 207-214.

Clemens, S, "Restless leg syndrome: revisiting the dopamine hypothesis from the spinal cord perspective", Neurology, 67, (2006), 7 pgs.

Hayashibe, Mitsuhiro, "Evoked Electromyographically Controlled Electrical Stimulation", Frontiers in Neuroscience, (Jul. 14, 2016), 7 pgs.

Kilgore, K. L, "Nerve conduction block utilising high-frequency alternating current.", Med Biol Eng Comput., 42(3), (May 2004), 394-406.

Mitchell, U, "Medical devices for restless leg syndrome—clinical utility of the Relaxis pad", Ther and Clin Risk Management, (2015), 1789-1794.

Qing, K, "Burst-Modulated Waveforms Optimize Electrical Stimuli for Charge Efficiency and Fiber Selectivity", IEEE Trans Neural Syst Rehabil Eng 23(6), (Nov. 2015), pp. 936-945.

Schoen, Nathan, "The Use of Intraoperative Electromyogram During Spinal Cord Stimulator Placement Surgery: A Case Series", World Neurosurgery vol. 100, (Apr. 2017), pp. 74-84.

Stewart, W, "Prevalence and burden of overactive bladder in the United States", World J Urol, 20 327-336, (2003), 11 pgs.

Vance, Carol GT, "Using TENS for pain control: the state of the evidence", Pain Management 4(3), 197-209, (2014), 13 pgs.

"European Application Serial No. 20793537.0, Response to Communication pursuant to Rules 161(1) and 162 EPC Response filed Nov. 23, 2022", 41 pgs.

"U.S. Appl. No. 17/583,990, Preliminary Amendment filed Apr. 4, 2022", 9 pgs.

"International Application Serial No. PCT US2020 054006, International Preliminary Report on Patentability mailed Apr. 14, 2022", 10 pgs.

"Chinese Application Serial No. 202080078972.6, Notification to Make Rectification mailed Jun. 16, 2022", w o English Translation, 1 pg.

U.S. Appl. No. 16/196,863 U.S. Pat. No. 10,342,977, filed Nov. 20, 2018, Restless Leg Syndrome or Overactive Nerve Treatment.

U.S. Appl. No. 17/062,010 U.S. Pat. No. 11,103,691, filed Oct. 2, 2020, Peripheral Nerve Stimulation for Restless Legs Syndrom.

U.S. Appl. No. 17/241,924, filed Apr. 27, 2021, Variable Operating Point Neural Electrostimulation Such as to Treat RLS.

"Japanese Application Serial No. 2022-520538, Notification of Reasons for Refusal mailed Apr. 30, 2024", w/ English translation, 14 pgs.

"U.S. Appl. No. 17/583,990, Non Final Office Action mailed Aug. 28, 2024", 10 pgs.

* cited by examiner

PERIPHERAL NERVE STIMULATION FOR RESTLESS LEGS SYNDROME

CLAIM OF PRIORITY

This application is a continuation of U.S. patent application Ser. No. 17/062,010, filed Oct. 2, 2020, entitled PERIPHERAL NERVE STIMULATION FOR RESTLESS LEGS SYNDROME, which claims the benefit of priority of: (1) Charlesworth et al. U.S. Provisional Application Ser. No. 62/910,241, filed Oct. 3, 2019 entitled PERSONALIZED SCREENING OR TUNING FOR NEUROSTIMULATION; and (2) Charlesworth et al. U.S. Provisional Application Ser. No. 62/706,525, filed on Aug. 22, 2020 entitled SYSTEMS AND METHODS FOR PERIPHERAL NERVE STIMULATION FOR TREATMENT OF RESTLESS LEGS SYNDROME, each of which is hereby incorporated herein by reference.

CROSS REFERENCE TO RELATED APPLICATIONS

This application is related to U.S. Pat. No. 10,342,977, filed issued Jul. 9, 2019, which was a continuation of PCT/US2018/012631, filed Jan. 5, 2018 and which claims the priority benefit of U.S. Provisional Application Ser. Nos. 62/442,798, filed Jan. 5, 2017, and 62/552,690, filed Aug. 31, 2019. This application is also related to U.S. Provisional Application Ser. Nos. 62/910,241, filed Oct. 3, 2019, and 63/016,052 filed Apr. 27, 2020. All of the foregoing applications are incorporated herein by reference in their entirety.

TECHNICAL FIELD

The present disclosure relates to neurostimulation, and more particularly to systems and methods for identifying, assessing, and treating patients having a neural disorder, including without limitation Restless Legs Syndrome (RLS) or Periodic Leg Movement Disorder (PLMD). This document also relates to personalized screening or tuning for nerve stimulation, such as to address hyperexcitability of one or more nerves or one or more associated symptoms.

BACKGROUND

Electrical nerve stimulation can be used to treat one or more conditions, such as chronic or acute pain, epilepsy, depression, bladder disorders, or inflammatory disorders. There can be significant variability in the efficacy of the electrical nerve stimulation signal in activating the target nerve, particularly when the stimulation signal is delivered transcutaneously (e.g., applied externally to the skin to a neural target within or under the skin), and in recruiting particular nerve fibers to achieve a desired effect. Establishing safe and reliable nerve recruitment can thus be challenging, and treatment of a particular disorder may depend upon the nerve type (e.g., with central or peripheral nervous system), function (e.g., motor or sensory) and specific fibers (e.g., A-α, A-β, A-λ, B, or C fibers) to be activated.

Certain neurological disorders can be attributed to overactivity of sensory or other peripheral nerve fibers which can disrupt quality of life, and/or the processing of such neural activity in the brain. Restless Legs Syndrome (RLS) and Periodic Leg Movement Disorder (PLMD) are two such neurological conditions that can significantly affect sleep in human patients. RLS (which can also be called Willis-Ekbom Disease (WED)) patients can experience uncomfortable tingling sensations in their lower limbs (legs) and, less frequently in the upper limbs (arms). RLS is characterized by an uncontrollable urge to move the affected limb(s). Such sensations can often be temporarily relieved by moving the limb voluntarily, but doing so can interfere with the RLS patient's ability to fall asleep. PLMD patients can experience spontaneous movements of the lower legs during periods of sleep, which can cause the PLMD patient to wake up.

Moderate to severe RLS can be a debilitating sleep disorder. Many RLS patients become refractory to the leading RLS medications yet have few alternatives. For a patient diagnosed with primary RLS (e.g., not secondary to some other primary co-morbidity, such as diabetes, neuropathy, etc.), the first line of treatment may involve one or more of behavior changes, sleep changes, or exercise. The second line of treatment may involve dopaminergic therapy or iron level management, or both. Dopaminergic therapy frequently leads to tolerance of the drug (termed augmentation), such that RLS patients must increase the dosage over time. Even under the highest safe dosages, efficacy of dopaminergic therapy declines significantly. The third line of treatment may involve one or more of anti-convulsants, off-label opioids, or benzodiazepines. The pharmaceutical therapies that are frequently part of current treatments for RLS patients can have serious side-effects, which may include progressively worsening RLS symptoms. There have been case reports of improvement in RLS symptoms for patients with having implanted spinal cord stimulation (SCS) therapy for pain. However, the use of implanted medical devices presents significant additional risks to patient health, are unproven, and are very expensive—and thus are not part of the standard of care. Accordingly, there is substantial patient and clinician interest in a low-risk medical device treatment as an alternative to medication and medical implants.

BRIEF SUMMARY

The following presents a simplified summary of one or more examples in order to provide a basic understanding of such examples. This summary is not an extensive overview of all contemplated examples, and is intended to neither identify key or critical elements of all examples nor delineate the scope of any or all examples. Its purpose is to present some concepts of one or more examples in a simplified form as a prelude to the more detailed description that is presented below.

In an embodiment, the present techniques can include a method of treating a patient having one or more symptoms associated with at least one of Restless Legs Syndrome (RLS) and Periodic Limb Movement Disorder (PLMD) using applied high-frequency electrostimulation, the method comprising: coupling at least one first electrostimulation electrode to at least a first external target body location of the patient proximate to a peroneal nerve or a branch thereof; and delivering a first high-frequency pulsed electrostimulation therapy signal to the at least a first external target body location using the at least one first electrostimulation electrode, wherein the pulses of the electrostimulation therapy signal are defined by a plurality of parameters including at least a frequency of between 500 and 10,000 Hz, and a current of between 5 and 50 mA, and wherein the electrostimulation therapy signal is above a tonic motor threshold of at least one muscle innervated by the peroneal nerve or a branch thereof, and below a pain threshold.

In an embodiment, the the present techniques can include a method of determining stimulation parameters for a non-invasive peripheral neurostimulation therapy comprising: coupling at least one first electrostimulation electrode to a first external target body location of the patient proximate to a peroneal nerve or a branch thereof; coupling at least one first EMG sensing electrode to the skin of the patient proximate to a muscle innervated by the peroneal nerve or a branch thereof; delivering a high-frequency pulsed electrostimulation test signal to the peroneal nerve or a branch thereof, wherein the pulses of the electrostimulation test signal are defined by a plurality of parameters including at least a frequency of between 500 and 10,000 Hz, and a current of between 0 and 50 mA; sensing EMG activity of the muscle innervated by the peroneal nerve or a branch thereof in response to the electrostimulation test signal; determining whether or not the electrostimulation test signal is above the tonic motor threshold of the muscle and below the pain threshold of the patient based on the sensed EMG activity; repeating the steps of delivering a high-frequency pulsed electrostimulation test signal to the peroneal nerve or a branch thereof, sensing EMG activity of the muscle, and determining whether the electrostimulation test signal is above the tonic motor threshold and below the pain threshold, wherein the pulses of the electrostimulation therapy for each repetition of delivering an electrostimulation test signal have at least one of a different frequency and a different current than an immediately preceding electrostimulation test signal; and selecting one of the electrostimulation test signals that is above the tonic motor threshold and below the pain threshold as a high-frequency pulsed electrostimulation therapy signal.

In an embodiment, the present techniques can include a method of determining one or more patient thresholds for a noninvasive peripheral neurostimulation therapy comprising: coupling at least one first electrostimulation electrode to a first external target body location of the patient proximate to a peroneal nerve or a branch thereof; coupling at least one first EMG sensing electrode to the skin of the patient proximate to a muscle innervated by the peroneal nerve or a branch thereof; delivering a high-frequency pulsed electrostimulation test signal to the peroneal nerve or a branch thereof, wherein the pulses of the electrostimulation test signal are defined by a plurality of parameters including at least a frequency of between 500 and 10,000 Hz, and a current of between 0 and 50 mA; sensing EMG activity of the muscle innervated by the peroneal nerve or a branch thereof in response to the electrostimulation test signal; determining whether the electrostimulation test signal is above the tonic motor threshold of the muscle and below the pain threshold of the patient based on the sensed EMG activity; determining whether or not the electrostimulation test signal is above one or more of a sensory threshold, a distraction threshold, a tolerability threshold, or a pain threshold based on patient feedback; repeating the steps of delivering a high-frequency pulsed electrostimulation test signal to the peroneal nerve or a branch thereof, sensing EMG activity of the muscle, determining whether the electrostimulation test signal is above the tonic motor threshold and below the pain threshold, and determining whether or not the electrostimulation test signal is above one or more of a sensory threshold, a distraction threshold, a tolerability threshold, and a pain threshold based on patient feedback, wherein the pulses of the electrostimulation therapy for each repetition of delivering an electrostimulation test signal have at least one of a different frequency and a different current than an immediately preceding electrostimulation test signal; identifying a tonic motor threshold and at least one of a sensor threshold, a distraction threshold, a tolerability threshold, and a pain threshold; and performing a further action selected from: logging the identified thresholds; selecting at least one of the high-frequency pulsed electrostimulation test signals for application to the peroneal nerve or a branch thereof; and identifying a change in at least one of the identified thresholds from a previously-determined threshold.

To recap and provide additional overview, the present inventors have, among other things, identified that surface EMG, recorded from the muscle attached to the innervating nerve being electrostimulated, an provide a good "feedback signal" or other indication such as can provide information regarding whether the non-invasive electrical neurostimulation stimulus is producing (or a "predictor feedback signal" or other predictive indicator of whether it will produce) a desired effect. Moreover, such surface EMG activity can be observed and recorded even before the subject has reported feeling the presence of any stimulation, that is, even while the stimulation is sub-sensory. Moreover, different patients can be observed to exhibit a surface EMG signal in response to a different combination of one or more electrostimulation parameters (e.g., frequency, pulse width, or the like), such that the combination of parameters can be established or adjusted in a manner to serve to increase or maximize the observed surface EMG activation response in a particular patient.

This surface EMG signal information can be gathered and used in one or more ways. For example, one or more electrostimulation parameters (e.g., frequency, pulse width, or the like) can be varied, and the resulting surface EMG signal can be observed and used, such as to select one or more electrostimulation settings or one or more electrostimulation waveforms that best meets a specified goal, e.g., results in the least electrostimulation power consumption (e.g., to reduce heat, extend battery life, or the like) while producing the most surface EMG activation for that specific subject.

In another illustrative example, one or more electrostimulation parameters (e.g., frequency, pulse width, or the like) can be varied and the resulting surface EMG signal can be observed and used to select an electrostimulation waveform such as for use at a particular time of day, such as during a specified time period corresponding to nighttime, e.g., during which the nighttime goal can be to maximize surface EMG activation response to the electrostimulation while remaining below the subject's indicated distraction threshold. In another illustrative example, one or more electrostimulation parameters (e.g., frequency, pulse width, or the like) can be varied and the resulting surface EMG signal can be observed and can be used to select an an electrostimulation waveform such as for use during a specified daytime time period, e.g., during which the goal can be to maximize the surface EMG activation response while remaining below subject's pain or discomfort threshold (which is usually above the patient's distraction threshold). More specific and more general examples are also described in this document.

As explained above, electrical nerve stimulation can be used to treat one or more conditions such as chronic or acute pain, bladder disorders, or inflammatory disorders. There can be significant variability in the effects of electrostimulation, particularly when delivered transcutaneously (via the skin) instead of using an implanted electrode. This is presumably because of the added variability of transcutaneous electrostimulation, such as can be due to one or more of device positioning or placement on the patient's body, bioelectrical impedance such as of the patient's skin, or the particular patient's subjective tolerability of electrostimulation-induced paraesthesias such as at higher electrostimulation energy intensities. As an example, one review of transcutaneous electrical nerve stimulation (TENS) found that the studies in the last decade on TENS have lacked consistency and vary between showing efficacy of TENS and not showing any efficacy of TENS when used to treat pain (see https://www.ncbi.nlm.nih.gov/pmc/articles/PMC4186747/).

This subjective variability in electrostimulation effectiveness can also exist in patients undergoing implantable sacral nerve stimulation such as for treating overactive bladder (OAB). In indications such as OAB, the variability in electrostimulation treatment effectiveness may be addressed by prompting a patient to first get a temporary external electrostimulation device, such as for use during an initial period of time, such as to assess effectiveness of electrostimulation using the temporary device, before the patient is deemed to qualify to get a permanent OAB electrostimulation implant. Similar protocols can be followed for patients who are eligible to get an implantable spinal cord stimulation (SCS) device to treat pain. In an approach, the only normalized way to dose electrostimulation therapy is by controlling either the output current (I) or the voltage (V) for the same the frequency and pulse width of the waveform used across different patients. This approach, however, can present a unique challenge in that an electrostimulation dose level that may demonstrate therapeutic benefit in one patient may be far from what is tolerable in another patient, or may be completely ineffective in a third patient, for example.

Mechanistically, a purpose of electrostimulation can be to electrically activate one or more nerve fibers such as to produce a desired cascade of neural responses such as can then trigger a resulting therapeutic effect. One approach to personalization of electrostimulation therapy can require waiting to evaluate the presence or degree of the resulting therapeutic effect, which can require weeks to occur, and which can be highly subjective (e.g., in the case of chronic pain). Another approach to personalization of electrostimulation therapy can be to measure the neural response, which can occur within milliseconds, and which can be more objectively measured as compared to the resulting therapeutic effect. Given the rapidity of such a measured neural response technique, multiple modes of electrostimulation (e.g., varying in amplitude, power, frequency, pulse width, or the like) can even be tested within a single outpatient visit, thereby allowing rapid personalization of the electrostimulation therapy.

Individuals can vary in their response to medical treatments. Thus, response data-driven personalization of care has the potential to improve individual patient outcomes and to reduce individual or global treatment costs. Compared to pharmaceutical therapies, electrical neurostimulation therapies have a particularly large potential for benefitting from personalization because such electrostimulation therapies are not necessarily monolithic. Instead, nerve stimulation can be optimized or adjusted, such as by programmatically adjusting one or more of the parameters of the electrical neurostimulation. Some approaches to such optimization can be costly and slow, and can require optimization by a highly trained medical professional based on a patient's subjective response about the ultimate intended therapeutic effect, such as after the patient has used the product over a long enough period of time to observe such therapeutic effect, such as can involve a period of weeks or months. The present inventors have recognized, among other things, that a closed-loop or similar system that can adjust or optimize treatment quickly or even automatically can be tremendously valuable in terms of saving time and money and improving individual patient treatment outcomes. Further, such a system can be used to rapidly predict and differentiate between "responder" patients who will (and "non-responder" patients who will not) experience therapeutic benefits from a given therapy. This, in turn, can help improve clinical outcomes, reduce costs, and improve success rates for clinical trials.

One approach that can help improve the establishing, adjusting, or optimizing of one or more parameters of a more monolithic (non-personalized) therapy can include, for example, determining whether all patients in a group or population or subpopulation should receive Stimulation Approach 1 or Stimulation Approach 2. For example, an EMG signal can be observed using in an in vitro animal preparation, such as to demonstrate whether DC electrostimulation followed by AC electrostimulation can lead to better nerve block than AC electrostimulation delivered alone, and this information can be used to select a desired approach for all patients in a group or population or subpopulation. In another approach, one or more elicited reflexes (e.g., flexor response or sometimes referred to as flexion response) in one or more human subjects can be used together with measured surface EMG signals in the one or more human subjects, such as to help identify relative effectiveness in a particular human subject or in a group of human subjects of the electrostimulation according to one or more electrical neurostimulation parameters. For example, such an approach can be used to help evaluate various frequencies of electrical neurostimulation for a particular human subject or for a group of human subjects. An illustrative example of using flexion response, such as in an illustrative RLS use case context, is described in Raghunathan U.S. Pat. No. 10,342,977, which is incorporated by reference herein in its entirety, including for its teaching of flexion response, which can be used in combination with the surface EMG signal techniques described in the present document.

As promising as these approaches may be for improving a more monolithic therapy, approaches not using surface EMG signal may not always be as useful for within-patient screening or personalization of one or more electrical neurostimulation parameters. This can be due to one or more factors such as, for example: (1) interference from the electrical neurostimulus signal; (2) low-amplitude of measured flexion response; (3) distance of recording of flexion response from actual nerve target (e.g., in a transcutaneous application); (4) need for multiple channels of signal recording of flexion response; (5) a random or inconsistent nature of flexion responses; and (6) lack of automation and thus requirement for extensive technician training of interpreting flexion responses. Thus, the present techniques of using surface EMG data as an alternative or supplement to flexion response evaluation can be useful, such as for patient screening, for establishing or adjusting patient therapy, for evaluating therapy efficacy, or for one or more other purposes, such as explained further elsewhere in this document.

BRIEF DESCRIPTION OF THE FIGURES

For a better understanding of the various described examples, reference should be made to the description below, in conjunction with the following figures in which like reference numerals refer to corresponding similar parts throughout the figures.

DETAILED DESCRIPTION

Figure 3:
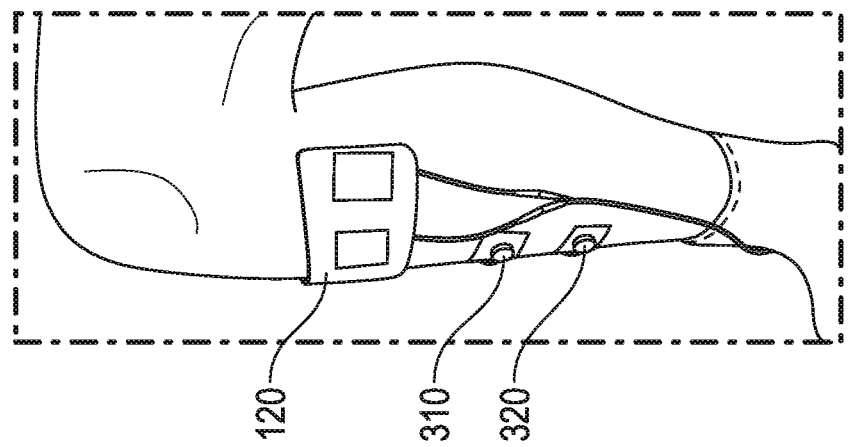
FIG. 3 illustrates an electrode patch for delivering an electrostimulation signal to a peroneal nerve, and surface EMG sensing electrodes for sensing an evoked response to the electrostimulation signal.

As used herein, "sensory threshold" refers to the lowest stimulation level (as expressed in a particular combination of electrostimulation parameters defining a pulsed electrical signal, e.g., pulse current, pulse width, pulse waveform, etc.) at which a pulsed electrostimulation signal is perceptible to a patient receiving the electrostimulation signal.

The term "tonic muscle activation" refers to an isometric muscle contraction or similar muscle activation that is sustained and consistent over time and does not induce periodic leg movements (e.g., clonic or jerking movements occurring at a rate exceeding once per minute). When measured by a surface electromyogram (sEMG) sensed from the skin of the patient above the activated muscle, the sEMG activity induced by the tonic activation is characterized by consistently elevated amplitude over baseline with no significant short-lived changes in amplitude. The increase in muscle tone may (or may not) be noticeable to the patient or an observer, but there are no noticeable rapid movements or jerks.

The term "phasic muscle activation" refers to activation that induces period leg movements that are noticeable to the patient or an observer and which occur at least once per minute. Movements associated with phasic muscle activation may appear as a twitch, kick, or jerk, and the associated sEMG signal is characterized by large, abrupt, short-lived (e.g., <1 second) changes in amplitude.

The term "tonic motor threshold" refers to the lowest stimulation level (as expressed by a particular combination of electrostimulation parameters defining a pulsed electrostimulation signal, e.g., current, pulse width, pulse waveform, etc.) at which a pulsed electrostimulation signal causes specifically tonic muscle activation (as opposed to no muscle activation, phasic muscle activation, or a combination of tonic and phasic muscle activation), such that decreasing one of the parameters defining the pulsed electrostimulation signal would result in no tonic muscle activation of the muscle innervated by the electrostimulation signal. If there is no stimulation level that generates tonic muscle activation in the absence of phasic muscle activation, then the tonic motor threshold is undefined.

The term "distraction threshold" refers to the highest electrostimulation level (as expressed by a particular combination of electrostimulation parameters) that is comfortable, non-distracting, and compatible with a particular activity. For example, a sleep distraction threshold refers to the highest stimulation level that is comfortable, non-distracting, and compatible with sleep, such that increasing one of the parameters defining the sleep distraction threshold would result in a stimulation level that is incompatible with sleep. The sleep distraction threshold may be established by one or more of 1) the patient's subjective opinion (e.g., while awake and receiving an electrostimulation test signal); 2) an adverse effect on the patient's sleep while receiving an electrostimulation signal compared to no signal, such as A) an increase in sleep onset latency (i.e., time needed for the patient to fall asleep), B) an increase in sleep fragmentation as determined by one or more body parameters such as sleep movement, EEG signals, heart rate signals, etc., C) a decrease in sleep efficiency, D) a decrease in total sleep time, or E) an increase in wakefulness or arousal episodes after sleep onset. Other distraction thresholds (for example, working distraction threshold) may also be identified by testing a patient while the patient has the particular activity in mind or is performing the activity.

The term "tolerability threshold" refers to the highest stimulation level (as expressed by a particular combination of electrostimulation parameters) that a patient could tolerate for a period of one minute, in the patient's subjective opinion. The tolerability threshold refers to a level of stimulation that the patient experiences as distracting or uncomfortable, but which may be tolerated for a short period of time and is not painful.

The term "pain threshold" refers to the minimum stimulation level (as expressed by a particular combination of electrostimulation parameters) that the patient experiences as painful.

The term "electrostimulation test signal" (ETS) refers to a pulsed electrostimulation signal defined by a plurality of parameters (e.g., pulse current, pulse width, pulse waveform, etc.) that is applied to a body location proximate to a target nerve structure (e.g., a peroneal, sural, or femoral nerve or branch thereof) for the purpose of determining a patient response to the ETS. As nonlimiting example, the response may comprise a surface EMG (sEMG) response of a muscle innervated by the target nerve structure to the ETS, a patient subjective patient perception of the response (e.g., the ETS is imperceptible, is perceptible but not comfortable, is perceptible but non-distracting, is perceptible but tolerable).

The present inventors have identified that surface EMG (sEMG), determined from a muscle innervated by a nerve being stimulated by an electrostimulation signal as part of a therapy regimen for one or more neurological disorders such as RLS or PLMD, can be used as a feedback signal to determine whether the electrostimulation signal is producing (or is likely to produce) a desired effect. Many neural electrostimulation therapies would otherwise require weeks or months before a determination can be made as to whether the therapy is effective. Feedback from one or more body parameters (e.g., heart rate, breathing rate, etc.) have been proposed as potential indicators of efficacy. In many instances such body parameters are poorly correlated with efficacy. In contrast, the present inventors have appreciated in the present context of using high-frequency pulsed electrostimulation therapy signals to treat symptoms of RLS or PLMD, there is a relatively good correlation between tonic motor thresholds for sustained tonic activation of muscles innervated by a target peroneal nerve structure and therapeutic efficacy.

In one aspect, sEMG can be used to identify one or more thresholds relevant to providing efficacious electrostimulation therapy to treat RLS symptoms. In an embodiment, sEMG responses to one or more electrostimulation test signals may be determined (e.g., using sEMG sensing electrodes) and used to identify a tonic motor threshold. In another embodiment, a plurality of electrostimulation test signals may be delivered according to a test protocol test as discussed in connection with FIG. 4, and the patient may provide subjective responses (e.g., verbally or using an input device) to a changing electrostimulation test signal to determine one or more of a distraction threshold, a tolerability threshold, and a pain threshold.

The one or more thresholds can be used in various embodiments to perform a variety of tasks. In an embodiment, one or more of the thresholds may be used to screen patients (e.g., identify potential responders and/or nonresponders to NPNS therapy for treating RLS/PLMD). In another embodiment, the one or more sEMG thresholds may be used to identify stimulation parameters that are likely to be efficacious in relieving one or more RLS symptoms. In a further embodiment, the one or more sEMG thresholds may be used to change therapy parameters such as to help avoid nerve accommodation or tolerance while remaining efficacious in relieving one or more RLS symptoms. In an additional embodiment, the one or more sEMG thresholds may be used to control one or more electrostimulation parameters such as to achieve one or more additional goals, e.g., achieving increased or maximum therapeutic efficacy, minimizing or reducing power consumption while retaining therapeutic efficacy, minimizing or reducing temperature within or proximal to the electrostimulation device, etc.

In some instances, sEMG activity can observed and recorded even before a patient can sense that an electrostimulation signal is being applied to the target nerve structure (i.e., while the electrostimulation signal is subsensory). Moreover, different patients can be observed to exhibit a distinct surface EMG (sEMG) signal in response to a different combination of one or more electrostimulation parameters (e.g., frequency, pulse width, or the like) that can serve to maximize or otherwise modulate the observed sEMG activation response in a particular patient. Because patient responses to a particular electrostimulation signal may vary significantly, a particular electrostimulation signal threshold (e.g., a sensory threshold, a tonic motor threshold, a distraction threshold, a pain threshold) may occur at widely different parameter settings for different patients.

A surface EMG (sEMG) signal capturing a response of a muscle to one or more electrostimulation test signals (ETS) can be obtained in a variety of ways. In an embodiment, surface electrodes may be externally coupled to the skin of a patient proximal to (e.g., superficial to and adhered to the skin overlying) a muscle innervated by a nerve to be stimulated. In embodiments involving stimulation of a peroneal nerve or branch thereof on a leg of a patient, at least one sensing electrode may be attached (e.g., using adhesive hydrogel electrodes) to one or more muscle, for example, selected from the tibialis anterior, the extensor digitorum longus, the peroneus tertius, the extensor hallucis longus, the fibularis longus, and the fibularis brevis.

Figure 4:
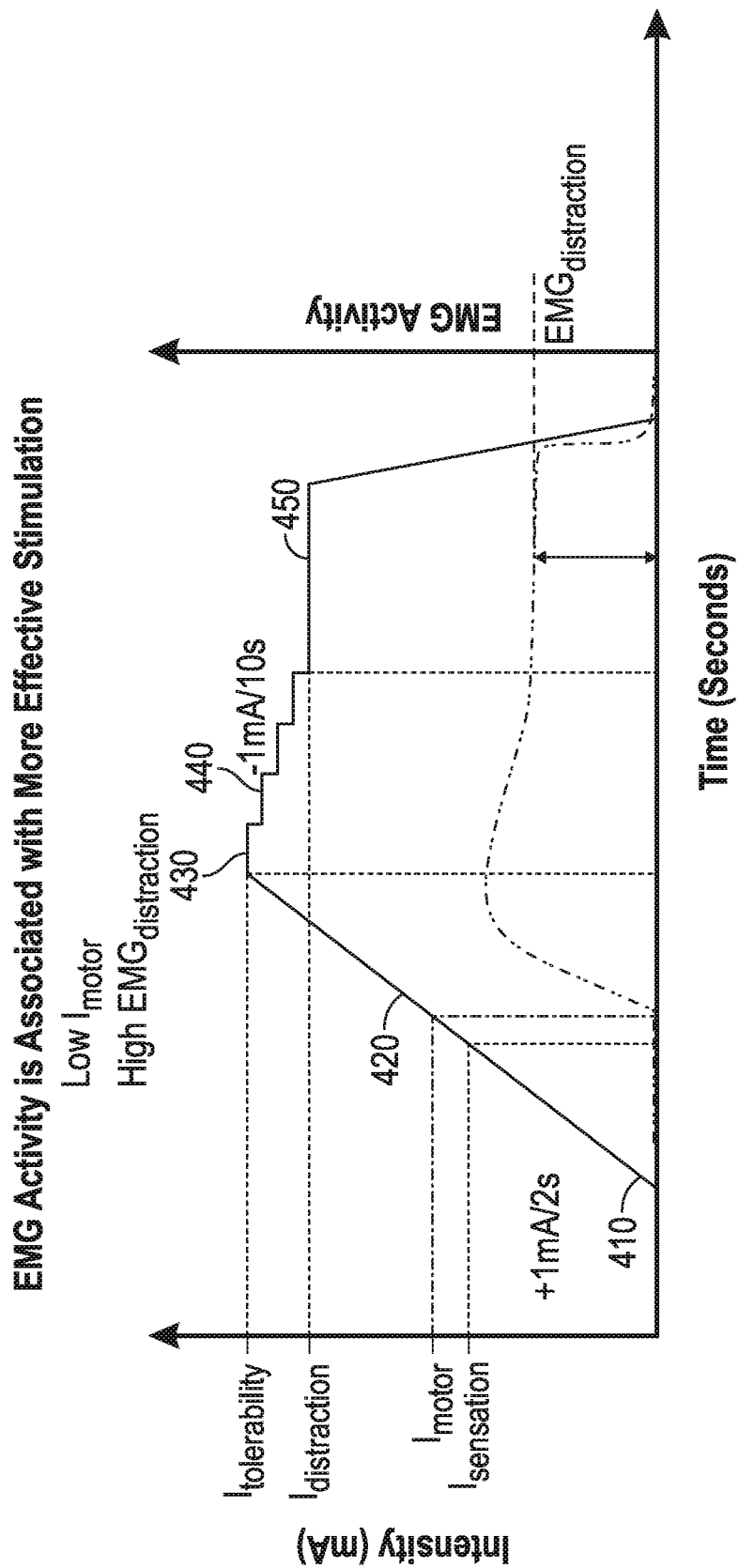
FIG. 4 illustrates a calibration process for identifying one or more thresholds and stimulation parameters for providing a neurostimulation therapy to a patient.

Data may be captured by sensing sEMG activity of a muscle innervated by the electrostimulation test signal using the at least one sensing electrode (e.g., using an electrode pair) during the application electrostimulation signals. In one embodiment, a plurality of test electrostimulation signals may be delivered according to a test protocol using a fixed pulse width and pulse waveform and varying the pulse current in a specified manner, such as that discussed hereinafter in connection with Study 1 (FIG. 4). Surface EMG data may be sensed and processed according to one or more specified protocols, and the patient may be interrogated or may provide input in response to the changing signal in a variety of ways. Accordingly, in one aspect the present systems and methods can include determining one or more of the foregoing thresholds for patients receiving an electrostimulation signal.

In one aspect, the present systems and methods can be used for treating a patient having symptoms associated with RLS or PLMD with a high frequency pulsed electrostimulation signal applied to a peroneal nerve or branch thereof. The high frequency electrostimulation signal may comprise a frequency of between 500 and 15,000 Hz, more preferably 1-10 kHz, and more preferably 2-6 kHz, wherein the electrostimulation signal is above a tonic motor threshold of at least one muscle innervated by the peroneal nerve or branch thereof, and below a pain threshold. In an embodiment, the electrostimulation signal is below a distraction threshold. The present systems and methods can be used for treating a patient having symptoms associated with a hyperactive peripheral nerve, such as with a first high frequency pulsed electrostimulation signal applied to a first neural target on a leg of a patient and a second high frequency pulsed electrostimulation signal applied to a second neural target on an arm of the patient. In an embodiment, the method is used to treat a patient having symptoms associated with RLS or PLMD, the first neural target is selected from one of a peroneal nerve or a branch thereof, a sural nerve or a branch thereof, and a femoral nerve or a branch thereof, and the second neural target is selected from one of an ulnar nerve or a branch thereof and a radial nerve or a branch thereof. The high frequency electrostimulation therapy signals may comprise a frequency of between 500 and 15,000 Hz, more preferably 1-10 kHz, and more preferably 2-6 kHz, wherein the first high frequency electrostimulation therapy signal is above a tonic motor threshold of at least one muscle innervated by the one of a peroneal nerve or a branch thereof, a sural nerve or a branch thereof, and a femoral nerve or a branch thereof, and the second high frequency electrostimulation therapy signal is above a tonic motor threshold of one of an ulnar nerve or a branch thereof and a radial nerve or a branch thereof. In an embodiment, the electrostimulation signal is below a distraction threshold.

Study 1—RLS Treatment with HF Stimulation Above a Tonic Threshold

Experimental

To address the significant unmet need for treating RLS, a study was conducted to evaluate the feasibility of using a non-invasive peripheral nerve stimulation (NPNS) system to stimulate nerve fibers in the lower legs as a target body location that is subjectively associated with RLS symptoms. The study was a randomized, participant-blinded, crossover feasibility study conducted at three clinical sites in the United States. Inclusion criteria were a diagnosis of primary RLS, moderate to severe RLS symptoms (defined as those having a score of at least 15 on the International Restless Legs Syndrome (IRLS) severity scale), age 18 or older, symptoms primarily in the lower legs and/or feet, and primarily in the evening or night. It included patients who were drug-naïve (i.e., had not taken medication to treat their RLS symptoms), patients who formerly took RLS drugs, and patients refractory to medication. Patients who had an active implantable medical device, epilepsy, a skin condition affected device site placement, severe peripheral neuropathy, unstable dose of RLS medication treatment, medication worsening RLS symptoms, or uncontrolled sleep apnea/insomnia unrelated to RLS were excluded.

Patients were initially evaluated for the severity of their RLS on the International Restless Legs Syndrome (IRLS) scale. After identifying patients having a score of at least 15, thirty-nine (39) patients were randomized 1:1 into two groups in a crossover trial. One group received 2 weeks of NPNS therapy followed by a crossover of two weeks of sham stimulation, while the other group received 2 weeks of sham stimulation and were then crossed over to receive two weeks of NPNS therapy. Thirty-five patients completed both interventions 1 and 2.

The median age for all patients was 55.7 years, with 46% males and 54% females. The mean IRLS score for all patients at enrollment was 24.0, with a mean age of RLS onset of 34.4 years and a mean duration of symptoms of 20.9 years. Patients were 46% male and 54% female. Of the 39 patients enrolled, 14 (36%) were naïve to RLS medication, 4 (10%) had discontinued RLS medication, and 21 (54%) were taking RLS medication but were refractory as indicated by their IRLS scores of 15 or greater.

Figure 2:
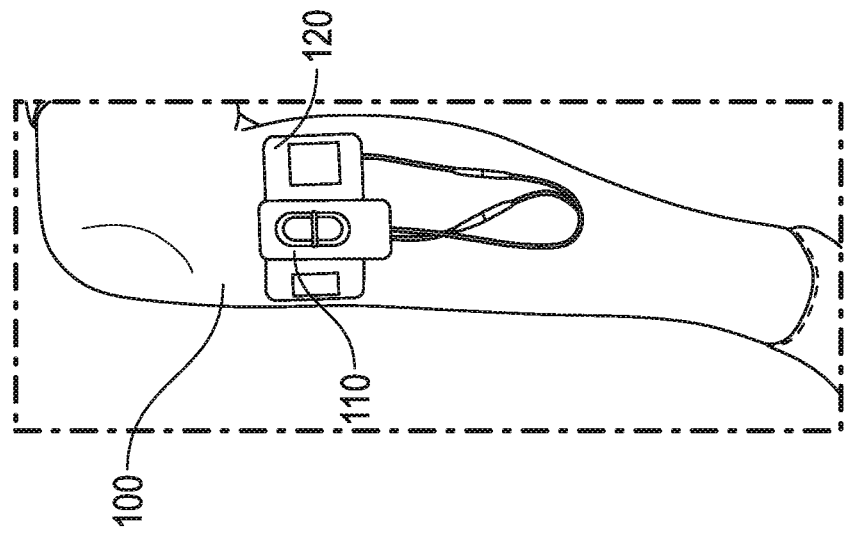
FIG. 2 illustrates a system for treating one or more symptoms of RLS or PLMD by application of an electrostimulation signal to a peroneal nerve, coupled to a left leg of a subject.
Figure 1:
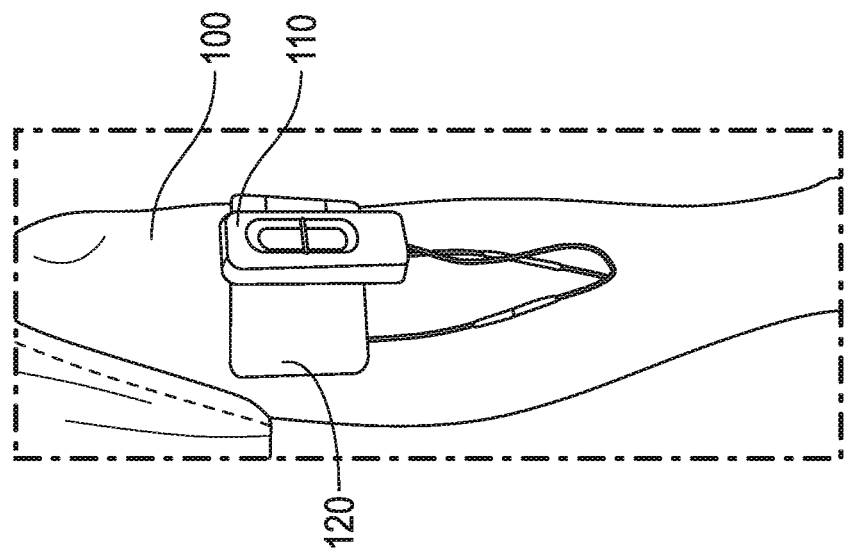
FIG. 1 illustrates a system for treating one or more symptoms of RLS or PLMD by application of an electrostimulation signal to a peroneal nerve, coupled to a right leg of a subject.

Referring to FIGS. 1-3, the system 100 provided a wearable, non-implanted stimulator unit 110 for generating therapeutic electrical pulses, coupled to a wearable external patch 120 (1.3×2.1 in) with adhesive hydrogel electrodes for delivering the electrical pulses to a peroneal nerve. A hydrogel electrode pair (not visible in FIGS. 1-3) was provided on the wearable external patch 120 (FIGS. 1 and 2). FIG. 1 shows a system 100 coupled to a left leg of a subject, while FIG. 2 shows a system 100 coupled to the right leg of a subject.

Separate systems (stimulator unit 110 and patch 120) were placed externally on each leg to provide bilateral transcutaneous stimulation of the left and right superficial peroneal nerves. Each patch 120 was positioned superficially below each knee, over the head of the fibula, in close proximity (i.e., proximal to) the common peroneal nerve. The patches 120 were positioned parallel on the medial-lateral axis, with the shorter dimension on the distal-proximal axis. The lateral upper corner of each patch was positioned to cover part of the head of the fibula bone, with one of the gel electrodes (not shown) over the main section of the left or right superficial peroneal nerve, and the other electrode (not shown) over the region where the superficial peroneal nerve innervates the tibialis anterior muscle.

Patients in the study were instructed to self-administer a NPNS electrostimulation therapy signal to both legs for 30 minutes at or immediately prior to bedtime through a 14-day period. In addition to the bedtime stimulation, patients were allowed to self-administer NPNS multiple times earlier in the day or at night after bedtime as needed (e.g., upon awakening with RLS symptoms). The system provided a high-frequency electrostimulation therapy signal using charge-balanced, controlled current, rectangular pulses at a frequency of 4000 Hz and a pulse with of 125 μsec, and a current of 15-40 mA. The current was set at the distraction threshold of the patient (the highest current at which the 4000 Hz waveform described above was comfortable and compatible with sleep). Because different distraction thresholds vary significantly, distraction thresholds were determined for each patient by an automated electrostimulation test signal (ETS) process in which electrostimulation test signals were applied to the patient and various thresholds, including the distraction threshold, were determined as discussed hereinafter in connection with FIG. 4. The electrostimulation therapy signal (as distinct from the test signal) was delivered continuously during the 30-minute treatment period. Accordingly, the duty cycle (stimulation on-time divided by the sum of stimulation on-time and off-time) was 100% for the 30-minute electrostimulation therapy periods.

Applicants have appreciated that EMG activity, in particular sEMG activity indicative of tonic activation of at least one muscle innervated by the electrostimulation therapy, is associated with efficacy in reducing RLS symptoms. FIG. 3 illustrates a wearable external patch 120 coupled to a right leg of a patient, as in FIG. 2, for delivering an electrostimulation test signal (ETS) or an electrostimulation therapy signal to a peroneal nerve or a branch thereof. FIG. 3 also illustrates sEMG electrodes 310, 320 for sensing an sEMG response to the ETS or electrostimulation therapy signal.

FIG. 4 illustrates a calibration process for determining distraction and other thresholds for each patient used in the study. From a starting current of 0 mA (410), the current value was increased at a rate of 1 mA/2 sec (line 420) to the highest current level that the patient indicated to be tolerable for 1 minute (430), after which the current value was decreased incrementally at a rate of 1 mA/10 sec (region 440) to the highest level that the patient indicated to be non-distracting and compatible with sleeping (450), which was designated as the distraction threshold. The current value was maintained at the distraction threshold (450) for at least 30 seconds and then ramped down to 0 mA within 10 seconds.

For each 30-minute electrostimulation therapy session in active treatment mode, the electrostimulation signal was ramped up to approximately the calibrated distraction threshold current within 30 seconds, remained at the calibrated distraction threshold parameters for 29.5 minutes, ramped down to 0 mA over the final 10 seconds, and shut off automatically. Patients receiving sham stimulation received the initial 30 second period in which the electrostimulation signal was ramped up, but was then ramped down to 0 mA over 10 seconds and remained at 0 mA for the remaining portion of the 30-minute sham treatment period.

It will be appreciated by persons of skill in the art having the benefit of this disclosure that the distraction threshold depends upon the combination of multiple parameters, and where other parameters (e.g., pulse width) are varied, the corresponding current settings will also change. Accordingly, in some embodiments (not shown) the threshold-setting process may involve varying two parameters (e.g., current and pulse width), three parameters (e.g., current, pulse width and frequency), or four or more parameters. Such threshold-setting processes, while more complex and time-consuming than the process illustrated in FIG. 4 in which only the current setting is ramped/varied, will nevertheless be enabled without undue experimentation in view of this disclosure. A programming app (not shown) usable on a handheld computing device (e.g., mobile phone, tablet computer, etc.) wirelessly coupled to the stimulator unit 110 was developed and used to automatically implement the test signal process for establishing the distraction threshold.

Efficacy

Figures 5A, 5B, 5C:
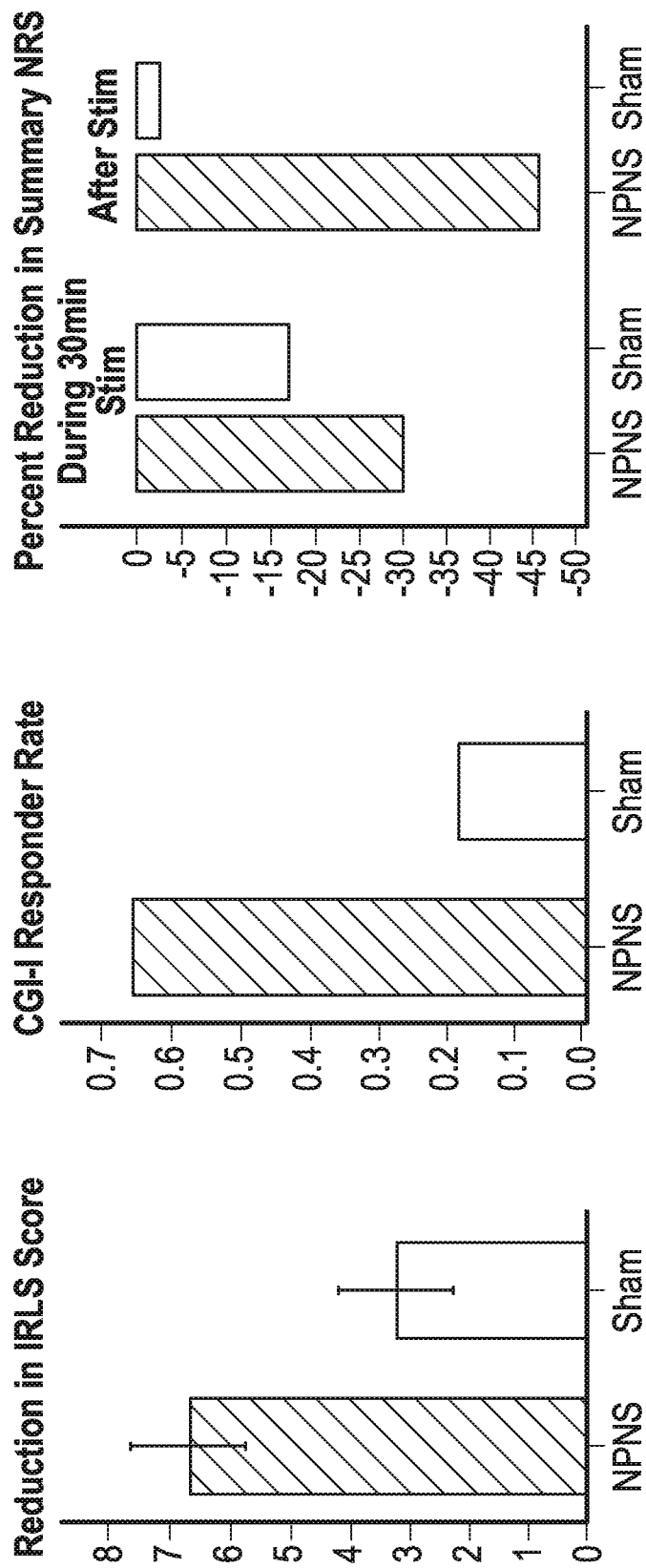
FIGS. 5A-5C illustrate comparison results of NPNS therapy vs. sham for electrostimulation therapy treatment for a plurality of patients.

The study compared the response of patients treated with this regimen of NPNS to the response of an identical sham device. In particular, NPNS led to a reduction of 6.64 points in the severity of RLS as measured by the IRLS scale during week two of device usage relative to the baseline IRLS at study entry. This reduction exceeded the minimally clinically significant reduction of 3.0 points on the IRLS scale, and was also significantly greater than the reduction of 3.15 points associated with sham stimulation, as illustrated in FIG. 5A.

In addition, NPNS resulted in a statistically significant increase in responder rate, the percentage of study participants with a clinically significant response on the patient-rated CGI-Improvement (CGI-I) scale. As illustrated in FIG. 5B, 66% of participants responded to NPNS compared to 17% for sham.

Finally, NPNS acutely reduced RLS severity, as measured by patient-reported numerical rating scale (NRS) ratings of RLS symptom severity. Patients rated RLS symptoms Before, During, and After each nightly 30 min use of the stimulation device using the NRS scale, which was administered in a summary format after each 14-day treatment period and also in a daily format via an online questionnaire. For both the biweekly and daily NRS ratings, NPNS resulted in a statistically significant reduction in average RLS severity "During" and "After" stimulation, thus indicating that NPNS acutely reduces RLS symptoms immediately following stimulation (FIG. 5C).

SIT Data

To further investigate the timing of patient response to stimulation, we employed a Suggested Immobilization Test (SIT), a 60-minute protocol designed to exacerbate and measure RLS symptoms. Consistent with the SIT protocol described by Garcia-Borreguero et al., participants were instructed to sit in a fixed position but were permitted to move their legs to the extent necessary to relieve RLS symptoms. Three SIT procedures were completed by each patient on separate lab visits, one at study entry with no treatment (baseline), one with 60 minutes of concurrent NPNS stimulation immediately following the 2-wk NPNS treatment, and one with 60 minutes of concurrent sham treatment immediately following the 2-wk sham treatment protocol.

Figure 6A:
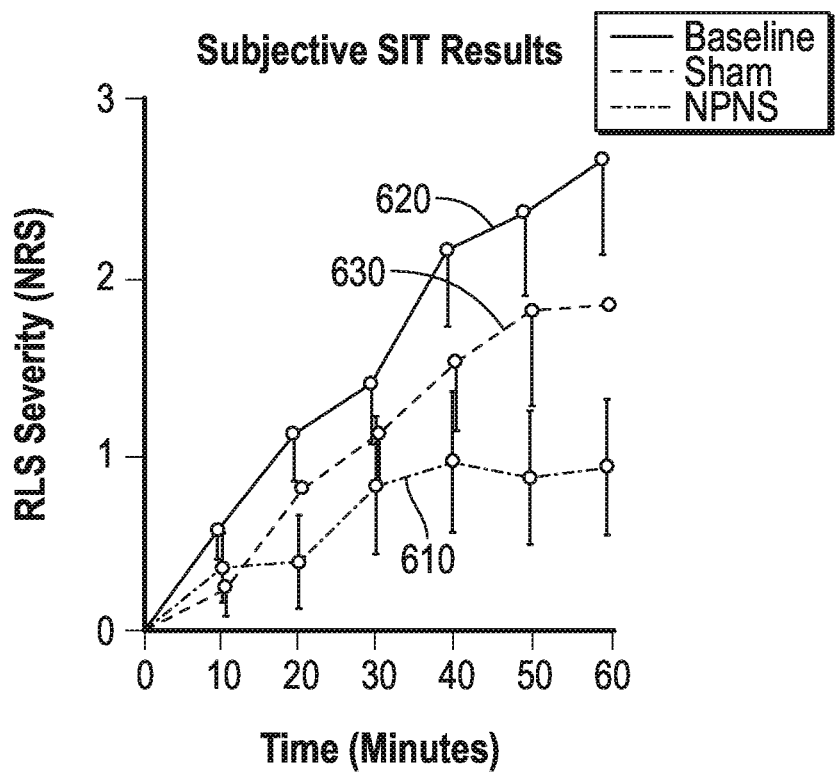
FIGS. 6A and 6B illustrates comparison results for NPNS therapy vs. sham stimulation applied during a Suggested Immobilization Test (SIT) for a plurality of patients having RLS symptoms.
Figure 6B:
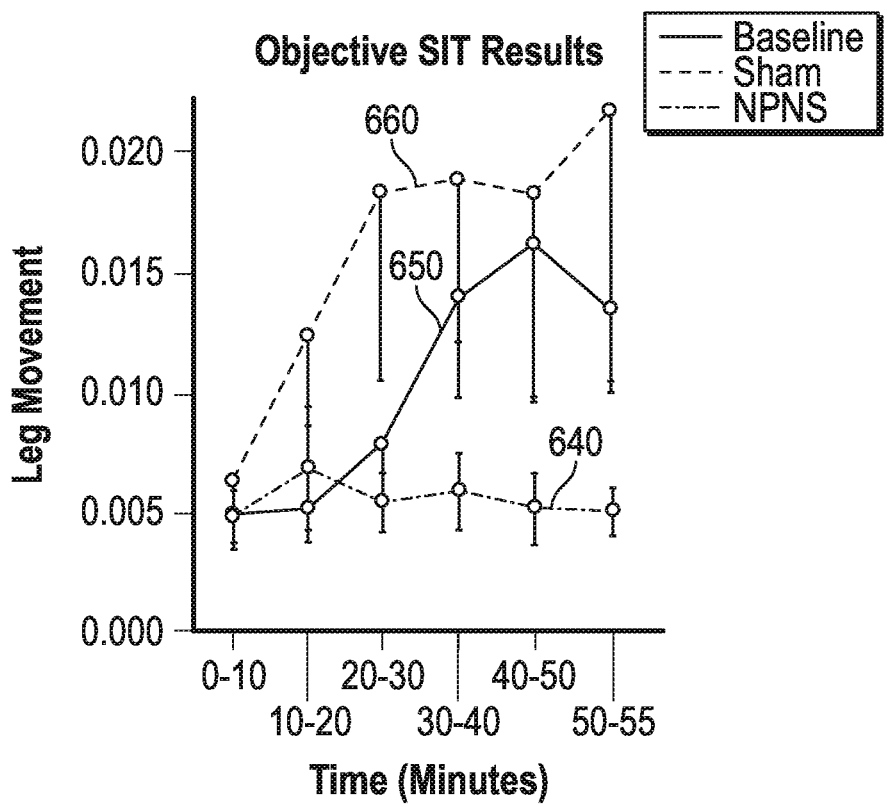

NPNS reduced subjective ratings of RLS severity during the SIT. As illustrated in FIG. 6A, NPNS (data line 610) reduced NRS rating of RLS discomfort relative to Baseline (data line 620) and showed a strong but non-significant trend towards reducing NRS scores relative to Sham (data line 630). There was no indication that the effects of NPNS weakened with time. On the contrary, the reduction in NRS appeared to persist throughout the 60-minute procedure. NPNS also reduced leg movement during the SIT. A 3-axis accelerometer was positioned on each ankle at the lateral malleolus and used to measure total movement of the legs during the SIT procedure. Data was collected at 25 Hz and highpass filtered at 1 Hz to remove gravity force and sensor drift. Acceleration magnitude, calculated as the square root of the sum of the $x^2$, $y^2$, and $z^2$, was calculated for each 10-minute segment during the SIT test, except that data for the last 5 minutes of the 60-minute period was discarded. Data were averaged for the two legs at each timepoint. As illustrated in FIG. 6B, NPNS (data line 640) reduced total leg acceleration relative to baseline (data line 650) and relative to sham (data line 660).

Drug-resistant and drug naïve patients Drug-resistant and drug-naïve participants exhibited similar responses to NPNS. The drug-resistant patient cohort exhibited a statistically significant reduction in IRLS of 7.30 points with NPNS compared to 3.45 points for sham and had a significantly higher responder rate for NPNS compared to sham. The drug-naïve cohort exhibited a similar NPNS response to the full study population on the IRLS in terms of magnitude (7.08 vs. 6.64), and exhibited a similar responder rate on the CGI-I (64%) to the full study population (66%). Comparisons to sham approached but did not reach statistical significance due to the small sample size (n=12).

EMG Data

Figure 7:
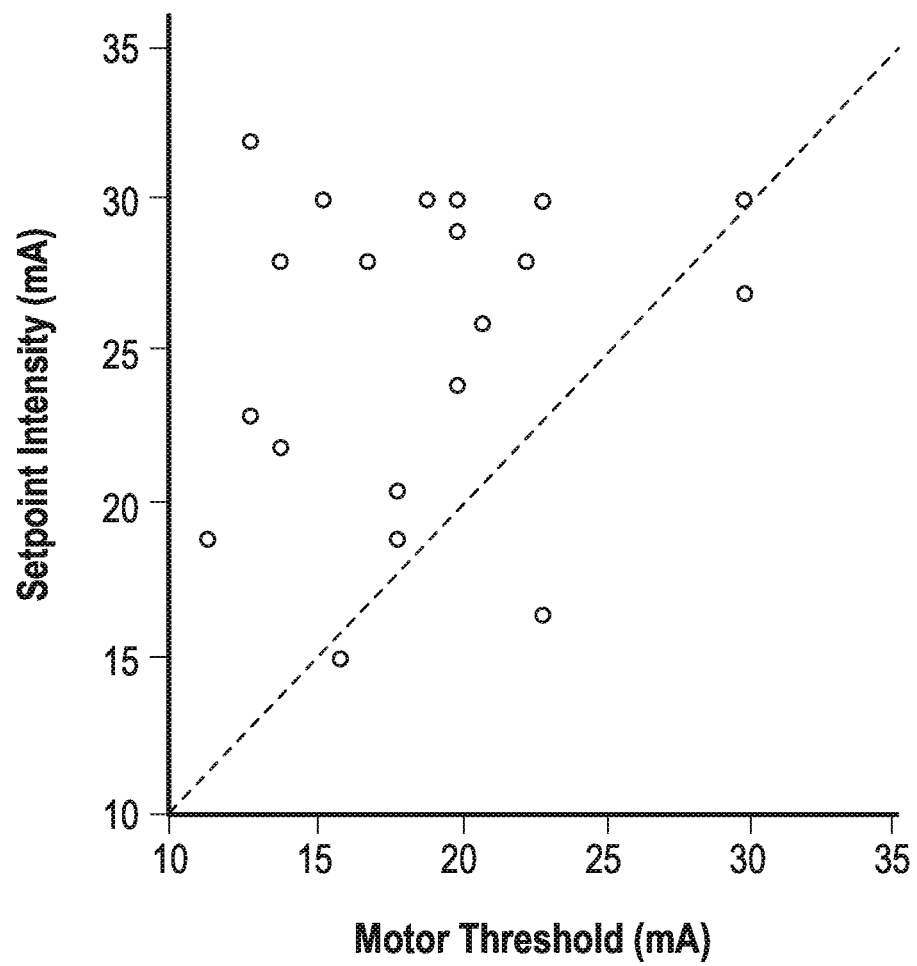
FIG. 7 is a graph of setpoint intensity (current) vs. tonic motor threshold for a plurality of RLS patients.

To investigate the physiological mechanism for NPNS-based relief of RLS symptoms, measurements of sEMG activity in the tibialis anterior (TA) muscle of the lower leg were performed for some patients during calibration of stimulation intensity. The tibialis anterior is a large and superficial muscle that is innervated by the peroneal nerve, the putative nerve target of NPNS in Study 1. The minimal stimulation intensity for evoking tonic muscle activation but not phasic muscle activation (the tonic motor threshold, FIG. 4, $I_{motor}$) was compared to the intensity setting for in-home stimulation ("setpoint"), which was set at the maximal comfortable and non-distracting intensity (the distraction threshold, FIG. 4, $I_{distraction}$). On average, the tonic motor threshold was 7.2 mA below the setpoint (18.2 mA vs. 25.4 mA). Moreover, the tonic motor threshold was below the setpoint in 87% of participants (FIG. 7), meaning that NPNS at the setpoint yielded motor activation for most patients. Notably, the stimulation-evoked EMG activity was tonic, not phasic.

Applicants have appreciated that the tonic motor threshold correlates with efficacy. In particular, the lower the intensity of stimulation at which an electrostimulation signal applied to a peroneal nerve evoked tonic activity in the tibialis anterior muscle, the greater the likelihood of the patient responding to the therapy and achieving relief of RLS or PLMD symptoms. Stated differently, the lower the tonic motor threshold (e.g., for a series of electrostimulation test signals having a fixed pulse width and waveform, the lower the current setting necessary to evoke tonic sEMG activity in the tibialis anterior muscle), the greater the likelihood that NPNS will provide relief to the patient's RLS symptoms. Without being bound by theory, this may be because the peripheral nerves are more sensitive to NPNS delivered via the approach described above, such as may be due to properties of the nerve fibers, due to properties of the layers of tissue between the electrodes and the nerve fibers, and/or due to the positioning of the electrodes relative to the nerve. Accordingly, the data of FIG. 7 data suggest that motor activation may have contributed to the physiological mechanism of NPNS relief.

Overall Results

The results of STUDY 1 suggest that NPNS has the potential to reduce and relieve RLS symptoms when used on a nightly basis. The IRLS is a well-established metric of RLS severity, and the observed reduction of 6.64 points was considerably greater than the minimally clinically significant difference of 3.0 points. Regular usage of NPNS appeared to be important for maintaining RLS symptom relief. There was no evidence of a carry-over effect of either sham or therapy arms into the other arm. Response during sham was equivalent regardless of whether sham preceded or followed active treatment; NPNS thus appears to have more potential as a treatment than as a cure.

Safety results indicate that NPNS was well-tolerated over the 2-week study duration period.

Both medication-naïve and medication-resistant RLS patients experienced a comparable reduction in RLS severity, as measured by the IRLS and CGI-I. Although medication-naïve patients have the opportunity to choose among several FDA-approved medications, they may be hesitant to do so because of the well-characterized and potentially debilitating side-effects of these medications. The most common option for medication-resistant RLS patients is opioids, which many patients and clinicians are hesitant use due to the highly publicized long-term outcomes associated with misuse, dependency, and addiction. Therefore, NPNS could provide a viable alternative for many patients that are not well managed by the current standard of care.

Study 1 suggests that symptomatic relief may not be immediate but may develop gradually over 30 minutes of NPNS stimulation. Results from each NRS rating scale (Daily, Summary, SIT), indicate that reduction in RLS symptoms is greater after 30 minutes of stimulation than during the initial 30 minutes of stimulation. For the Daily and Summary NRS results, where stimulation lasts 30 minutes, this could be explained by an increase in relief after stimulation is terminated. However, in the SIT procedure, stimulation lasts for 60 minutes, and there is still a trend towards increased relief after 30 minutes. Together, these data point to a gradual physiological mechanism of relief that takes time to develop but that also persists afterwards.

Proper electrode placement may be an important contributor to efficacy. Stimulation electrodes were positioned over the common peroneal nerve, which provides sensory and motor innervation to the lower legs and feet, the regions of the body most commonly associated with subjective RLS symptoms. Without being bound by theory, possible mechanisms of action may include the Gate Control Theory, wherein activation of sensory nerve fibers in the peroneal nerve suppresses pathological neural signals at the level of the spinal cord. In addition, however, the pathological basis of RLS may be located primarily in the brain instead of the spinal cord or peripheral nervous system. Accordingly, NPNS may also operate by transmitting signals through the ascending sensory pathways to suppress pathological neural signals in the thalamus, somatosensory cortex, limbic system, or other brain regions.

Stimulation parameters may also contribute to tolerability and efficacy. Stimulation parameters in Study 1 were designed and calibrated to transmit maximal stimulation intensity while allowing for comfortable self-administration without distracting paresthesias. In contrast, alternative neurostimulation approaches such as spinal cord stimulation or TENS devices induce distracting paresthesias that would likely interfere with sleep onset and thus preclude bedtime usage.

Figure 8A:
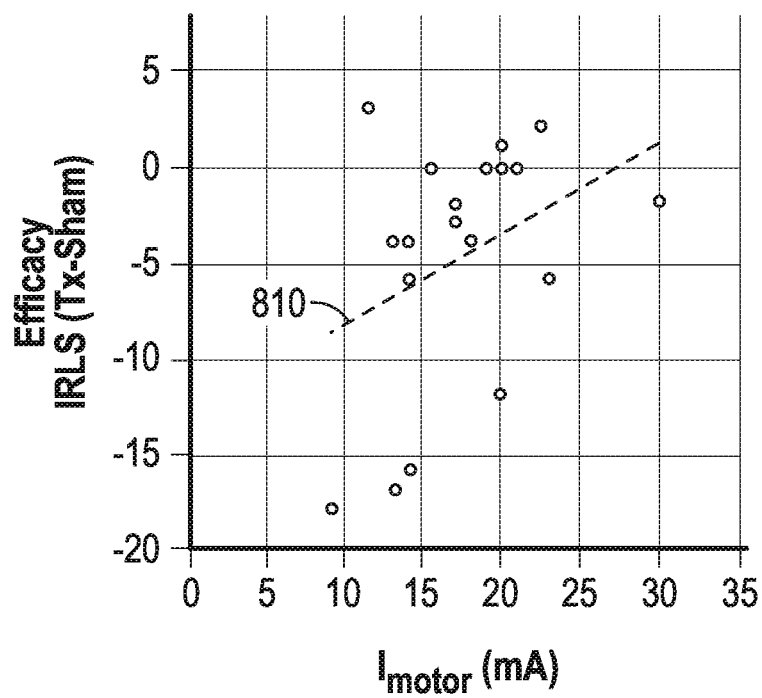
FIGS. 8A and 8B are graphs of NPNS therapy efficacy vs. tonic motor threshold and distraction threshold, respectively.

Applicants also investigated the relationship of efficacy of NPNS in lowering IRLS scores of certain patients compared to sham stimulation. FIG. 8A is a graph of stimulation efficacy for a number of patients as a function of each patient's tonic motor threshold as determined by sEMG measurements. Each point in FIG. 8A represents a patient, and the X-axis value corresponds to the current (mA) value indicative of the patient's tonic motor threshold $I_{motor}$ (i.e., for evoking sustained tonic activity in the tibialis anterior muscle) obtained during the short (approximately 5 minutes) calibration/threshold determination process depicted in FIG. 4 and discussed above. The Y-axis value of each point indicates the reduction of the patient's IRLS score at the end of two weeks of therapy compared to two weeks of sham stimulation. Patients having lower Y-axis values indicate that therapy provided greater improvement over sham stimulation than those with higher Y-axis values (i.e., lower Y-axis values indicate higher therapeutic efficacy). Line 810 is a least-squares fit to the data points, and shows that the lower the patient's tonic motor threshold for evoked tonic activation of the tibialis anterior muscle, the higher the efficacy. As stated above and without being bound by theory, this may be because the peripheral nerves are more sensitive to NPNS delivered via the approach described above, due to properties of the nerve fibers, due to properties of the layers of tissue between the electrodes and the nerve fibers, and/or due to the positioning of the electrodes relative to the nerve. FIG. 8A thus indicates that a short (about 5 minute) calibration process at which the patient's tonic motor threshold is identified can be used in an embodiment to identify patients having a higher likelihood of therapeutic benefit to NPNS. In another embodiment, FIG. 8A indicates the minimum stimulation intensity (e.g., the minimum current value for a fixed pulse width and pulse waveform) to provide a likelihood of therapeutic response—the tonic motor threshold current, $I_{motor}$.

Figure 8B:
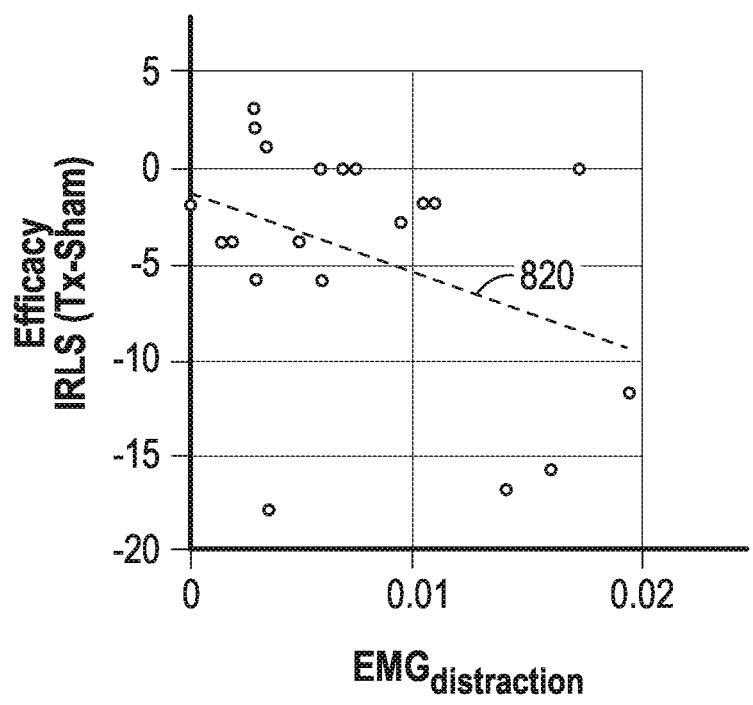

FIG. 8B is a graph of stimulation efficacy as a function of the sEMG activation at the patient's distraction threshold ($EMG_{distration}$), as measured during the period of time indicated by 450 in FIG. 4. As with FIG. 8A, each point in the Figure represents a patient, and the Y-axis value again indicates the reduction in IRLS score at the end of 2 weeks of therapy vs. 2 weeks of sham stimulation. The X-axis in FIG. 8B represents the magnitude of the sEMG activation of the tibialis anterior muscle occurring at the distraction threshold during the brief calibration process of FIG. 4. Line 820 is a least-squares fit to the data points, and demonstrates that the greater a given patient's sEMG activation (i.e., the stronger the tonic activation in the tibialis anterior muscle for stimulation at the distraction threshold (i.e., the therapeutic setting), the more likely the patient is to experience greater efficacy (i.e., greater IRLS reduction for therapy vs sham stimulation). Since the FIG. 8B represents activity at the distraction threshold (the highest stimulation settings likely usable for treating a patient during sleep), it suggests that the greater the tonic activity that can be induced by the electrostimulation therapy signal, the greater the likely efficacy.

Figure 9:
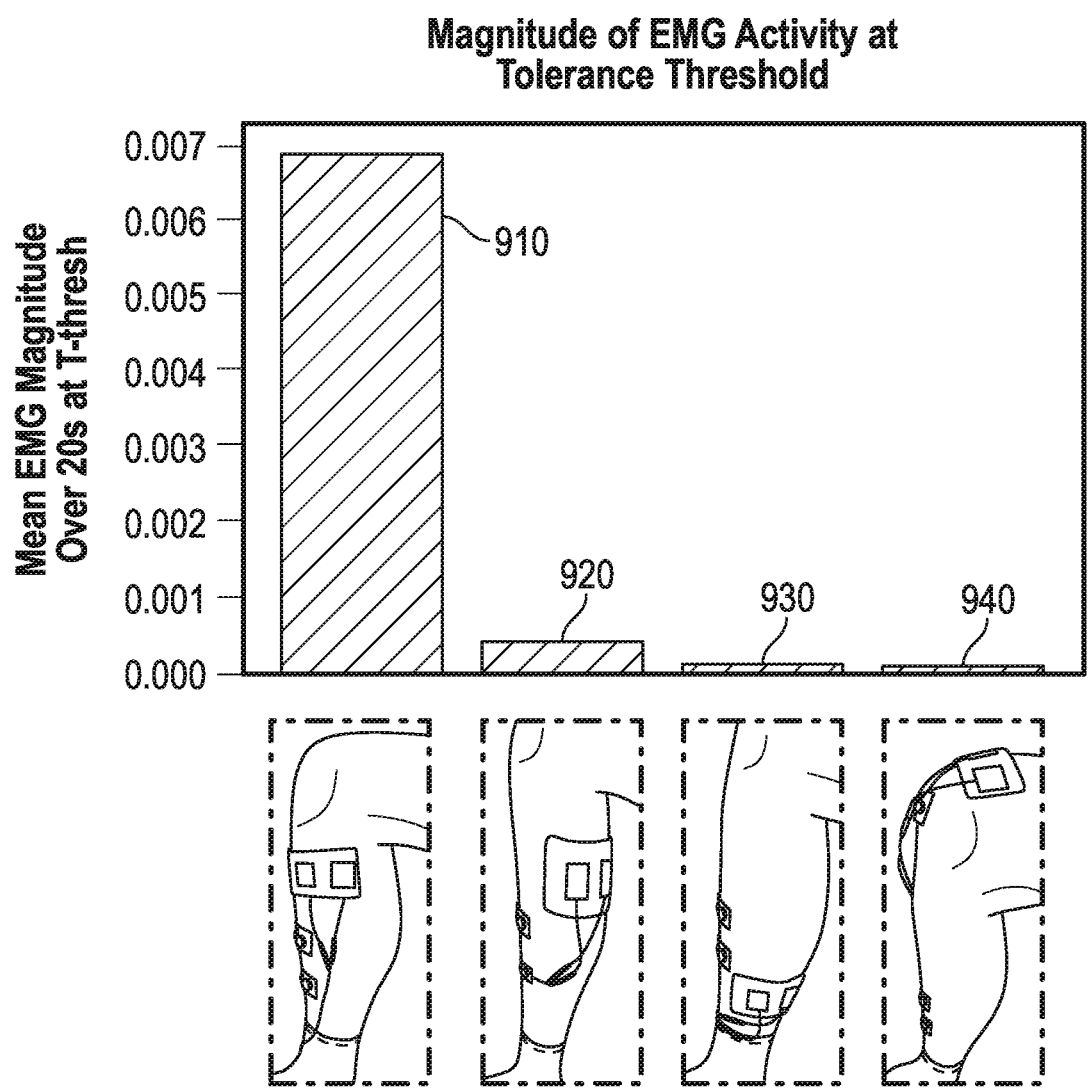
FIG. 9 is an illustration of evoked sEMG responses to an electrostimulation test signal for various electrode placement locations.

FIG. 9 illustrates how sEMG response to an electrostimulation test signal can be used to identify when a wearable patch (e.g., patch 120, FIG. 1) is correctly positioned. As shown by the four different photographs, each involving a different patch (and therefore hydrogel electrode) position relative to the target nerve, a test signal when applied to the nerve will evoke a significantly higher sEMG response (910) when the electrodes are innervating the target nerve (a superficial peroneal nerve in FIG. 9) as compared to other positions in which the electrodes are remote or not proximal to the target nerve (920, 930, and 940). In general, the more remote the electrode placement from the target nerve, the lower the evoked sEMG response for the innervated muscle, except that the evoked response substantially increases when the electrode is proximal to the target nerve. Accordingly, an embodiment comprises methods to ensure proper placement of a wearable electrode patch for the treatment of RLS or PLMD symptoms using evoked responses to electrostimulation test signals applied to the electrodes on the electrode patch.

Patients using the present systems may be sensitive to very minor discomforts in view of the sensory hypersensitivity sometimes associated with RLS and PLMD. Accordingly, many patients will not use systems they perceive as uncomfortable. It is desirable to make the stimulator unit containing the system electronics and software/firmware and wearable patch as small, light, and non-bulky as possible. Because of the need for a reduced size, in some designs the power supply and circuit board confined in a small space and operating to provide high-frequency electrical pulses can create the potential for heating issues within the stimulation unit. If the temperature rises significantly above patient body temperature, the discomfort may lead the patient to discontinue use. Because small power supplies and circuit boards may be necessary, for patients requiring high power usage (e.g., higher frequencies or relatively high-current pulses in the case of patients with high tonic motor or distraction thresholds), some embodiments can comprise systems and methods in which one or more parameters of the system are monitored, and one or more stimulation parameters may be changed such as to optimize one or more goals in addition to or in combination with therapeutic efficacy (e.g., power usage).

In an embodiment, the system may monitor one or more system and/or efficacy parameters, which may be used as feedback to adjust one or more electrostimulation parameters, or start, stop, or resume therapy to achieve one or more goals. As nonlimiting examples, the system may monitor power usage or remaining power available, the highest temperature within the system (e.g., in a pulse generator or processor), the impedance of the patient's body tissue (which may indicate that the hydrogel electrodes are degrading, are experiencing a buildup of skin cells creating increased impedance, or other issues suggesting a need to replace the wearable patch). As a nonlimiting example, the system may monitor or calculate one or more system or body parameters that correlate with therapeutic efficacy such as: patient movement (e.g., calculated from a three-dimensional accelerometer during sleep or during/after therapy, for short or long timescales); sEMG activity indicative of the level of muscle activation (including changes in muscle activation over time that may indicate increasing or decreasing efficacy or neural accommodation) or how far above or below the tonic motor threshold the electrostimulation therapy stimulation is causing in the tibialis anterior or another muscle; patient feedback such as a signal from the patient (e.g., by manual or wireless input) indicating that the stimulation is above or below a target threshold such as a sensory threshold, a tonic motor threshold, a distraction threshold, a tolerability threshold, or a pain threshold.

One or more of the foregoing system and/or efficacy parameters may be used as inputs to one or more system processors and/or algorithms such as to change one or more operational parameters to achieve one or more goals such as, without limitation: avoiding neural accommodation or tolerance, ensuring adequate power for a planned or in-process therapy protocol, compensate for high impedance, reduce temperature, and avoid patient discomfort. In an embodiment, one or more parameters of the electrostimulation therapy signal may be adjusted randomly or pseudo-randomly or at programmed time interval to provide different electrical signals that remain consistently at or near the distraction threshold such as to avoid neural accommodation. In an embodiment, accommodation may be avoided by recurrently or periodically changing one or more of the electrostimulation therapy parameters such as to alternate between signals at or slightly above the tonic motor threshold (and below the distraction threshold) and signals at or near the distraction threshold. In a still further embodiment, the electrostimulation parameters may be recurrently or periodically changed by providing stimulation for short durations (e.g., 5 or 10 seconds, above the distraction threshold but below the tolerability threshold. In an embodiment, the calibration process of FIG. 4 may be recurrently or periodically repeated (e.g., every month) or on the occurrence of certain events (e.g., a decrease in efficacy) such as to help re-establish optimum electrostimulation therapy parameters.

In an embodiment, one or more electrostimulation therapy parameters may be changed (e.g., by temporarily or recurrently or periodically reducing and then restoring programmed current or pulse width) such as to help ensure adequate power for stimulation throughout the night for a patient with severe RLS symptoms, based on projected power usage. In an embodiment, an indication of high temperature within the system may be used to reduce pulse current, pulse width, or pulse frequency, or to disable stimulation for a predetermined time period, or to provide a longer ramping time.

In an embodiment, patient input (e.g., from a patient app on a personal computing device) may be used to change one or more electrostimulation therapy (e.g., to increase or decrease stimulation intensity), to respond to recurrent or periodic prompts (e.g., to provide an RLS symptom score), or to log patient comments on the operation or use of the system and the efficacy of therapy. Although such implementations may be complex and time-consuming, persons of skill in the art may be able to implement the foregoing functions and/or structures with the benefit of the present disclosure and the related applications previously noted.

In an embodiment, the present systems and methods can include treating a patient having symptoms associated with RLS or PLMD using a first high-frequency pulsed electrostimulation therapy signal applied to a first neural target on a leg of a patient, and a second high-frequency pulsed electrostimulation therapy signal applied to a second neural target on an arm of a patient, wherein the first and second high-frequency electrostimulation therapy signals are above a tonic motor threshold of a muscle innervated by the first and second neural targets, respectively.

Disorders of Hyperexcitable Nerves:

To recap and expand upon the above description, there exist certain conditions that can cause hyperexcitability of one or more nerves, such as can lead to one or more painful or uncomfortable sensations such as can significantly disrupt quality of life in patients. Examples can include Restless Legs Syndrome (RLS), nocturnal muscle cramps, hyperexcitability of the bladder (Overactive bladder or OAB), muscle cramps, dystonia, tension headaches, itching, sciatica, temporomandibular joint disorder (TMJ), chronic pain, Parkinson's disease, or Huntington's disease. The present approaches of personalizing electrostimulation therapy delivered to the patient using a consistently repeatable paradigm (such as can include using a surface EMG signal) can help improve therapeutic efficacy, and can additionally or alternatively help allow for reducing or minimizing the amount of electrical charge delivered to the patient, thereby increasing power efficiency and hence battery longevity, reducing heat dissipation, or the like.

Restless Legs Syndrome (RLS)

Restless legs syndrome (RLS), also called Willis-Ekbom disease (WED), is a common sleep-related movement disorder characterized by an often unpleasant or uncomfortable urge to move the legs that can occur during periods of inactivity, particularly in the evenings, and is transiently relieved by movement. Current treatments for RLS predominantly include pharmaceutical therapies-ranging from dopamine supplementation (levodopa), dopamine agents (ropinirole, pramiprexole), and anti-convulsants like gabapentin, in certain cases. Other treatment approaches can include using a mechanical vibration pad, which may not be efficacious beyond as a placebo.

Hyperactive nerve activity in the peripheral nervous system and/or spinal cord is thought to contribute to the pathophysiology of RLS. Voluntary leg movements naturally lead to reduction in RLS symptoms, such as may be explainable through the Gate Control Theory mechanism, wherein proprioceptive signals triggered by leg movements suppress pathological hyperactive nerve signals before they reach the brain. However, voluntary leg movements are incompatible with sleep. Systems such as vibrating mattress pads or TENS or NEMS devices can generate similar signals to voluntary leg movements, but can also generate a similar distraction that can be incompatible with sleep.

Figure 10A:
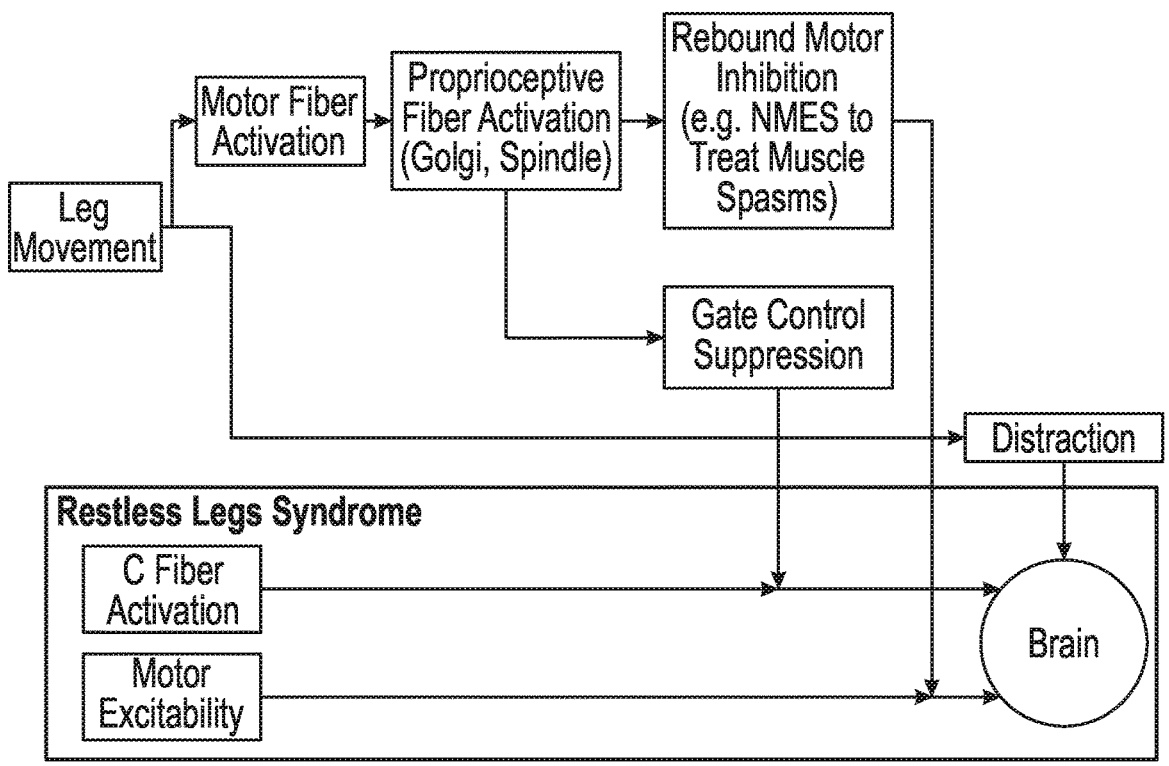
FIG. 10A is an illustration of a conceptual model of RLS and the role of leg movements.
Figure 10B:
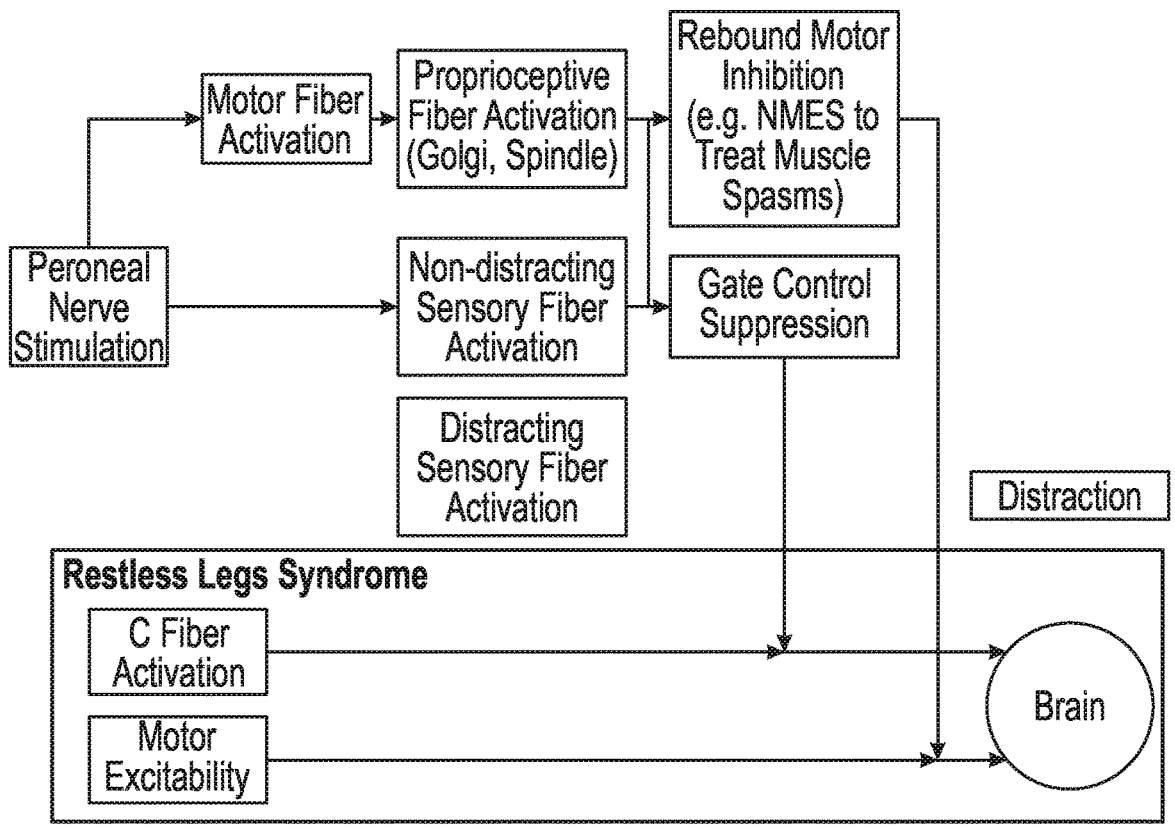
FIG. 10B is an illustration of a conceptual model of RLS and the role of electrostimulation of the peroneal nerve in helping avoid leg movements.

Shriram Raghunathan U.S. Pat. No. 10,342,977 entitled Restless Leg Syndrome or Overactive Nerve treatment, which issued on Jul. 19, 2019, and which is incorporated herein by reference, describes a technique to treat an RLS symptom to provide therapeutic benefit, such as without distracting side-effects. For example, U.S. Pat. No. 10,342,977 describes an approach that can employ one or more high-frequency electrostimulation waveforms that can potentially differentially affect different nerve fiber types, thus allowing patients to tolerate higher and more therapeutically effective levels of electrical nerve stimulation without disrupting the patient's ability to fall asleep naturally. For example, activating one or more nerve fibers of the peroneal nerve allows for excitation of sensory and proprioceptive nerve fibers leading to a gate-control suppression of the peripheral and/or spinal hyperexcitability in RLS patients and thus a reduction in the sensation of an urge to move their legs. Without being bound by theory, FIGS. 10A and 10B illustrate conceptually an example of this difference between how voluntary leg movements can relieve RLS symptoms (see FIG. 10A) such as by a gate control suppression and/or a distraction mechanism, and how treatment via high-frequency electrostimulation of the common peroneal nerve (FIG. 10B) can help suppress RLS symptoms such as leg movement, thereby allowing better sleep onset and sleep quality.

The present inventors have observed, among other things, that electrical nerve stimulation waveforms that produce larger involuntary motor fiber activation at rest (e.g., as recorded by surface electromyographic or sEMG activity) were associated with greater therapeutic efficacy, when elicited using one or more therapeutic waveforms that were below a "distraction threshold" such that the patient is allowed to fall asleep comfortably. The distraction threshold can be determined by asking the subject about their tolerance or comfort with a particular waveform. Further, the present inventors have observed that the electrical nerve stimulation frequencies and pulse widths used to elicit this motor response can vary from patient to patient.

Figure 11:
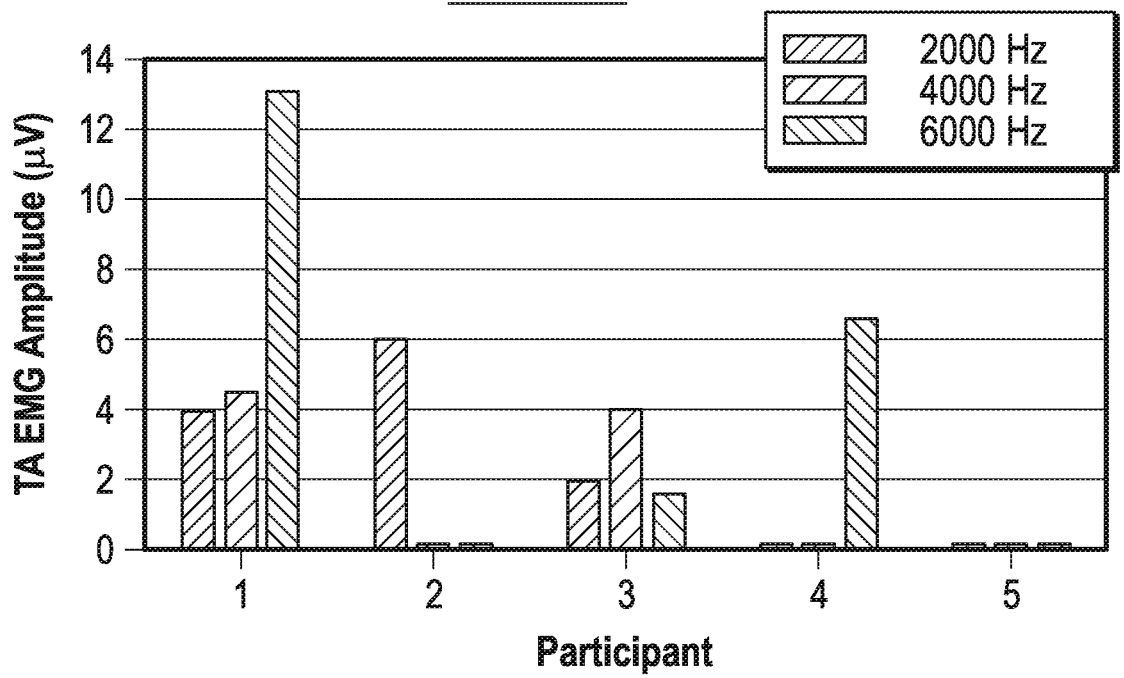
FIG. 11 is an experimentally-obtained graph of EMG amplitude for different electrical nerve stimulation frequencies for five different human subject participants, from a different study than that shown in FIGS. 1-9.

FIG. 11 below is an experimentally-obtained graph of EMG amplitude for different electrical nerve stimulation frequencies (2000 Hz, 4000 Hz, 6000 Hz) for five different human subject participants, from a different study than that shown in FIGS. 1-9. FIG. 11 illustrates an example of the maximal levels of motor activation produced below the distraction threshold by electrical nerve stimulation waveforms varying in frequency (2000 Hz, 4000 Hz, 6000 Hz) across five research participants. Participants 1-4 exhibited motor activation whereas participant 5 did not. Therefore, participant 5 may not be a suitable candidate for during-sleep therapy and can be excluded (e.g., as a "non-responder") during patient screening, such as can be based on surface EMG signal in response to electrostimulation at different frequencies, as an illustrative example of electrostimulation parameter variation. Participants 1, 2, 3, and 4 all showed substantially higher motor activation for a specific frequency, but this "optimal" frequency varied between participants. The optimal frequency was 6000 Hz for Participants 1 and 4, 4000 Hz for Participant 3, and 2000 Hz for Participant 2.

Whereas most RLS patients experience the strongest RLS symptoms while attempting to go to sleep at night, many RLS patients experience symptoms during the daytime, especially during the evenings. Moreover, many other conditions associated with hyperactive nerve activity are more or most prominent during the day. Therefore, we also used surface EMG signal activity to clinically evaluate the relative efficacy of electrical neurostimulation waveforms at a higher, daytime-relevant patient threshold, that is, the patient's "discomfort threshold". For all participants, the patient's "distraction threshold" for being able to fall asleep was lower than the same patient's "discomfort threshold" for being willing to tolerate electrical neurostimulation therapy while awake such as when conducting one or more ordinary activities of daily life. We observed a similar differentiation of EMG signals in response to different frequencies of electrical nerve stimulation at the patient's discomfort threshold, indicating that this approach of using a surface EMG signal as an indication of electrical neurostimulation response efficacy or efficiency or the like can also be useful, such as for selecting or adjusting titration of daytime electrical neurostimulation.

Figure 12:
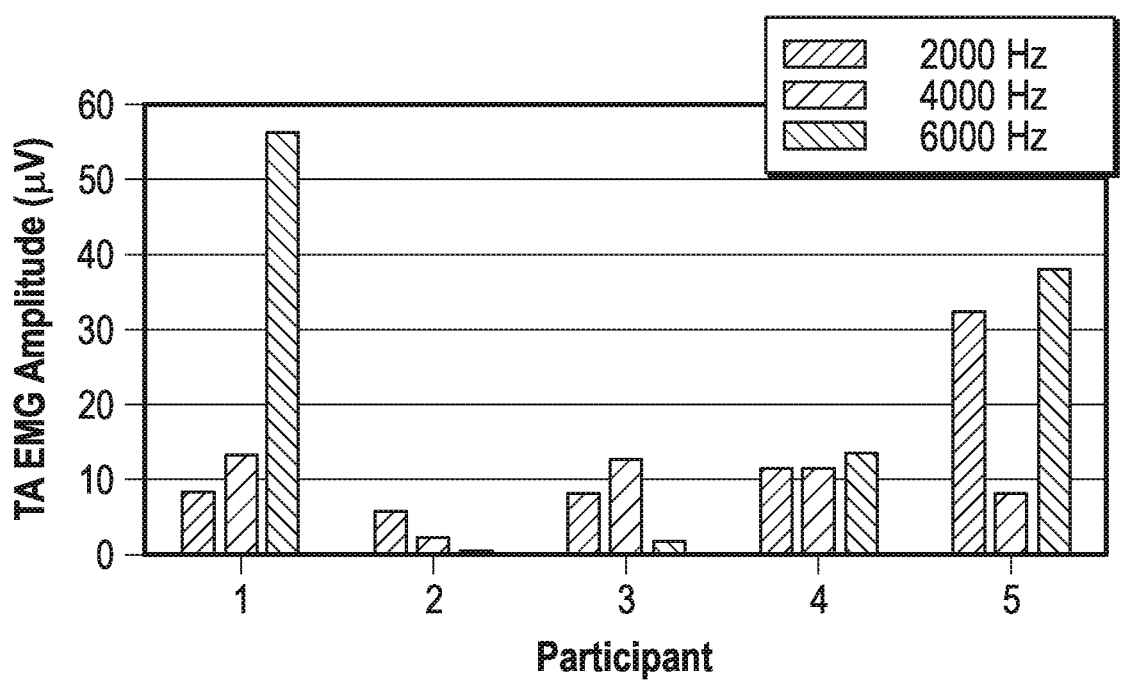
FIG. 12 is an experimentally-obtained graph of surface EMG amplitude in response to varying an electrostimulation parameter, here, providing different electrical nerve stimulation frequencies for five different human subject participants, across the same five research participants as were studied for the results shown in FIG. 11, i.e., from a different study than that shown in FIGS. 1-9.

FIG. 12 is an experimentally-obtained graph of surface EMG amplitude in response to varying an electrostimulation parameter, here, providing different electrical nerve stimulation frequencies (2000 Hz, 4000 Hz, 6000 Hz) for five different human subject participants. FIG. 12 below illustrates the surface-EMG-determined maximal levels of motor activation produced below the patient's discomfort threshold by applying electrostimulation waveforms varying in a selected parameter, here, frequency (2000 Hz, 4000 Hz, 6000 Hz) across the same five research participants as were studied for the results shown in FIG. 11. Participants 1-5 all exhibited motor activation. Therefore, based on these EMG signal responses to varying neurostimulation results, patient screening would result in all participants being deemed to be suitable candidates for daytime electrostimulation therapy. Based on surface-EMG signal based differential motor activation between different electrical nerve stimulation frequencies, participant 1 would be assigned to an electrostimulation frequency of 6000 Hz, participant 2 would be assigned to 2000 Hz, participant 3 would be assigned to 4000 Hz, participant 4 could be assigned to any of the three electrostimulation frequencies, such as can be selected depending on relative power constraints, and participant 5 could be assigned to 2000 or 6000 Hz, such as depending on relative power constraints.

As shown by the experimental results in FIG. 12, Participants 1-4 all exhibited surface EMG signal determined motor activation below the patient's distraction threshold, but only Participants 1 and 3 exhibited motor activation at multiple electrostimulation frequencies below the corresponding patient's distraction threshold. Therefore, relative power consumption may be used as a consideration or goal, such as in terms of deciding which electrostimulation frequency to deliver for participants 1 and 3. Alternatively, the amplitude of sEMG activation at the distraction threshold could be used as a consideration or goal, as discussed in the description of FIG. 8B.

Figure 13:
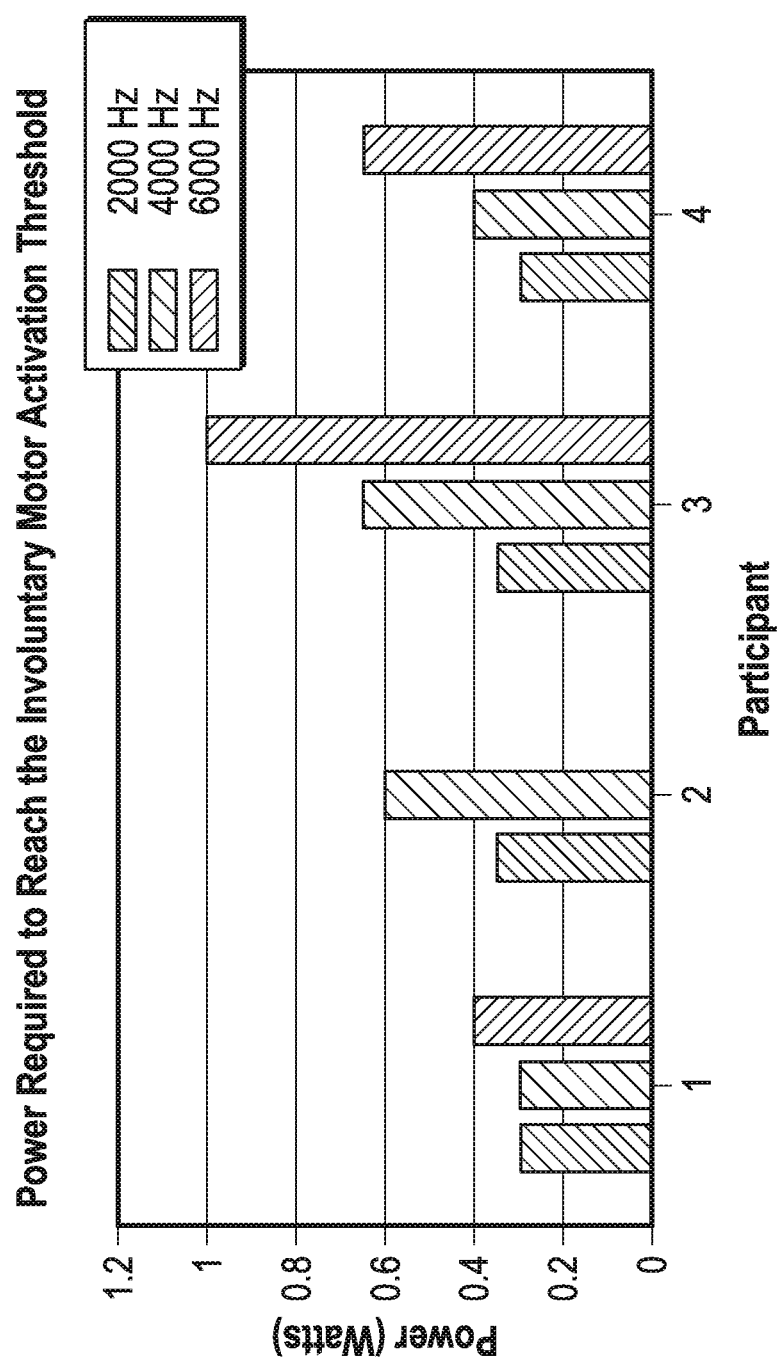
FIG. 13 shows experimental data illustrating the electrical nerve stimulation power to reach surface EMG motor activation for each participant.

FIG. 13 shows experimental data illustrating the electrical nerve stimulation power to reach surface EMG motor activation for each participant. For participant 1, the differences in electrostimulation power are not substantially different across the different electrostimulation frequencies. For participant 3, the lower electrostimulation power needed at an electrostimulation frequency of 2000 Hz relative to that needed at an electrostimulation frequency of 4000 Hz can be used as a basis to automatically select or otherwise choose 2000 Hz as the electrical nerve stimulation frequency.

Example of a Personalization Method

In an illustrative example, one or more recording electrodes for sEMG can be placed at a desired location, such as close to the belly or the thickest part of the muscle innervated by a specific nerve being electrically stimulated. In the case of treating RLS, such as described in U.S. Pat. No. 10,342,977, two sEMG recording electrodes can be located on the belly of the tibialis anterior (TA) muscle on the leg being stimulated, one sEMG reference electrode can be placed on the kneecap, and the two electrical nerve stimulation electrodes can be placed along the length of the common peroneal nerve on the lateral side of the leg, covering the head of the fibula, below the kneecap.

Surface electromyographic activity (sEMG) can be recorded from the belly of the TA muscle, such as can be sampled at a frequency that is below the frequency of electrical nerve stimulation (e.g., sampled at 512 Hz for the experiment described above in which the electrical nerve stimulation is at electrostimulation frequencies of 2000 Hz, 4000 Hz, and 6000 Hz). The resulting recorded sEMG waveform can be signal processed, for example, it can be amplified, bandpass filtered such as between 1 Hz-512 Hz, rectified, smoothed such as using a rolling averaging, filtering, or other smoothing time window of between 1 second and 5 seconds, inclusive, and monitored.

In an illustrative example—such as for helping ensure maximal electrical neurostimulation efficacy for "during-sleep" usage—for each electrical nerve stimulation setting (e.g., with one or more parameters that can include pulsewidth, inter-pulse-interval, or the like), the amplitude of the electrical nerve stimulation waveform can gradually be ramped up, such as until it reaches the patient's "distraction threshold" at which the subject reports that the electrical nerve stimulation is too distracting to allow the patient to sleep.

In another illustrative example—such as for helping ensure maximal efficacy for daytime electrical nerve stimulation—for each electrical nerve stimulation setting (e.g., with one or more parameters that can include pulsewidth, inter-pulse-interval, or the like), the amplitude of the electrical nerve stimulation waveform can gradually be ramped up, such as until it reaches the patient's "discomfort threshold" at which the subject reports not being able to comfortably tolerate the electrical nerve stimulation.

In another illustrative example—such as for helping reduce power, voltage, or current of the electrical nerve stimulation—for each stimulation setting (e.g., with one or more parameters that can include pulsewidth, inter-pulse-interval, or the like), the amplitude of the electrical nerve stimulation waveform can gradually be ramped up, such as until the rectified EMG signal is observed to consistently exceed the EMG signal at baseline (before applying the electrical nerve stimulation) by a specified factor (such as of 2×) over a specified time period (such as of 15 seconds).

In one or more of these above illustrative examples, the electrical nerve stimulation parameter(s) setting can be recorded by the system and the next set of electrical nerve stimulation parameters in an aggregate list of such sets can be used to repeat this process, such as to explore various permutations or combinations of the electrical nerve stimulation parameter(s) settings.

For the time period corresponding to this electrical nerve stimulation parameter exploration process, the patient can be instructed to maintain at rest to avoid voluntary muscle activation. The EMG system can be configured to provide an algorithm or other means to detect one or more high levels of voluntary muscle activation via the sEMG signal and, in any such instances, to signal to the patient or to a clinician or technician to re-start the stimulation parameter exploration procedure. This algorithm can also "ingest" or store the raw EMG signal that has been amplified and bandpass filtered between 1 Hz-512 Hz, but that has neither been rectified nor smoothed.

A first potential goal of the electrical nerve stimulation parameter exploration can be to find the electrical nerve stimulation waveform setting that produces the maximal increase in the resting sEMG signal (e.g., from a pre-stimulation baseline value) while remaining below the patient's distraction (or discomfort) threshold. This particular selected electrical nerve stimulation waveform can then be programmed into the electrical nerve stimulation therapy device and deemed to represent the most efficacious electrical nerve stimulation waveform to be delivered for that specific patient.

A second potential (additional or alternative) goal of the electrical nerve stimulation parameter exploration can be to find the most power (or current or voltage)-efficient stimulation waveform setting that produces a clinically relevant increase (from baseline) in the resting sEMG signal while remaining below the patient's distraction (or discomfort) threshold. This selected electrical nerve stimulation waveform can then be programmed into the therapy device and can help provide the most power-efficient therapeutic electrical nerve stimulation waveform to deliver for that specific patient. Power efficiency also can result in less heat generation by the device, which, in turn, can help make use of the device more comfortable to the patient.

A third potential (additional or alternative) goal of this the electrical nerve stimulation parameter exploration can be for patient screening, such as to help identify one or more "non-responder" patients that do not show a clinically relevant increase in the resting sEMG signal while remaining below the distraction (or discomfort) threshold, and excluding them from eligibility in a clinical trial or from being prescribed such an electrical nerve stimulation device.

In the testing example shown in FIG. 14, one or more of the electrical nerve stimulation waveform parameters can be selected or varied, such as using a Table of possible permutations or combinations of variations of one or more of pulsewidth (PW) and inter-pulse-interval (used to derive frequency f), such as shown below in illustrative example of FIG. 15.

Figure 15:
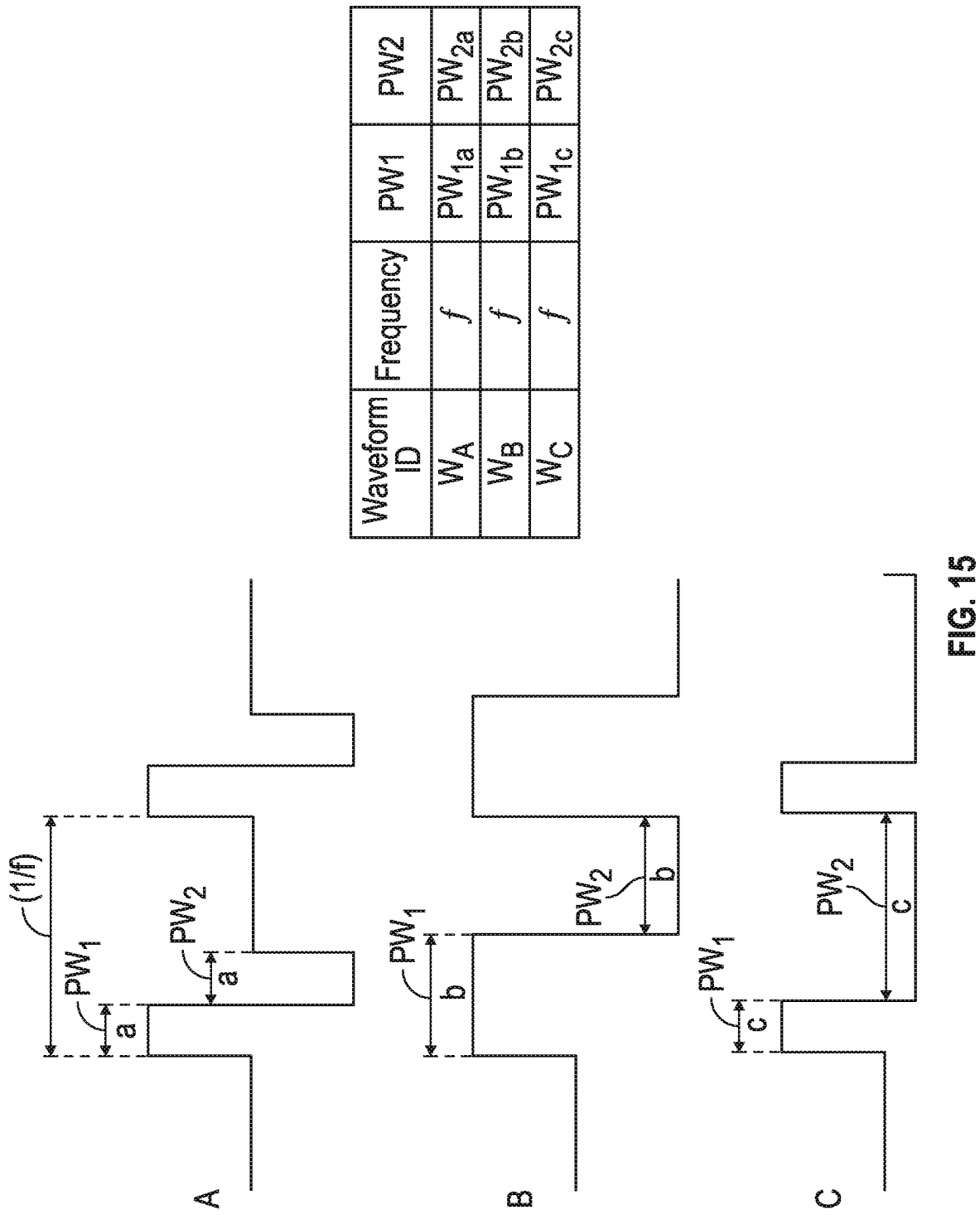
FIG. 15 illustrates possible electrical nerve stimulation waveforms with some differing parameter settings.

In FIG. 15, electrical nerve stimulation waveforms A through C illustrate three different electrical nerve stimulation waveform permutations that represent charge-balanced electrical nerve stimulation settings with differing stimulation pulse widths (PW) all at the same stimulation frequency (f) in the illustrated example, all this is not required. In sweeping through these different electrical nerve stimulation waveform settings, the present testing method can aim to identify the optimal waveform for a particular specified single or composite goal, e.g., that minimizes charge injected, maximizes sEMG activation, or such as does one or both of these things while being one or both of comfortable to the patient or not distracting to the patient.

Figure 14:
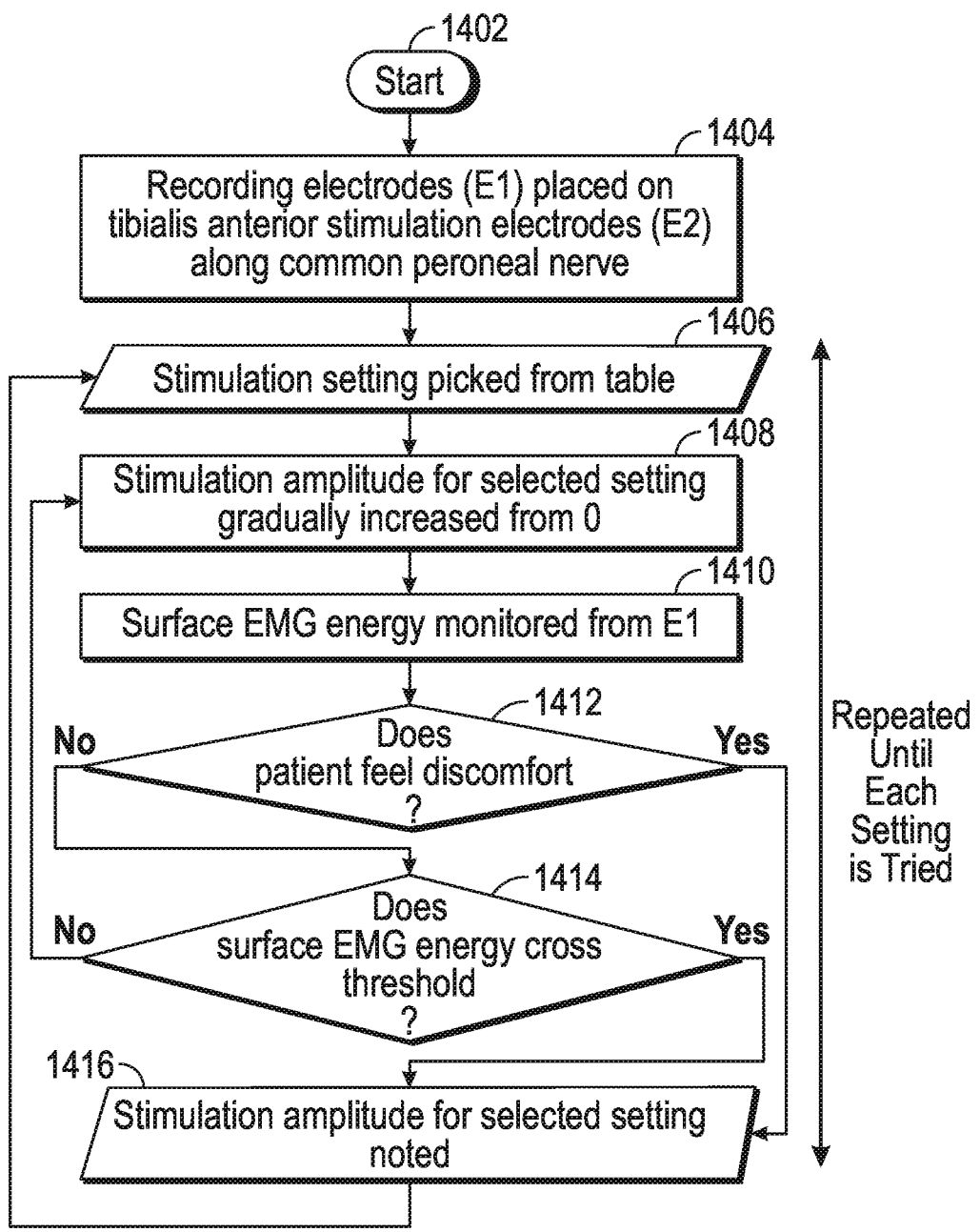
FIG. 14 shows an example of a technique for testing various stimulation parameter settings and monitoring surface EMG responses.

In FIG. 14, at 1402, testing of various electrical nerve stimulation parameters can start. At 1404, recording electrodes (E1) can be placed on a desired location on the surface of the patient's anatomy, such as on the tibialis anterior. Stimulation electrodes (E2) can be placed on a desired location on the surface of the patient's anatomy, such as over and along the patient's common peroneal nerve.

At 1406, a neurostimulation setting (e.g., a combination of neurostimulation parameters) can be selected, such as from a stored table, in memory circuitry, such as can include various neurostimulation settings, e.g., in different permutations or combinations of neurostimulation parameters.

At 1408, stimulation at a selected neurostimulation setting can commence, such as by gradually ramping neurostimulation amplitude up to a specified amplitude level.

At 1410, surface EMG signal response to the neurostimulation can be monitored from the recording electrodes (E1).

At 1412, the patient can be monitored or queried (e.g., via a patient interface device) to determine whether the patient feels discomfort resulting from the neurostimulation. If so, then process flow can proceed to 1416, otherwise process flow can proceed to 1414.

At 1414, the surface EMG signal can be signal-processed and monitored and compared to a threshold value, such as to determine whether an indication derived from the surface EMG signal crosses a threshold value. If so, then process flow can proceed to 1416, otherwise process flow can proceed to 1408 to continue gradually increasing stimulation amplitude.

At 1416, the stimulation setting at which discomfort is indicated can be recorded and stored in memory circuitry. The stimulation setting at which the surface EMG signal indication crossed the threshold value can also be recorded at this step of the process flow. Then, process flow can return to 1406, such as to select another neurostimulation setting, e.g., involving a different set of neurostimulation parameters. In this manner, the various neurostimulation settings stored in the table can be tested in a sequential manner. A linear progression through the Table may be used, otherwise a binary search or other rules-based or other technique of determining a logical next neurostimulation setting to be tested can be employed.

Applicability of Technique to One or More Other Indications

While the example above focuses on optimizing one or more electrostimulation waveforms such as to treat one or more symptoms of Restless Legs Syndrome (RLS), a similar approach can be used to optimize one or more electrostimulation therapies for one or more other indications, such as by targeting a different nerve-muscle combination. Some examples are included below in Table 1.

TABLE 1

EXAMPLES OF OTHER INDICATIONS WITH SAMPLE TARGET NERVE AND MUSCLE

| Disorder example | Electrostimulation Nerve target example | Muscle target example for obtaining EMT response |
| --- | --- | --- |
| RLS | Sciatic nerve and/or one or more branches of the sciatic nerve (e.g., peroneal, sural, or tibial) | Muscle of thigh, leg, or foot (e.g., one or more of tibialis anterior, gastrocnemius, soleus, biceps femoris, or quadriceps) |
| Tension headache | Trigeminal nerve | Temporalis |
| Focal dystonia (primary or secondary to PD) | Nerve innervating affected muscle | Affected muscle |
| Temporomandibular joint disorder (TMD/TMJ) | Trigeminal nerve | Muscle of mastication (e.g., one or more of masseter, pterycgoid, or trigeminal) |
| Teeth grinding during sleep | Trigeminal nerve | Muscle of mastication (e.g., one or more of masseter, pterycgoid, or trigeminal) |
| Tremor | Nerve innervating affected muscle | Affected muscle |
| Muscle spasms | Nerve innervating affected muscle | Affected muscle |
| Muscle cramps | Nerve innervating affected muscle | Affected muscle |

TABLE 1-continued

EXAMPLES OF OTHER INDICATIONS WITH SAMPLE TARGET NERVE AND MUSCLE

| Disorder example | Electrostimulation Nerve target example | Muscle target example for obtaining EMT response |
|---|---|---|
| Huntington's Disease chorea | Nerve innervating affected muscle | Affected muscle |
| Overactive bladder | Nerve innervating detrusor muscle | Detrusor muscle |
| Sciatica | Sciatic nerve and/or one or more branches of the sciatic nerve (e.g., peroneal, sural, or tibial) | Muscle of thigh, leg, or foot (e.g., one or more of tibialis anterior, gastrocnemius, soleus, biceps femoris, or quadriceps) |

Applicability of Technique to One Or More Other Nerve Stimulation Approaches Such as to Reduce One or More Side-Effects Although Table 1, above, focuses on electrical nerve stimulation to treat various conditions that are associated with hyperactive muscles, there are additional electrical nerve stimulation techniques for which the described testing method can be useful.

In such a context, the present testing method can be used to select or optimize one or more neurostimulation techniques that can have the unintended side-effects of activating one or more muscles. For example, vagus nerve stimulation to treat epilepsy can result in activation of the pharyngeal muscles, because these muscles are innervated by branches of the vagus nerve.

In an example, such as in which the muscle activation is correlated with the therapeutic effect, the present technique can be used to identify one or more stimulation parameter settings that result in more activation of the muscle (e.g., while remaining below a patient discomfort or patient distraction threshold) and thus a higher therapeutic efficacy.

In another example, such as in which the muscle activation is an unwanted side-effect, the present technique can be used to identify one or more therapeutic stimulation parameter settings that minimize or reduce such an unwanted side-effect.

Automated Device and System for Waveform Personalization

Figure 16:
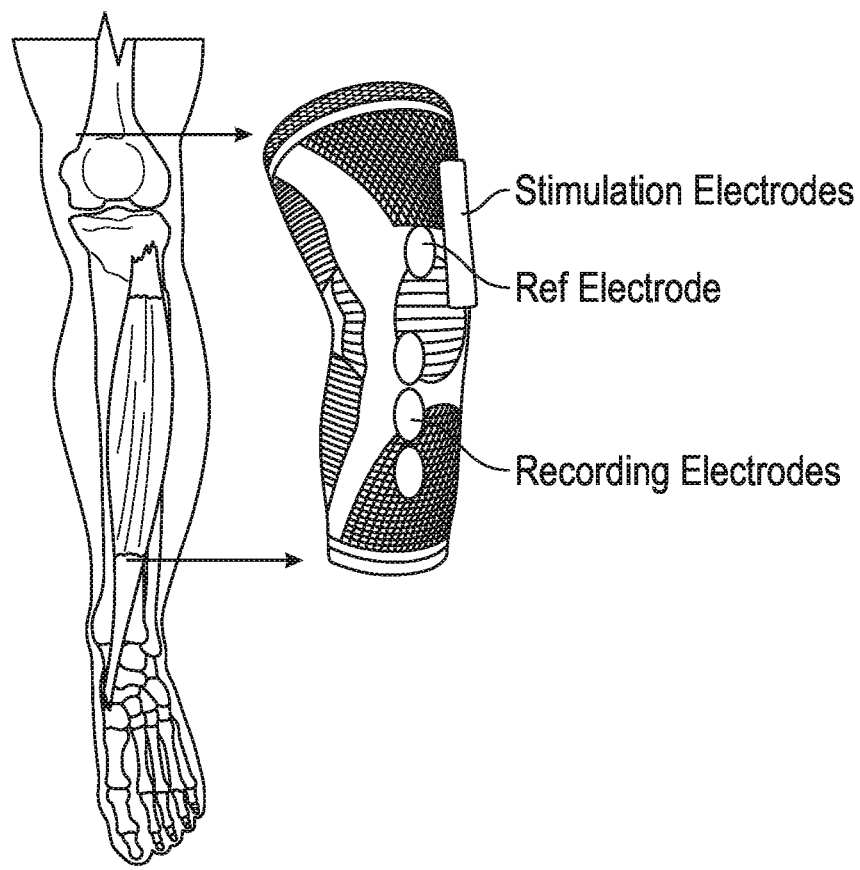
FIG. 16 shows an example of a leg-worn sleeve device that can include EMG monitoring electrodes and electrical nerve stimulation electrodes.

In an application of an example of the present technique for optimizing electrostimulation therapy such as to treat RLS, a leg-worn sleeve device can include built-in EMG monitoring electrodes that can be positioned to be located over the tibialis anterior (TA) muscle when worn, and an electrode grid with multiple electrical nerve stimulation electrodes that cover a portion along the length of the common peroneal nerve, such as shown in the example of FIG. 16. The sleeve can also include battery-powered electronic circuitry, such as can be configured to wirelessly communicate with an external computing or display device such as may be used in conjunction with the sleeve to provide signal processing or user interface capability.

Figure 17:
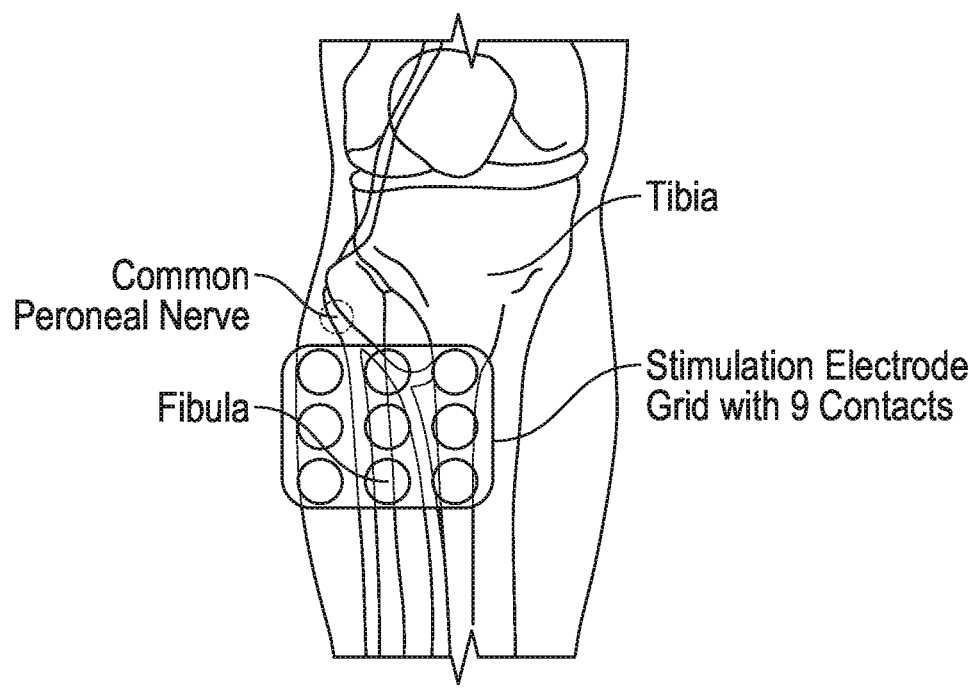
FIG. 17 shows an illustrative example of an electrical nerve stimulation electrode grid.

FIG. 17 shows an illustrative example of an electrical nerve stimulation electrode grid, e.g., of nine electrodes, such as can be placed externally on the patient's skin such as at a location above and near the patient's common peroneal nerve.

Once the desired electrical nerve stimulation waveform has been identified, the electrical nerve stimulation electrode grid can be used to vary the electrode(s) selected, such as to allow automatic selection of the most effective pair of stimulating electrodes, e.g., that produce a maximal sEMG signal to the electrostimulation using the selected electrical nerve stimulation waveform. Similarly, the on-board electronic circuitry may additionally or alternatively be used to help determine the optimal pair of electrical nerve stimulation electrodes such as by detecting the locations of skin contact that present the lowest electrical impedance.

Figure 18:
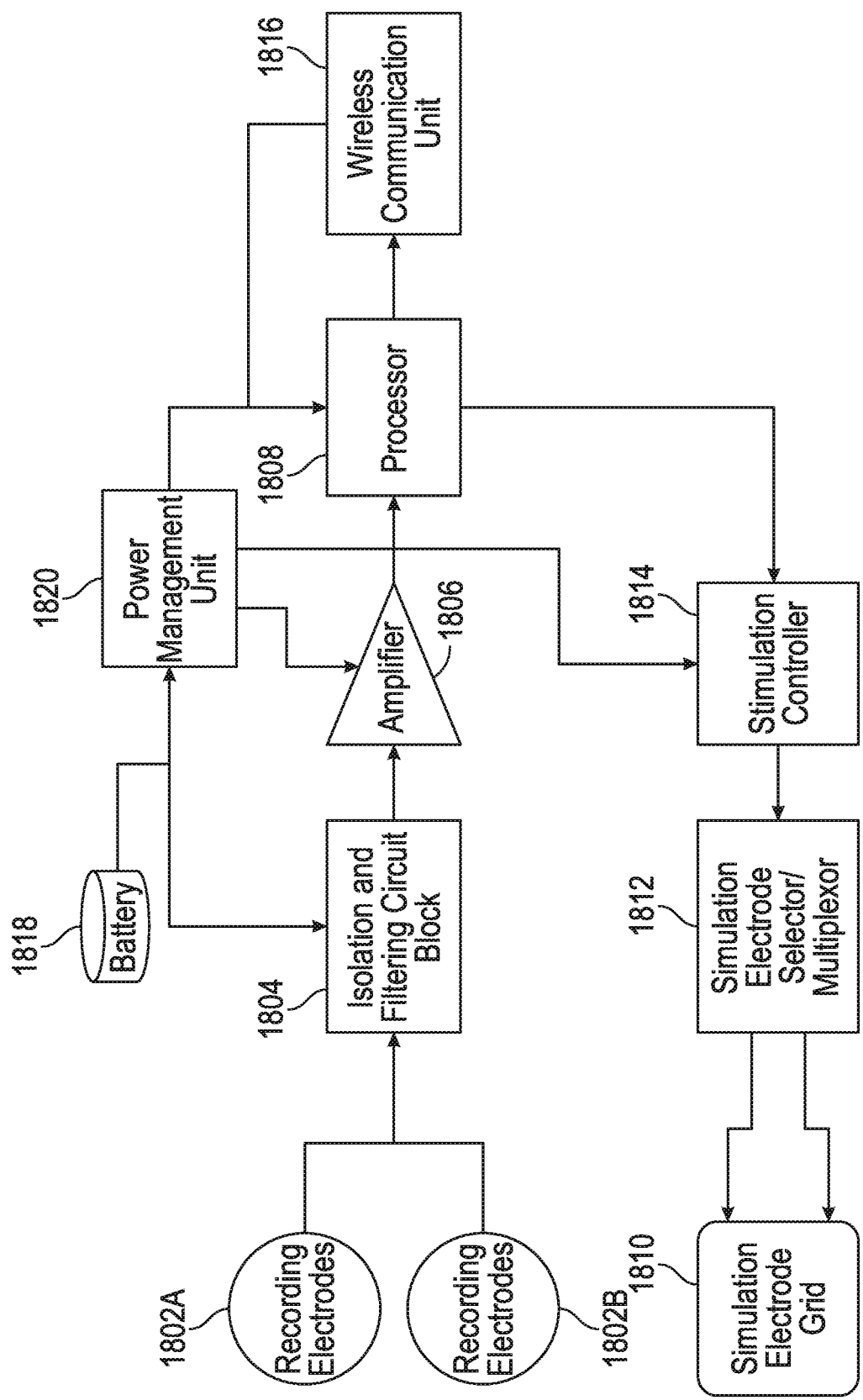
FIG. 18 shows an example of an architecture of the on-board electronic circuitry that can be used to help implement or perform some of the disclosed techniques or methods.

FIG. 18 shows an example of an architecture of the on-board electronic circuitry that can be used to help implement or perform the disclosed technique or method. In FIG. 18, the system 1800 can include or be coupled to a stimulation electrode grid 1810, such as for transcutaneously delivering high frequency electrical nerve stimulation, e.g., to an external location superficial to the peroneal nerve of the patient. Stimulation delivery can be controlled by stimulation controller circuitry 1814, such as a microcontroller, FPGA, or other suitable circuitry. The stimulation controller circuitry 1814 can also provide one or more control signals to a stimulation electrode selector/multiplexer circuitry 1812, such as can select a particular combination of stimulation electrodes from the stimulation electrode grid 1810, for delivering the electrical nerve stimulations to the patient. Recording electrodes 1802 can receive the responsive surface EMG signal, which can be routed through an isolation and bandpass or other filtering circuitry 1804 and, in turn, to an amplifier 1806. The surface EMG signal response can be digitized and further signal processed by a processor circuit 1808, and communicated to a local or remote user device via a wireless communication unit 1816. A battery 1818 and power management circuitry 1820 can also be provided.

In an illustrative example, the surface EMG signal from the tibialis anterior can be detected, such as via the two or more recording electrodes. The acquired surface EMG signal can be first filtered (e.g., by the isolation and filtering circuit) and amplified (e.g., by the amplifier), before being digitized and signal-processed or analyzed by the on-board processor circuitry. The processor can also control the electrostimulation controller circuitry, such as can be configured to produce a constant-current or other output programmed to provide one or more electrical nerve stimulation therapy settings chosen by the processor. A multiplexor can then be used to select the programmed pair of electrodes, such as from a grid of available electrodes. The processor may also include transmitter or transceiver circuitry, such as can be configured to communicate wirelessly (e.g. via Bluetooth or WiFi) or otherwise to an external display or processing unit (e.g., such as computer or smartphone) such as for further processing or displaying the results of parameter optimization or information associated with electrical nerve stimulation.

An application on the patient or caregiver's smartphone can be provided, such as to help guide the user through a step-wise sequence to help identify or determine which electrical nerve stimulation waveform and electrode locations are most effective for that particular patient.

Example Using sEMG Response to Neurostimulation Together with Muscle Activation

In an example, the sEMG-based personalization of NPNS described above can involve measuring sEMG during delivery of NPNS during a controlled protocol that involves a stereotyped muscular activation. The stereotyped muscular activation may be voluntary or involuntary. The controlled protocol can involves one or more muscles associated with the neural or neuromuscular targets of NPNS (or the antagonistic muscles thereof). This approach can include measuring a stereotyped sEMG response associated with the muscular activation. The system can be used to measure the extent to which this sEMG response is modulated via NPNS relative to baseline (no NPNS), where such modulation of sEMG response can be either an increase in sEMG signal amplitude, a decrease in sEMG signal amplitude, or a change in duration of an sEMG response signal artifact. Some illustrative examples are described below.

EXAMPLE 1

Voluntary Phasic Flexion

In this approach, the patient or subject can be instructed to repeatedly perform a controlled movement. For example, the subject can be instructed to perform this specified movement multiple times at baseline (without delivering NPNS) and during evaluation of each parameter setting of the NPNS being tested to reduce variability. The sEMG response can be measured on a muscle associated with the specified movement (or an antagonistic muscle thereto). Parameters of the specified movement, including effort and time interval between each movement instance, can be selected such that fatigue is minimal, such that movement-evoked sEMG activity stays relatively constant over time in the absence of delivery of NPNS. NPNS can be applied in a blocked experimental design and the sEMG activity during NPNS-ON blocks can be compared to sEMG activity during NPNS-OFF blocks.

More particularly, the subject can be instructed to dorsiflex the subject's foot towards the subject's knee. NPNS can be applied over the subject's peroneal nerve and sEMG can be measured over the subject's tibialis anterior muscle. For example, the subject can be instructed to flex toes towards knee (dorsiflexion) with consistent timing and force, such as in sets of 6 repetitions with less than 1-second rest between repetitions and approximately 10-seconds rest between sets. This elicits a sEMG signal in the tibialis anterior during the time of the dorsiflexion, the amplitude of which is stable at baseline (during NPNS-OFF). This sEMG signal in the tibialis anterior can be smoothed (e.g., using a low-pass filter) and rectified, and the maximum sEMG amplitude for each dorsiflexion can be recorded as a single point.

Figure 19:
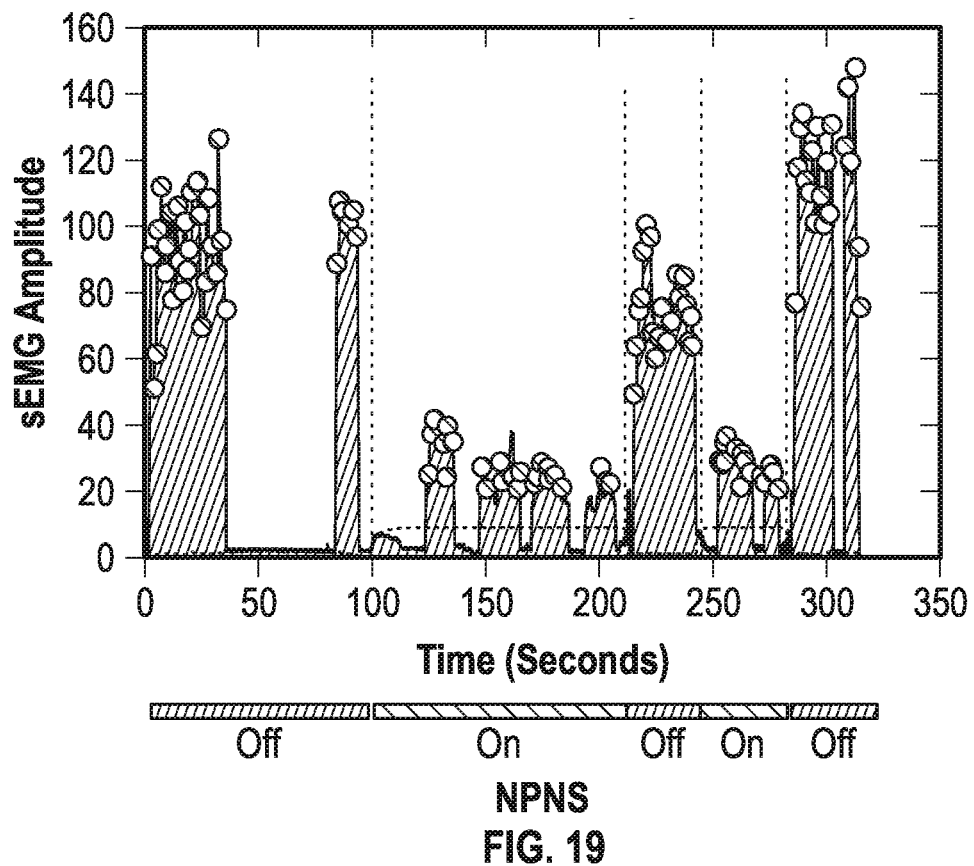
FIGS. 19, 20, and 21 represent experimental data comparing sEMG data during muscle activation for NPNS ON compared to NPNS OFF.
Figure 20:
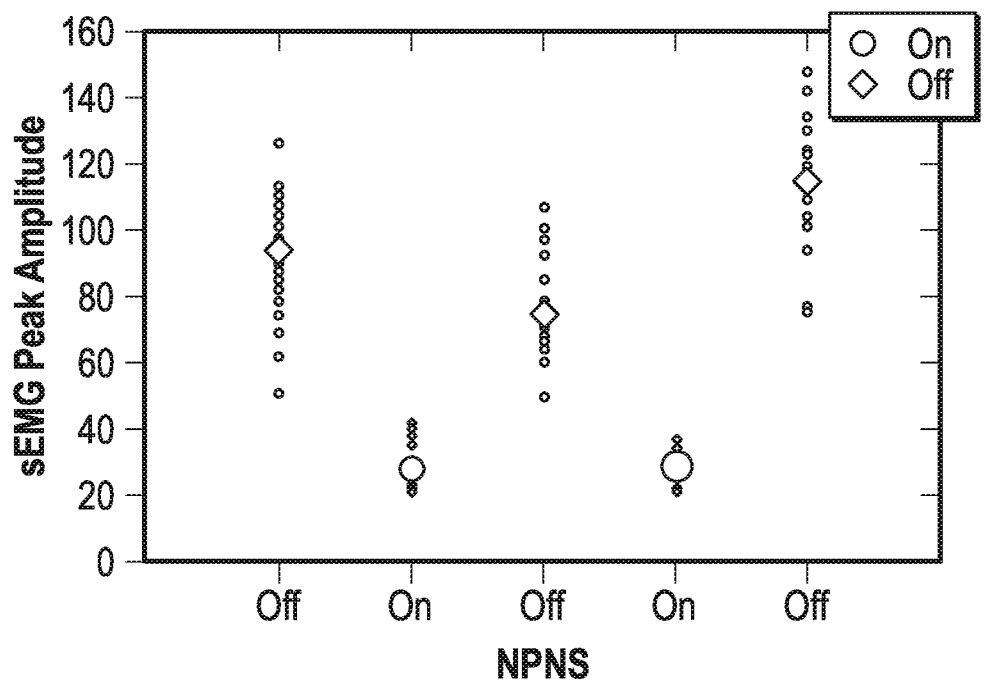
Figure 21:
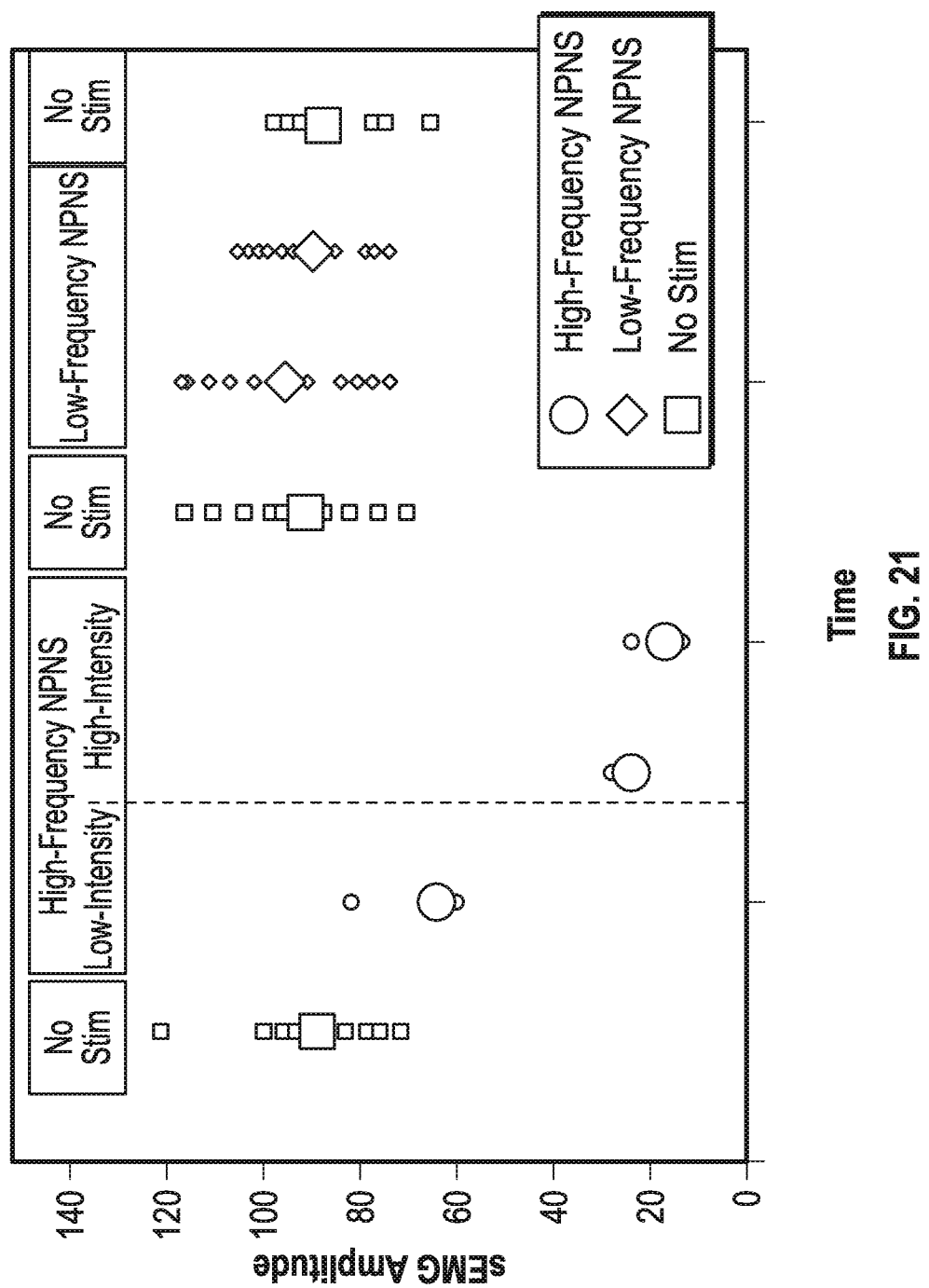

FIGS. 19-21 represent experimental data that was obtained using such an approach. This EMG peak amplitude was compared for interleaved blocks of dorsiflexions with NPNS ON compared to NPNS OFF. As illustrated in the data shown in FIGS. 19-21, in this example, NPNS reduced the sEMG amplitude in the tibialis anterior.

FIG. 19 is a graph of experimental data of sEMG amplitude vs. time for time periods when NPNS was either on or off. FIG. 19 shows such sEMG activity in tibialis anterior during repetitive foot dorsiflexions. Rectified smoothed sEMG traces shown in FIG. 19 and peak sEMG activity for each dorsiflexion is annotated by a circle.

FIG. 20 is a peak sEMG amplitude vs. NPNS status graph of the same experimental data shown in FIG. 19, showing the peak sEMG activity for each dorsiflexion from FIG. 19. In FIG. 20, it is seen that the peak sEMG amplitude during dorsiflexion decreases during periods of NPNS.

FIG. 21 is a graph of experimental data of peak sEMG amplitude for various stimulation conditions and parameters during foot dorsiflexions (e.g., no stimulation, high-frequency and low intensity stimulation, high-frequency and high intensity simulation, no stimulation, low-frequency stimulation, no stimulation). Thus, FIG. 21 shows peak sEMG activity for foot dorsiflexions during adjustment of stimulation parameters, including high-frequency (4000 Hz) and lower-frequency (<500 Hz). In FIG. 21, it is seen that sEMG amplitude during dorsiflexion and high-frequency NPNS is modulated (decreased) in a manner that depends on the high-frequency NPNS intensity, but that this behavior does not occur for lower-frequency stimulation or for no-stimulation. It is believed that the amount of such sEMG amplitude modulation (decrease) during dorsiflexion (or other controlled muscular activation) and high-frequency NPNS can be used as an indicator of neurostimulation responsivity of a particular patient or neurostimulation efficacy, such as for evaluating and comparing different NPNS parameter settings.

EXAMPLE 2

Involuntary Phasic Reflex

In this approach, the patient or subject can be instructed to relax their muscles. A muscular reflex can be repeatedly induced by applying phasic electrical stimulation to sensory fibers associated with a muscle spindle (e.g., Hoffman's reflex) or by applying phasic force to a muscle spindle such as to induce a stretch reflex (e.g., patellar reflex). The surface EMG (sEMG) signal can be measured on a muscle associated with the reflex (or an antagonistic muscle thereto). The parameters of reflex induction, including amplitude and time interval between each reflex instance, can be selected such that fatigue is minimal, and thus reflex-evoked sEMG activity stays relatively constant over time in the absence of NPNS. NPNS can be applied, such as in a blocked experimental design, and the sEMG activity during NPNS-ON blocks can be compared to sEMG activity during NPNS-OFF blocks.

EXAMPLE 3

Voluntary Isometric Flexion

In this approach, the patient or subject can be instructed to tonically activate muscle via isometric flexion. For example, this can include tonically activating muscle by pushing against a fixed object or pulling a rope attached to a fixed object. Surface EMG (sEMG) can be measured on a muscle associated with the isometric flexion (or an antagonistic muscle thereto). Effort and duration of protocol can be selected such that fatigue is minimal, and thus sEMG activity stays relatively constant over time in the absence of NPNS. NPNS can be applied in a blocked experimental design and the sEMG activity during NPNS-ON blocks can be compared to sEMG activity during NPNS-OFF blocks.

In the various Examples 1-3, the system can include an electrostimulation unit with a response signal measurement unit and controller circuitry to measure a signal that is related to muscle activation, such as one or more of the following physiological signals:

a. EMG activity of the muscle, such as can be measured by sEMG or invasive EMG;

b. Force, such as can be measured by a dynamometer or other means; or c. Movement, such as can be measured by one or more of an IMU, accelerometer, gyroscope, or video, or the like.

Whereas at rest therapeutic NPNS is associated with an increase in tonic sEMG activity, during these controlled protocols, therapeutic NPNS may result in a decrease, an increase, or a modulation of the protocol-evoked sEMG activity. In these examples, the NPNS-based differences in this physiological signal may be used to predict the strength of therapeutic responses to various NPNS parameter combinations (personalization/optimization) and/or the response of a various patient to NPNS (patient selection).

Figure 22:
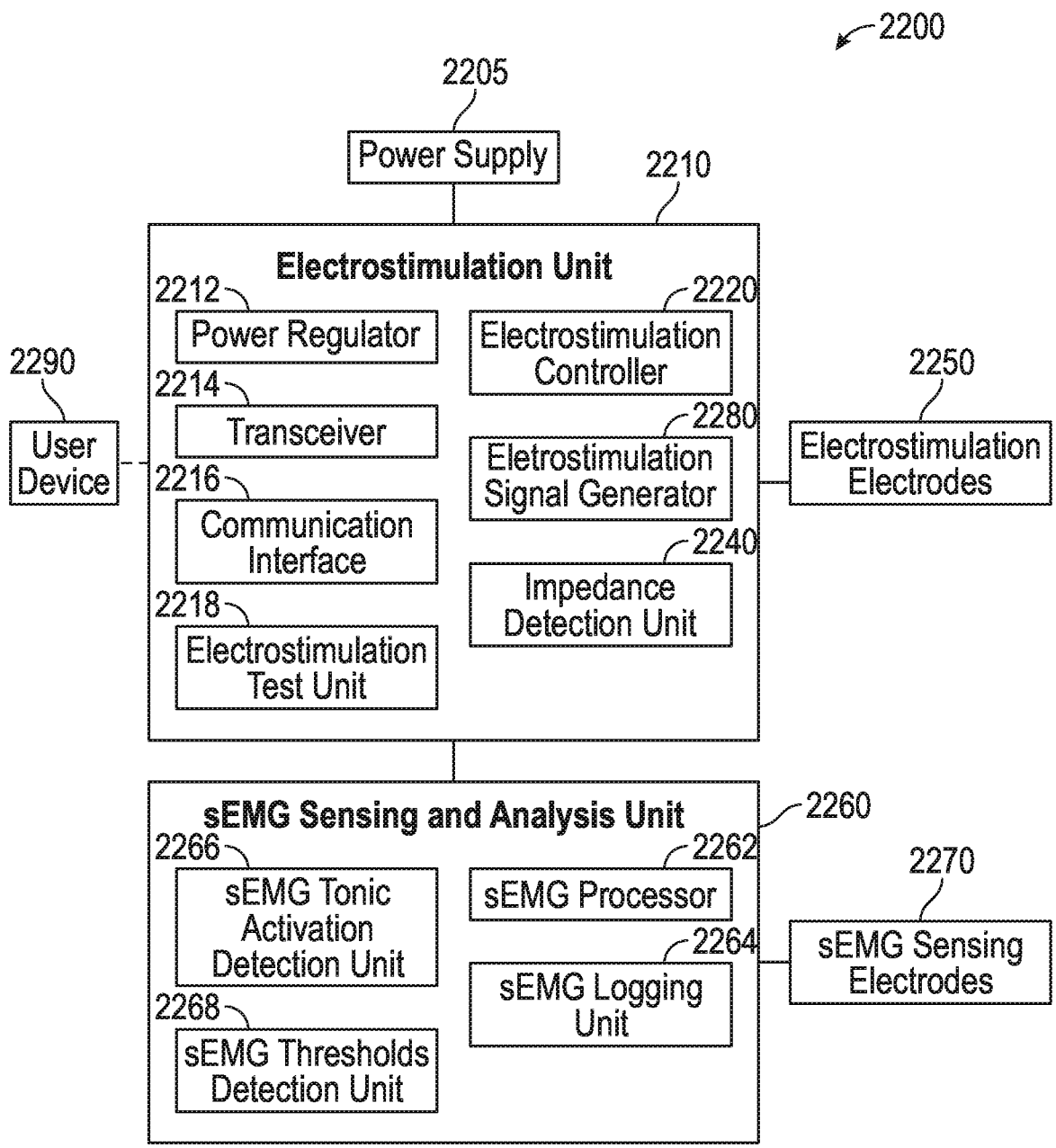
FIG. 22 shows an example of portions of the present system, such as can be used to perform one or more of the techniques described herein.

FIG. 22 shows an example of portions of the present system 2200, such as can be used to perform one or more of the techniques described herein. The system 2200 can include an electrostimulation unit 2210. The electrostimulation unit 2210 can include or be coupled to electrostimulation electrodes 2250, such as can be placed on or affixed to an external location of the subject of delivering the high-frequency NPNS, such as described herein. The electrostimulation unit 2210 can include or be coupled to a power supply 2205, such as for providing electrical energy from which the NPNS can be delivered, including to various circuitry used for generating the NPNS or to controller circuitry for executing one or more algorithms or for performing signal processing. The electrostimulation unit 2210 can include or be coupled to power regulator circuitry 2212, configured for receiving energy from the power supply 2205 and regulating power for delivery to other circuitry included in or coupled to the electrostimulation control unit 2210. An electrostimulation generator 2230 can be configured for generating the high-frequency NPNS electrostimulation pulses, such as described herein, for delivery to the subject via the electrostimulation electrodes 2250. An electrostimulation controller 2220 circuit can control timing, electrostimulation parameters (e.g., amplitude, frequency, pulsewidth, duty cycle, electrode selection, etc.) of the NPNS electrostimulations generated by the electrostimulation generator 2230. The electrostimulation unit 2210 can include impedance detection circuitry 2240, such as can be configured for detecting a load impedance or an electrode-skin interface impedance at one or more of the electrostimulation electrodes 2250, and such impedance information can be provided to the electrostimulation controller, such as for electrostimulation parameter selection or adjustment or control algorithm parameter selection or adjustment, which can be based in part upon such detected impedance, e.g., automatically or in a closed-loop fashion. The electrostimulation unit 2210 can include an electrostimulation test unit 2218, such as can include circuitry configured for controlling testing of patient responsivity to NPNS or to compare NPNS efficacy at various electrostimulation parameter settings, such as for selecting a particular setting of a combination of electrostimulation parameters, such as based on responsivity or efficacy determinations, such as described herein. The electrostimulation unit 2210 can include one or both of a communication interface 2216 circuitry or a transceiver 2214 circuitry, such as to permit wired or wireless communication with a local or remote user interface device 2290, such as for use by the patient or other subject to provide feedback about a particular NPNS instance or episode, such as for determining pain or discomfort threshold, distraction threshold, or other patient feedback or patient input information.

The electrostimulation unit 2210 can include or be coupled to an sEMG sensing and analysis unit 2260 circuitry, such as can be implemented on microprocess, microcontroller, or controller circuitry that can be included in or coupled to the electrostimulation unit 2210. The sEMG sensing and analysis unit 2260 can be coupled to sEMG sensing electrodes 2270, such as can be affixed to a muscle innervated by a target nerve of the NPNS (or an antagonistic muscle thereto), such as described elsewhere herein. The sEMG sensing and analysis unit 2260 can include an sEMG tonic activation detection unit 2266, such as can include buffer amplifier, integration or other sEMG signal filtering or analog or digital signal processing circuitry, analog-to-digital conversion circuitry, peak amplitude detection circuitry, comparator circuitry, or other appropriate circuitry for performing the sEMG tonic activation detection techniques described herein. An sEMG threshold detection unit 2268 can include circuitry configured for determining tonic muscle activation threshold, pain threshold, discomfort threshold, distraction threshold, or the like, such as described herein. An sEMG processor 162 can include controller circuitry or signal processing circuitry, such as for performing encoded instructions for determining sEMG signal amplitudes, peak values, durations, patient thresholds, or the like, such as described herein. An sEMG logging unit 2264 can include memory circuitry and other circuitry, such as for storing sEMG responses to various NPNS instances, such as NPNS instances provided under different parameter settings or different electrode selections, such as for comparison to determine an optimum or other desired NPNS parameter setting or electrode selection, or to switch between different parameter settings or electrode selections, such as to improve efficacy, save power, or to achieve one or more other goals.

RECAP AND FURTHER DESCRIPTION OF VARIOUS ASPECTS OF THE PRESENT DISCLOSURE

The followed numbered list of aspects is intended to highlight, without limitation or without imposing a requirement, various aspects of the present disclosure, such as can be used individually or in combination to provide one or more of a system, a method, a device-readable medium for performing a method, or an article of manufacture, according to the present disclosure.

Aspect 1 can include a system, device, apparatus, method, device-readable medium, article of manufacture, or the like such as can include or use (or can be combined with one or more other Aspects to include or use a system for treating a patient having one or more symptoms associated with at least one of Restless Legs Syndrome (RLS) or Periodic Limb Movement Disorder (PLMD) using applied high-frequency electrostimulation. This aspect can include or use at least one electrostimulation electrode, such as can be configured for location at a first external target body location near a peroneal nerve or a branch thereof. This aspect can also include or use an external, non-implantable electrostimulation unit such as can be coupled to the at least one electrostimulation electrode such as for generating and applying to the peroneal nerve or branch thereof a first high-frequency pulsed electrostimulation signal, such as can include a frequency in a range of 500 Hz to 15,000 Hz, such as producing tonic sEMG activity or modulating phasic sEMG activity in at least one muscle innervated by the peroneal nerve.

Aspect 2 can include or use, or can be combined with the subject matter of Aspect 1 to include or use, at least one parameter setting of the first high-frequency pulsed electrostimulation signal being specified, based at least in part on an observed surface electromyographic (sEMG) signal.

Aspect 3 can include or use, or can be combined with the subject matter of Aspect 1 or 2 to include or use at least one parameter setting of first high-frequency pulsed electrostimulation signal being capable of being specified, based at least in part on patient feedback, to be less than at least one of a pain threshold or a distraction threshold. For example, this can be based on a subjective determination by the patient, which can be provided by the patient to the system via a user interface device, such as described herein.

Aspect 4 can include or use, or can be combined with the subject matter of any of Aspects 1 through 3 to include or use the at least one parameter setting of the first high-frequency pulsed electrostimulation signal being capable of being configured to permit being specified differently based on a time-of-day or other indication of whether the patient is, or is expected to be, one of awake or asleep. For example, this can include a clock or a sleep detector or other modality that can be used by the system to provide a higher level of NPNS during daytime/awake (e.g., permitting distraction but not discomfort) than the level of NPNS provided during nighttime/asleep.

Aspect 5 can include or use, or can be combined with the subject matter of any of Aspects 1 through 4 to include or use the observed sEMG signal being from at least one muscle innervated by the peroneal nerve of the same patient to which the first high-frequency pulsed electrostimulation signal is delivered. For example, this can permit patient specific tailoring or personalization of NPNS such as to meet or balance between one or more goals, e.g., efficacy, power savings, etc. Alternatively, population-based or similar subpopulation based tailoring or personalization of NPNS can be implemented using techniques of the present disclosure.

Aspect 6 can include or use, or can be combined with the subject matter of any of Aspects 1 through 5 to include or use the electrostimulation unit including or being coupled to controller circuitry such as can be configured to determine whether, or a degree to which (e.g., sEMG signal amplitude), the first high-frequency pulsed electrostimulation signal produces tonic sEMG activity in an observed sEMG signal from the same patient. For example, this information can be used to determine patient responsivity to NPNS, efficacy of NPNS, or to compare various parameter settings to select an appropriate parameter setting of NPNS, such as based on one or more goals. For example, peak amplitude of the sEMG signal can be used, with the muscle either at rest, or using controlled muscle activations, such as described elsewhere herein.

Aspect 7 can include or use, or can be combined with the subject matter of any of Aspects 1 through 6 to include or use the electrostimulation unit including or being coupled to controller circuitry that can be configured to store one or more indications of sEMG activity such as respectively corresponding to different settings of the at least one parameter of the first high-frequency pulsed electrostimulation signal. For example, this information can be used to compare efficacy of various NPNS settings, which can be used by itself or together with other information to meet or balance between one or more goals (e.g., efficacy, power consumption, etc.)

Aspect 8 can include or use, or can be combined with the subject matter of any of Aspects 1 through 7 to include or use the electrostimulation unit including or being coupled to controller circuitry that can be configured to select the at least one parameter setting of the first high-frequency pulsed electrostimulation signal such as can be based on a comparison of corresponding sEMG activity at different settings.

Aspect 9 can include or use, or can be combined with the subject matter of any of Aspects 1 through 8 to include or use the electrostimulation unit including or being coupled to controller circuitry that can be configured to record an indication of baseline sEMG activity obtained without providing the first high-frequency pulsed electrostimulation signal to the patient.

Aspect 10 can include or use, or can be combined with the subject matter of any of Aspects 1 through 9 to include or use the controller circuitry being configured to characterize a neurostimulation responsiveness of the patient such as can be based at least in part on a change in observed sEMG activity in the patient from the baseline sEMG activity, in response to the first high-frequency pulsed electrostimulation signal.

Aspect 11 can include or use, or can be combined with the subject matter of any of Aspects 1 through 10 to include or use the controller circuit being configured to characterize the neurostimulation responsiveness based at least in part on at least one of a tonic motor activation threshold, a distraction threshold, or a pain threshold, determined using one or more parameter settings of the first high-frequency pulsed electrostimulation signal. For example, the tonic motor activation threshold can be determined using the sEMG signal, and the distraction and pain thresholds can be determined using subjective patient feedback, such as via a user interface device that can be provided to the patient.

Aspect 12 can include or use, or can be combined with the subject matter of any of Aspects 1 through 11 to include or use the electrostimulation unit including, or being coupled to controller circuitry that can include or can be coupled to, a communication interface such as for receiving a patient feedback or other input from a user such as for use in one or more of selecting or determining the first high-frequency pulsed electrostimulation signal or a parameter thereof.

Aspect 13 can include or use, or can be combined with the subject matter of any of Aspects 1 through 12 to include or use at least one sEMG signal electrode such as can be configured to be located or locatable in association with at least one muscle innervated by the peroneal nerve of the same patient to which the first high-frequency pulsed electrostimulation signal is delivered by the at least one electrostimulation electrode.

Aspect 14 can include or use, or can be combined with the subject matter of any of Aspects 1 through 13 to include or use the at least one electrostimulation electrode being locatable at a first external target body location near a peroneal nerve or a branch thereof comprises: at least one first electrostimulation electrode configured for location at a first external target body location on a right leg of the patient near a right peroneal nerve or a branch thereof; and at least one second electrostimulation electrode configured for location at a second external target body location on a left leg of the patient near a left peroneal nerve or a branch thereof. The electrostimulation unit can be configured to generate the first high-frequency pulsed electrostimulation signal for delivery to the right peroneal nerve or branch thereof using the at least one first electrostimulation electrode to produce or modulate tonic surface electromyographic (sEMG) activity in at least one muscle innervated by the right peroneal nerve and to generate a second high-frequency pulsed electrostimulation signal for delivery to the left peroneal nerve or branch thereof using the at least one second electrostimulation electrode to produce or modulate tonic surface electromyographic (sEMG) activity in at least one muscle innervated by the left peroneal nerve. For example, this can be used to provide bilateral stimulation, bilateral sEMG monitoring, or both.

Aspect 15 can include or use, or can be combined with the subject matter of any of Aspects 1 through 14 to include or use the electrostimulation unit being configured to repeatedly deliver pulses of the first high-frequency pulsed electrostimulation signal, such as in a ramped manner of increasing energy levels, such as toward a target energy level.

Aspect 16 can include or use, or can be combined with the subject matter of any of Aspects 1 through 15 to include or use an arrangement of a plurality of electrodes, wherein the electrostimulation unit can include or can be coupled to controller circuitry that can be configured to select one or more electrodes from the plurality of electrodes such as based at least in part on observed sEMG activity in response to a test electrostimulation signal delivered to the patient such as via different ones of the plurality of electrodes, and to use the selected one or more electrodes such as to apply a therapeutic electrostimulation signal to the patient.

Aspect 17 can include or use, or can be combined with the subject matter of any of Aspects 1 through 16 to include or use the electrostimulation unit including or being coupled to controller circuitry configured such as for specifying at least one parameter setting of the first high-frequency pulsed electrostimulation signal, such as based at least in part on a modulation of phasic sEMG activity in an observed sEMG signal such as together with muscle activation of the at least one muscle innervated by the peroneal nerve. For example, this can include controlled muscle activation such as the dorsiflexion or other techniques described herein.

Aspect 18 can include or use, or can be combined with the subject matter of any of Aspects 1 through 17 to include or use the electrostimulation unit being coupled to the at least one electrostimulation electrode such as for both delivering the first high-frequency pulsed electrostimulation signal to the patient and for detecting a responsive sEMG signal from the patient using the same at least one electrostimulation electrode. Alternatively, different electrodes can be used for sEMG sensing than those used for NPNS or other electrostimulation.

Aspect 19 can include or use, or can be combined with the subject matter of any of Aspects 1 through 18 to include or use a method of treating a patient having one or more symptoms associated with at least one of Restless Legs Syndrome (RLS) and Periodic Limb Movement Disorder (PLMD) using applied high-frequency electrostimulation. The method can include delivering, to a first external target body location near a peroneal nerve or a branch thereof, a first high-frequency pulsed electrostimulation signal defined by a plurality of parameters, including a frequency in a range of 500 Hz to 15,000 Hz. The method can also include producing tonic sEMG activity or modulating phasic sEMG activity in at least one muscle innervated by the peroneal nerve. The method can further optionally include establishing or adjusting at least one parameter setting of the first high-frequency pulsed electrostimulation signal based at least in part on an observed surface electromyographic (sEMG) signal.

Aspect 20 can include or use, or can be combined with the subject matter of any of Aspects 1 through 19 to include or use the at least one parameter setting of first high-frequency pulsed electrostimulation signal being capable of being specified, based at least in part on patient feedback, such as to be less than at least one of a pain threshold or a distraction threshold.

Aspect 21 can include or use, or can be combined with the subject matter of any of Aspects 1 through 20 to include or use the at least one parameter setting of the first high-frequency pulsed electrostimulation signal capable of being differently specifiable such as based on a time-of-day or other indication of whether the patient is, or is expected to be, one of awake or asleep.

Aspect 22 can include or use, or can be combined with the subject matter of any of Aspects 1 through 21 to include or use the observed sEMG signal being from at least one muscle innervated by the peroneal nerve of the same patient to which the first high-frequency pulsed electrostimulation signal is delivered.

Aspect 23 can include or use, or can be combined with the subject matter of any of Aspects 1 through 22 to include or use selecting the at least one parameter setting of the first high-frequency pulsed electrostimulation signal such as based on a comparison of sEMG activity produced in response to a plurality of different high-frequency pulsed electrostimulation test signals (e.g., at different settings, such as of one or more neurostimulation parameters).

Aspect 24 can include or use, or can be combined with the subject matter of any of Aspects 1 through 23 to include or use characterizing a neurostimulation responsiveness of the patient such as can be based at least in part on a change in observed sEMG activity in the patient from baseline sEMG activity, such as in response to the first high-frequency pulsed electrostimulation signal.

Aspect 25 can include or use, or can be combined with the subject matter of any of Aspects 1 through 24 to include or use characterizing the neurostimulation responsiveness of the patient such as can be based at least in part on at least one of a tonic motor activation threshold, a distraction threshold, or a pain threshold, such as can be determined using a plurality of different high-frequency pulsed electrostimulation test signals (e.g., corresponding to differences in one or more parameter settings of the first high-frequency pulsed electrostimulation signal).

Aspect 26 can include or use, or can be combined with the subject matter of any of Aspects 1 through 25 to include or use bilaterally electrostimulating both legs of the patient.

Aspect 27 can include or use, or can be combined with the subject matter of any of Aspects 1 through 26 to include or use selecting, from an arrangement of a plurality of electrodes, one or more electrodes such as can be based at least in part on observed sEMG activity in response to a test electrostimulation signal delivered to the patient via different ones of the plurality of electrodes, and using the selected one or more electrodes to apply a therapeutic electrostimulation signal to the patient.

Aspect 28 can include or use, or can be combined with the subject matter of any of Aspects 1 through 27 to include or use specifying the at least one parameter setting of the first high-frequency pulsed electrostimulation signal, such as can be based at least in part on a modulation of tonic sEMG activity in the observed sEMG signal such as together with muscle activation of the at least one muscle innervated by the peroneal nerve.

Aspect 29 can include or use, or can be combined with the subject matter of any of Aspects 1 through 28 to include or use a system for treating a patient having one or more symptoms associated with at least one of Restless Legs Syndrome (RLS) and Periodic Limb Movement Disorder (PLMD) using applied high-frequency electrostimulation. The system can include: at least one electrostimulation electrode configured for location at a first external target body location near a peroneal nerve or a branch thereof; and an external, non-implantable electrostimulation unit coupled to the at least one electrostimulation electrode for generating and applying to the peroneal nerve or branch thereof a first high-frequency pulsed electrostimulation signal, including a frequency in a range of 500 Hz to 15,000 Hz, wherein the electrostimulation unit includes or is coupled to controller circuitry configured to specify at least one parameter setting of the first high-frequency pulsed electrostimulation signal (1) based at least in part on a responsive observed surface electromyographic (sEMG) signal in the same patient, such as for producing tonic sEMG activity or modulating phasic sEMG activity in at least one muscle innervated by the peroneal nerve, and (2) based at least in part on patient feedback, to be less than at least one of a pain threshold or a distraction threshold, wherein the controller circuitry is configured to select the at least one parameter setting of the first high-frequency pulsed electrostimulation signal based on a comparison of corresponding sEMG activity at different settings; and at least one sEMG signal electrode locatable in association with at least one muscle innervated by the peroneal nerve of the same patient to which the first high-frequency pulsed electrostimulation signal is delivered by the at least one electrostimulation electrode.

Aspect 30 can include or use, or can be combined with the subject matter of any of Aspects 1 through 29 to include or use a method of characterizing a neurostimulation responsiveness of a patient having one or more symptoms associated with at least one of Restless Legs Syndrome (RLS) and Periodic Limb Movement Disorder (PLMD) using applied high-frequency electrostimulation. The method can include delivering, to a first external target body location near a peroneal nerve or a branch thereof, a first high-frequency pulsed electrostimulation signal, including a frequency in a range of 500 Hz to 15,000 Hz, such as for producing or modulating tonic sEMG activity in at least one muscle innervated by the peroneal nerve. The method can also include characterizing a neurostimulation responsiveness of the patient based at least in part on (1) a change in observed sEMG activity in the patient from baseline sEMG activity, in response to the delivered first high-frequency pulsed electrostimulation signal, and (2) at least one of a tonic motor activation threshold, a distraction threshold, or a pain threshold, determined using one or more parameter settings of the first high-frequency pulsed electrostimulation signal.

Aspect 31 can include or use, or can be combined with the subject matter of any of Aspects 1 through 30 to include or use a method of using applied high-frequency stimulation for treating a patient having one or more symptoms associated with at least one of Restless Legs Syndrome (RLS) or Periodic Limb Movement Disorder (PLMD). The method can include locating at least one electrostimulation electrode at a first external location on the body of the patient associated with at least one nerve selected from a peroneal nerve or a branch thereof, a sural nerve or a branch thereof, or a femoral nerve or a branch thereof, of a patient. The method can also include delivering an electrostimulation signal to the first external location for reducing or alleviating one or more symptoms associated with RLS or PLMD, wherein the electrostimulation signal comprises a pulsed electrical signal characterized by a plurality of parameters including a pulse frequency that is between 500 Hz and 15,000 Hz, inclusive, wherein the electrostimulation signal is capable of producing at least one of, or both of: (1) tonic sEMG activation in a muscle innervated by the at least one nerve; or (2) suppression of muscular excitability of the patient during voluntary muscle activation, such as dorsiflexion.

Aspect 32 can include or use, or can be combined with the subject matter of any of Aspects 1 through 31 to include or use a method of treating a patient having one or more symptoms associated with at least one of Restless Legs Syndrome (RLS) and Periodic Limb Movement Disorder (PLMD) using applied high-frequency electrostimulation. The method can include: coupling at least one first electrostimulation electrode to at least a first external target body location of the patient proximate to a peroneal nerve or a branch thereof; and delivering a first high-frequency pulsed electrostimulation therapy signal to the at least a first external target body location using the at least one first electrostimulation electrode. The pulses of the electrostimulation therapy signal can be defined by a plurality of parameters including at least a frequency of between 500 and 15,000 Hz, and a current of between 5 and 100 mA, and wherein the electrostimulation therapy signal is above a tonic motor threshold of at least one muscle innervated by the peroneal nerve or a branch thereof, and below a pain threshold.

Aspect 33 can include or use, or can be combined with the subject matter of any of Aspects 1 through 32 to include or use the electrostimulation therapy signal being below at least one of a tolerability threshold and a distraction threshold.

Aspect 34 can include or use, or can be combined with the subject matter of any of Aspects 1 through 33 to include or use the distraction threshold being a threshold of the maximum stimulation at which a patient is not distracted from falling asleep during a sleep period.

Aspect 35 can include or use, or can be combined with the subject matter of any of Aspects 1 through 34 to include or use the pulses configured to not produce phasic muscle activity in the at least one muscle innervated by the peroneal nerve or a branch thereof.

Aspect 36 can include or use, or can be combined with the subject matter of any of Aspects 1 through 35 to include or use delivering the first high-frequency pulsed electrostimulation therapy signal comprising applying charge-balanced AC controlled-current pulses to the at least a first external target body location, and controlling or adjusting the current such as can be based on a measured load impedance or component thereof.

Aspect 37 can include or use, or can be combined with the subject matter of any of Aspects 1 through 36 to include or use locating at least one EMG sensing electrode on the skin of the patient proximate to said at least one muscle innervated by peroneal nerve or a branch thereof; delivering an electrostimulation test signal to the at least one first electrostimulation electrode, wherein the pulses of the electrostimulation therapy are defined by a plurality of parameters including at least a frequency of between 500 and 10,000 Hz, and a current of between 0 and 50 mA; sensing EMG activity of the at least one muscle innervated by the at least one of a sural nerve and a peroneal nerve evoked by the electrostimulation test signal; determining whether or not the electrostimulation test signal is above the tonic motor threshold and below the pain threshold; repeating the steps of delivering an electrostimulation test signal, sensing EMG activity and determining whether or not the electrostimulation test signal is above the tonic motor threshold and below the pain threshold, wherein the pulses of the electrostimulation therapy for each repetition of delivering an electrostimulation test signal have at least one of a different frequency and a different current than an immediately preceding electrostimulation test signal; and selecting one of the electrostimulation test signals as the first high-frequency pulsed electrostimulation therapy signal.

Aspect 38 can include or use, or can be combined with the subject matter of any of Aspects 1 through 37 to include or use delivering an electrostimulation test signal can include delivering an electrostimulation test signal having a first current value, and wherein each repeated step of delivering an electrostimulation test signal can include applying an electrostimulation signal having a current higher than the current of the immediately preceding electrostimulation test signal.

Aspect 39 can include or use, or can be combined with the subject matter of any of Aspects 1 through 38 to include or use the repeated steps of delivering an electrostimulation test signal comprise applying a series in electrostimulation test signals for which the current value of the test signals increased at a rate of from 1 mA/0.25 seconds to 1 mA/15 seconds.

Aspect 40 can include or use, or can be combined with the subject matter of any of Aspects 1 through 39 to include or use the at least one muscle innervated by the peroneal nerve or a branch thereof comprises at least one of the tibialis anterior, the extensor digitorum longus, the peroneus tertius, the extensor hallucis longus, the fibularis longus, and the fibularis brevis.

Aspect 41 can include or use, or can be combined with the subject matter of any of Aspects 1 through 40 to include or use monitoring at least one body parameter selected from a body movement, a cardiac parameter, a respiratory parameter, and a neurological parameter; determining whether the patient is in a sleep state or a waking state; if the patient is in a sleep state: processing the at least one body parameter; and adjusting the electrostimulation therapy signal if the body parameter is indicative of one of arousal or a likelihood of impending arousal if the patient is asleep.

Aspect 42 can include or use, or can be combined with the subject matter of any of Aspects 1 through 41 to include or use coupling at least one first electrostimulation electrode to at least a first external target body location comprising: coupling at least one first electrostimulation electrode to a first external target body location on a left leg of the patient proximate to a left peroneal nerve or a branch thereof; and coupling at least one second electrostimulation electrode to a second external target body location on a right leg of the patient proximate to a right peroneal nerve or a branch thereof; and wherein delivering a first high-frequency pulsed electrostimulation therapy signal comprises delivering a first electrostimulation therapy signal having a frequency of between 500 and 15,000 Hz and a current of between 5 and 100 mA to a left peroneal nerve or a branch thereof using the at least one first electrostimulation electrode, the first electrostimulation therapy signal inducing tonic activation in at least one muscle innervated by the left peroneal nerve or a branch thereof and being below a pain threshold, the method further comprising: delivering a second high-frequency pulsed electrostimulation therapy signal having a frequency of between 500 and 15,000 Hz and a current of between 5 and 100 mA to a right peroneal nerve or a branch thereof using the at least one second electrostimulation electrode, the second electrostimulation therapy signal inducing tonic activation in at least one muscle innervated by the right peroneal nerve or a branch thereof and being below a pain threshold.

Aspect 43 can include or use, or can be combined with the subject matter of any of Aspects 1 through 42 to include or use coupling at least one first electrostimulation electrode to at least a first external target body location comprising coupling at least one first electrostimulation electrode to a first external target body location on a leg of the patient proximate to a peroneal nerve or a branch thereof, and wherein delivering a first high-frequency pulsed electrostimulation therapy signal comprises delivering a first electrostimulation therapy signal having a frequency of between 500 and 15,000 Hz and a current of between 5 and 100 mA to a peroneal nerve or branch thereof using the at least one first electrostimulation electrode, the first electrostimulation therapy signal inducing tonic activation in at least one muscle innervated by the peroneal nerve or a branch thereof and being below a pain threshold, the method further comprising: coupling at least one second electrostimulation electrode to at least a second external target body location on an arm of the patient proximate to one of an ulnar nerve or a branch thereof and a radial nerve or a branch thereof; and delivering a second high-frequency pulsed electrostimulation therapy signal having a frequency of between 500 and 15,000 Hz and a current of between 5 and 100 mA to one of an ulnar nerve or a branch thereof and a radial nerve or a branch thereof using the at least one second electrostimulation electrode, the second electrostimulation therapy signal inducing tonic activation in at least one muscle innervated by the one of an ulnar nerve or a branch thereof and a radial nerve or a branch thereof, and being below a pain threshold.

Aspect 44 can include or use, or can be combined with the subject matter of any of Aspects 1 through 43 to include or use the first external target location is a skin surface superficial to a peroneal nerve or a branch thereof.

Aspect 45 can include or use, or can be combined with the subject matter of any of Aspects 1 through 44 to include or use the sleep period is the time between bedtime and the intended wake-up time of the patient.

Aspect 46 can include or use, or can be combined with the subject matter of any of Aspects 1 through 45 to include or use the at least one first stimulation electrode is positioned such that the proximal edge overlaps the head of the fibula over the superficial peroneal nerve.

Aspect 47 can include or use, or can be combined with the subject matter of any of Aspects 1 through 46 to include or use at least a second electrode being positioned medially of the at least one first electrode with about one-half inch separation distance from the first electrode, the at least a second electrode overlapping the distal region of the tibialis anterior muscle.

Aspect 48 can include or use, or can be combined with the subject matter of any of Aspects 1 through 47 to include or use a method of determining stimulation parameters for a noninvasive peripheral neurostimulation therapy comprising: coupling at least one first electrostimulation electrode to a first external target body location of the patient proximate to a peroneal nerve or a branch thereof; coupling at least one first EMG sensing electrode to the skin of the patient proximate to a muscle innervated by the peroneal nerve or a branch thereof; delivering a high-frequency pulsed electrostimulation test signal to the peroneal nerve or a branch thereof, wherein the pulses of the electrostimulation test signal are defined by a plurality of parameters including at least a frequency of between 500 and 15,000 Hz, and a current of between 0 and 100 mA; sensing EMG activity of the muscle innervated by the peroneal nerve or a branch thereof in response to the electrostimulation test signal; determining whether or not the electrostimulation test signal is above the tonic motor threshold of the muscle and below the pain threshold of the patient based on the sensed EMG activity; repeating the steps of delivering a high-frequency pulsed electrostimulation test signal to the peroneal nerve or a branch thereof, sensing EMG activity of the muscle, and determining whether or not the electrostimulation test signal is above the tonic motor threshold and below the pain threshold, wherein the pulses of the electrostimulation therapy for each repetition of delivering an electrostimulation test signal have at least one of a different frequency and a different current than an immediately preceding electrostimulation test signal; and selecting one of the electrostimulation test signals that is above the tonic motor threshold and below the pain threshold as a high-frequency pulsed electrostimulation therapy signal.

Aspect 49 can include or use, or can be combined with the subject matter of any of Aspects 1 through 48 to include or use: for each step of delivering a high-frequency pulsed electrostimulation test signal, determining whether or not the electrostimulation test signal is at or near a distraction threshold; selecting one of the high-frequency pulsed electrostimulation test signals that is above the tonic motor threshold, at below a distraction threshold, and below a pain threshold as a high-frequency pulsed electrostimulation therapy signal; and applying the selected high-frequency pulsed electrostimulation test signal to the first external target body location as a high-frequency pulsed electrostimulation therapy signal for a first time period.

Aspect 50 can include or use, or can be combined with the subject matter of any of Aspects 1 through 49 to include or use a method of determining one or more patient thresholds for a noninvasive peripheral neurostimulation therapy comprising: coupling at least one first electrostimulation electrode to a first external target body location of the patient proximate to a peroneal nerve or a branch thereof; coupling at least one first EMG sensing electrode to the skin of the patient proximate to a muscle innervated by the peroneal nerve or a branch thereof; delivering a high-frequency pulsed electrostimulation test signal to the peroneal nerve or a branch thereof, wherein the pulses of the electrostimulation test signal are defined by a plurality of parameters including at least a frequency of between 500 and 15,000 Hz, and a current of between 0 and 100 mA; sensing EMG activity of the muscle innervated by the peroneal nerve or a branch thereof in response to the electrostimulation test signal; determining whether or not the electrostimulation test signal is above the tonic motor threshold of the muscle and below the pain threshold of the patient based on the sensed EMG activity; determining whether or not the electrostimulation test signal is above one or more of a sensory threshold, a distraction threshold, a tolerability threshold, or a pain threshold based on patient feedback; repeating the steps of delivering a high-frequency pulsed electrostimulation test signal to the peroneal nerve or a branch thereof, sensing EMG activity of the muscle, determining whether or not the electrostimulation test signal is above the tonic motor threshold and below the pain threshold, and determining whether or not the electrostimulation test signal is above one or more of a sensory threshold, a distraction threshold, a tolerability threshold, and a pain threshold based on patient feedback, wherein the pulses of the electrostimulation therapy for each repetition of delivering an electrostimulation test signal have at least one of a different frequency and a different current than an immediately preceding electrostimulation test signal; identifying a tonic motor threshold and at least one of a sensor threshold, a distraction threshold, a tolerability threshold, and a pain threshold; and performing a further action selected from: logging the identified thresholds; selecting one of the high-frequency pulsed electrostimulation test signals for application to the peroneal nerve or a branch thereof; and identifying a change in one of the identified thresholds from a previously-determined threshold.

Aspect 51 can include or use, or can be combined with the subject matter of any of Aspects 1 through 50 to include or use delivering a high-frequency pulsed electrostimulation test signal comprises delivering an electrostimulation test signal having a first current value, and wherein each repeated step of delivering an electrostimulation test signal comprises applying an electrostimulation signal having a current higher than the current of the immediately preceding electrostimulation test signal.

Aspect 52 can include or use, or can be combined with the subject matter of any of Aspects 1 through 51 to include or use the repeated steps of delivering an electrostimulation test signal comprise applying a series in electrostimulation test signals for which the current value of the test signals increased at a rate of from 1 mA/0.25 seconds to 1 mA/15 seconds.

Aspect 53 can include or use, or can be combined with the subject matter of any of Aspects 1 through 52 to include or use a system for treating a patient having one or more symptoms associated with at least one of Restless Legs Syndrome (RLS) and Periodic Limb Movement Disorder (PLMD) using applied high-frequency electrostimulation. The system can include: at least one electrostimulation electrode located at a first external target body location near a peroneal nerve or a branch thereof; an external electrostimulation unit coupled to the at least one electrostimulation electrode comprising: an electrostimulation signal generator that generates a first high-frequency pulsed electrostimulation therapy signal having a frequency of from 500 and 15,000 Hz and a current of at least 5 mA and applies the first, high-frequency electrostimulation therapy signal to the peroneal nerve or branch thereof using the at least one electrostimulation electrode to produce tonic surface electromyographic (sEMG) activity in at least one muscle innervated by the peroneal nerve.

Aspect 54 can include or use, or can be combined with the subject matter of any of Aspects 1 through 53 to include or use wherein the first high-frequency pulsed electrostimulation therapy signal produces tonic sEMG activity in the at least one muscle innervated by the peroneal nerve during the application of the first high-frequency pulsed electrostimulation therapy signal that exceeds the baseline sEMG activity in the at least one muscle in the absence of the first high-frequency pulsed electrostimulation therapy by a specified magnitude selected from at least 50%, at least 100%, and at least 200% for a specified time period selected from at least 5 seconds, at least 10 seconds, at least 15 seconds, and at least 30 seconds.

Aspect 55 can include or use, or can be combined with the subject matter of any of Aspects 1 through 54 to include or use the first high-frequency pulsed electrostimulation therapy signal is defined by a plurality of parameters including at least a frequency of from 500 Hz to 10,000 Hz.

Aspect 56 can include or use, or can be combined with the subject matter of any of Aspects 1 through 55 to include or use the first high-frequency pulsed electrostimulation therapy signal includes a current magnitude of from 5-50 mA.

Aspect 57 can include or use, or can be combined with the subject matter of any of Aspects 1 through 56 to include or use the at least one muscle innervated by the peroneal nerve or a branch thereof comprises at least one of the tibialis anterior, the extensor digitorum longus, the peroneus tertius, the extensor hallucis longus, the fibularis longus, and the fibularis brevis.

Aspect 58 can include or use, or can be combined with the subject matter of any of Aspects 1 through 57 to include or use the external electrostimulation unit further comprising: at least one surface EMG (sEMG) electrode coupled to a second external target body location near the at least one muscle innervated by the peroneal nerve or a branch thereof, wherein the at least one surface EMG recording electrode senses sEMG activity in the at least one muscle and generates an sEMG signal indicative of the sensed sEMG activity in the at least one muscle; and an sEMG processor that receives the sEMG signal from the at least one sEMG electrode and analyzes the sEMG signal received during or within 500 milliseconds of the termination of the application of the first high-frequency electrostimulation signal to the at least one muscle to determine whether the first high-frequency pulsed electrostimulation signal produces tonic sEMG activity in the at least one muscle innervated by the peroneal nerve.

Aspect 59 can include or use, or can be combined with the subject matter of any of Aspects 1 through 58 to include or use an electrostimulation test unit that causes the external electrostimulation signal unit to generate a plurality of electrostimulation test signals having a frequency of from 500 and 15,000 Hz and a current of at least 5 mA and to sequentially apply each of the plurality of electrostimulation test signals to the peroneal nerve or branch thereof using the at least one electrostimulation electrode; and an sEMG tonic activation detection unit that causes the sEMG processor to receive an sEMG signal from the at least one sEMG electrode during the application of each of the plurality of electrostimulation test signals to the peroneal nerve or branch thereof, to analyze the sEMG signal received during the application of the each of the plurality of electrostimulation test signals to the peroneal nerve or branch thereof, to determine whether each electrostimulation test signal produces tonic sEMG activity in the at least one muscle innervated by the peroneal nerve, and to determine the magnitude of any such tonic sEMG activity produced by each electrostimulation test signal; and at least one of a logging unit for storing whether each electrostimulation test signal in the plurality of electrostimulation test signals produces tonic sEMG activity in the at least one muscle, and for storing the magnitude of any such tonic sEMG activity; and a transceiver unit for transmitting to a user whether each electrostimulation test signal in the plurality of electrostimulation test signals produces tonic sEMG activity in the at least one muscle.

Aspect 60 can include or use, or can be combined with the subject matter of any of Aspects 1 through 59 to include or use each electrostimulation test signal after the first electrostimulation test signal comprising a higher current than the current of the immediately preceding electrostimulation test signal.

Aspect 61 can include or use, or can be combined with the subject matter of any of Aspects 1 through 60 to include or use a communication interface for receiving an input from a user selecting one of the plurality of electrostimulation test signals as the first high-frequency pulsed electrostimulation therapy signal.

Aspect 62 can include or use, or can be combined with the subject matter of any of Aspects 1 through 60 to include or use each of the plurality of electrostimulation test signals is applied to the peroneal nerve or a branch thereof while the leg of the patient is in a condition selected from one of unmoving, performing a voluntary dorsiflexion, or performing an involuntary reflex.

Aspect 63 can include or use, or can be combined with the subject matter of any of Aspects 1 through 62 to include or use the at least one electrostimulation electrode located at a first external target body location near a peroneal nerve or a branch thereof comprises: at least one first electrostimulation electrode located at a first external target body location on a right leg of the patient near a right peroneal nerve or a branch thereof; and at least one second electrostimulation electrode located at a second external target body location on a left leg of the patient near a left peroneal nerve or a branch thereof, and wherein the electrostimulation signal generator generates a first high-frequency pulsed electrostimulation therapy signal having a frequency of from 500 and 15,000 Hz and a current of at least 5 mA and applies the first, high-frequency electrostimulation therapy signal to the right peroneal nerve or branch thereof using the at least one first electrostimulation electrode to produce tonic surface electromyographic (sEMG) activity in at least one muscle innervated by the right peroneal nerve; and generates a second high-frequency pulsed electrostimulation therapy signal having a frequency of from 500 and 15,000 Hz and a current of at least 5 mA and applies the second, high-frequency electrostimulation therapy signal to the left peroneal nerve or branch thereof using the at least one second electrostimulation electrode to produce tonic surface electromyographic (sEMG) activity in at least one muscle innervated by the left peroneal nerve.

Aspect 64 can include or use, or can be combined with the subject matter of any of Aspects 1 through 63 to include or use a system for treating a patient having one or more symptoms associated with at least one of Restless Legs Syndrome (RLS) and Periodic Limb Movement Disorder (PLMD) using applied high-frequency electrostimulation. The system can comprise: at least one electrostimulation electrode located at a first external target body location near a peroneal nerve or a branch thereof; at least one surface EMG (sEMG) electrode coupled to a second external target body location near at least one muscle innervated by the peroneal nerve or a branch thereof, wherein the at least one surface EMG recording electrode senses sEMG activity in the at least one muscle and generates an sEMG signal indicative of the sensed sEMG activity in the at least one muscle; an external electrostimulation unit coupled to the at least one electrostimulation electrode comprising an electrostimulation signal generator that generates a first high-frequency pulsed electrostimulation therapy signal having a frequency of from 500 and 15,000 Hz and a current of at least 5 mA and applies the first, high-frequency electrostimulation therapy signal to the peroneal nerve or branch thereof using the at least one electrostimulation electrode to produce tonic surface electromyographic (sEMG) activity in at least one muscle innervated by the peroneal nerve; an electrostimulation test unit that causes the external electrostimulation signal unit to generate a plurality of electrostimulation test signals having a frequency of from 500 and 15,000 Hz and a current of at least 5 mA and to sequentially apply each of the plurality of electrostimulation test signals to the peroneal nerve or branch thereof using the at least one electrostimulation electrode; a user device to receive an input indicative of the patient's perception of each of the plurality of electrostimulation test signals relating to at least one of pain, tolerability, and distraction of the patient from falling asleep during a sleep period; an sEMG threshold detection unit that receives, for each of the plurality of electrostimulation test signals: 1) the sEMG signal from the at least one sEMG electrode, and 2) the input indicative of the patient's perception from the user device; and analyzes the sEMG signal and the input indicative of the patient's perception, and determines one or more of a tonic motor threshold, a pain threshold, a tolerability threshold, and a distraction threshold based on the sEMG signals and the inputs indicative of the patient's perception; and at least one of a logging unit for storing whether each electrostimulation test signal in the plurality of electrostimulation test signals produces tonic sEMG activity in the at least one muscle, and for storing the magnitude of any such tonic sEMG activity; and a transceiver unit for transmitting to the user device user the at least one of a tonic motor threshold, a pain threshold, a tolerability threshold, and a distraction threshold.

Other Embodiments

The present techniques may also be used for optimizing or personalizing other nerve stimulation technique that stimulates a nerve that innervates a muscle, including vagus nerve stimulators for epilepsy (pharyngeal muscles) and spinal nerve stimulators for chronic pain.

The detailed description set forth above in connection with the appended drawings is intended as a description of various configurations and is not intended to represent the only configurations in which the concepts described herein can be practiced. The detailed description includes specific details for the purpose of providing a thorough understanding of various concepts. However, it will be apparent to those skilled in the art that these concepts can be practiced without these specific details. In some instances, well-known structures and components are shown in block diagram form in order to avoid obscuring such concepts.

Examples of systems and methods for systems and methods for identifying, assessing, and treating patients having hyperexcited or hyperactive nerves are presented with reference to various electronic devices and methods, which are described in the following detailed description and illustrated in the accompanying drawing by various blocks, components, circuits, steps, processes, algorithms, etc. (collectively referred to as "elements"). These elements can be implemented using electronic hardware, computer software, firmware, or other form of executable computer code, or any combination thereof. Whether such elements are implemented as hardware or software depends upon the particular application and design constraints imposed on the overall system.

By way of example, an element, or any portion of an element, or any combination of elements of various electronic systems can be implemented using one or more processors. Examples of processors include microprocessors, microcontrollers, graphics processing units (GPUs), central processing units (CPUs), application processors, digital signal processors (DSPs), reduced instruction set computing (RISC) processors, systems on a chip (SoC), baseband processors, field programmable gate arrays (FPGAs), programmable logic devices (PLDs), state machines, gated logic, discrete hardware circuits, and other suitable hardware configured to perform the various functionalities described throughout this disclosure. One or more processors in the processing system can execute software. Software shall be construed broadly to mean instructions, instruction sets, code, code segments, program code, programs, subprograms, software components, applications, software applications, software packages, routines, subroutines, objects, executables, threads of execution, procedures, functions, etc., whether referred to as software, firmware, middleware, microcode, hardware description language, or otherwise.

Accordingly, in one or more examples, the functions described for certain methods and systems for treating patients having hyperexcited or hyperactive nerves can be implemented in hardware, software, or any combination thereof. If implemented in software, the functions can be stored on or encoded as one or more instructions or code on a computer-readable medium. Computer-readable media can include transitory or non-transitory computer storage media for carrying or having computer-executable instructions or data structures stored thereon. Both transitory and non-transitory storage media can be any available media that can be accessed by a computer as part of the processing system. By way of example, and not limitation, such computer-readable media can include a random-access memory (RAM), a read-only memory (ROM), an electrically erasable programmable ROM (EEPROM), optical disk storage, magnetic disk storage, other magnetic storage devices, combinations of the aforementioned types of computer-readable media, or any other medium that can be used to store computer-executable code in the form of instructions or data structures accessible by a computer. Further, when information is transferred or provided over a network or another communications connection (either hardwired, wireless, or combination thereof) to a computer, the computer or processing system properly determines the connection as a transitory or non-transitory computer-readable medium, depending on the particular medium. Thus, any such connection is properly termed a computer-readable medium. Combinations of the above should also be included within the scope of the computer-readable media. Non-transitory computer-readable media exclude signals per se and the air interface.

What is claimed is:

1. A system for treating a patient having one or more symptoms associated with at least one of Restless Legs Syndrome (RLS) and Periodic Limb Movement Disorder (PLMD) using applied high-frequency electrostimulation, the system comprising:
   at least one electrostimulation electrode configured for location at a first external target body location on a leg near a target nerve or a branch thereof; and
   a wearable external, non-implantable electrostimulation unit coupled to the at least one electrostimulation electrode for generating and applying to the target nerve or branch thereof a first high-frequency electrostimulation signal, having a frequency within a range of 2 kilohertz (kHz) and 6 kHz and controlled such that, when the at least one electrostimulation electrode is in place over the head of a patient fibula, signal induces tonic motor activation of a tibialis anterior muscle in response to a specified current intensity within a range of 15 milliamps (mA) and 40 mA; and
   onboard power management circuitry coupled to the electrostimulation unit for powering the electrostimulation unit via a battery.

2. The system of claim 1, wherein the electrostimulation unit is configured for generating and applying the first high-frequency electrostimulation signal to produce tonic sEMG activity in response to the electrostimulation signal.

3. The system of claim 1, wherein the electrostimulation unit is configured for generating and applying the first high-frequency electrostimulation signal to modulate phasic sEMG activity in response to the electrostimulation signal.

4. The system of claim 1, wherein at least one parameter setting of the first high-frequency electrostimulation signal is specified for treating the at least one of RLS or PLMD, based at least in part on an observed surface electromyographic (sEMG) signal.

5. The system of claim 1, wherein at least one parameter setting of first high-frequency electrostimulation signal is specified for treating the at least one of RLS or PLMD, based at least in part on patient feedback, to be less than at least one of a pain threshold or a distraction threshold.

6. The system of claim 1, wherein at least one parameter setting of the first high-frequency electrostimulation signal is configured for treating the at least one of RLS or PLMD to permit being specified differently based on a time-of-day or other indication of whether the patient is, or is expected to be, one of awake or asleep.

7. The system of claim 1, wherein the electrostimulation unit includes or is coupled to controller circuitry configured to determine whether, or a degree to which, the first high-frequency electrostimulation signal produces tonic sEMG activity in an observed sEMG signal from the same patient for providing an indicator of efficacy of electrostimulation treatment of at least one of RLS or PLMD.

8. The system of claim 1, wherein the electrostimulation unit includes or is coupled to controller circuitry that is configured to store indications of sEMG activity respectively corresponding to different settings of at least one parameter of the first high-frequency electrostimulation signal for treating at least one of RLS or PLMD.

9. The system of claim 1, wherein the electrostimulation unit includes or is coupled to controller circuitry that is configured to select at least one parameter setting for treating at least one of RLS or PLMD of the first high-frequency electrostimulation signal based on a comparison of sEMG activity at different settings.

10. The system of claim 9, wherein the controller circuitry is configured to characterize a neurostimulation responsiveness for treating at least one of RLS or PLMD based at least in part on at least one of a tonic motor activation threshold, a distraction threshold, or a pain threshold, determined using one or more parameter settings of the first high-frequency electrostimulation signal.

11. The system of claim 1, wherein the electrostimulation unit includes or is coupled to controller circuitry that is configured to record an indication of baseline sEMG activity obtained without providing the first high-frequency electrostimulation signal to the patient.

12. The system of claim 11, wherein the controller circuitry is configured to characterize a neurostimulation responsiveness for treating at least one of RLS or PLMD of the patient based at least in part on a change in observed sEMG activity in the patient from the baseline sEMG activity, in response to the first high-frequency electrostimulation signal.

13. The system of claim 1, further comprising at least one sEMG signal electrode configured to be located in association with at least one muscle innervated by the target nerve of the same patient to which the first high-frequency electrostimulation signal is delivered by the at least one electrostimulation electrode for treating at least one of RLS or PLMD.

14. The system of claim 1, wherein the at least one electrostimulation electrode locatable at a first external target body location on a leg near a target nerve or a branch thereof comprises:

at least one first electrostimulation electrode configured for location at a first external target body location on a right leg of the patient near a right target nerve or a branch thereof; and at least one second electrostimulation electrode configured for location at a second external target body location on a left leg of the patient near a left target nerve or a branch thereof;

wherein the electrostimulation unit generates the first high-frequency electrostimulation signal for delivery to the right target nerve or branch thereof for treating at least one of RLS or PLMD using the at least one first electrostimulation electrode to produce or modulate tonic surface electromyographic (sEMG) activity in at least one muscle innervated by the right target nerve and generates a second high-frequency pulsed electrostimulation signal for delivery to the left target nerve or branch thereof using the at least one second electrostimulation electrode to produce or modulate tonic surface electromyographic (sEMG) activity in at least one muscle innervated by the left target nerve.

15. The system of claim 1, wherein the electrostimulation unit is configured to repeatedly deliver pulses of the first high-frequency electrostimulation signal for treating at least one of RLS or PLMD in a ramped manner of increasing energy levels toward a target energy level.

16. The system of claim 1, comprising an arrangement of a plurality of electrodes, wherein the electrostimulation unit includes or is coupled to controller circuitry that is configured to select one or more electrodes from the plurality of electrodes based at least in part on observed sEMG activity indicative of at least one of RLS or PLMD treatment efficacy in response to a test electrostimulation signal delivered to the patient via different ones of the plurality of electrodes, and use the selected one or more electrodes to apply a therapeutic electrostimulation signal to the patient.

17. The system of claim 1, wherein the electrostimulation unit includes or is coupled to controller circuitry configured for specifying at least one parameter setting of the first high-frequency electrostimulation signal for treating at least one of RLS or PLMD, based at least in part on a modulation of phasic sEMG activity in an observed sEMG signal together with muscle activation of the at least one muscle innervated by the target nerve.

18. The system of claim 1, wherein the electrostimulation unit is coupled to the at least one electrostimulation electrode for both delivering the first high-frequency pulsed electrostimulation signal to the patient for treating at least one of RLS or PLMD and for detecting a responsive sEMG signal from the patient, for indicating efficacy of treating at least one of RLS or PLMD, using the same at least one electrostimulation electrode.

19. A system for treating a patient having one or more symptoms associated with at least one of Restless Legs Syndrome (RLS) and Periodic Limb Movement Disorder (PLMD) using applied high-frequency electrostimulation, the system comprising:

at least one electrostimulation electrode configured for location at a first external target body location on a leg near a target nerve or a branch thereof; and an external, non-implantable electrostimulation unit coupled to the at least one electrostimulation electrode for generating and applying to the target nerve or branch thereof a first high-frequency electrostimulation signal, having a frequency within a range of 2 kHz to 6 kHz at a substantially 100% duty cycle during a specified electrostimulation period for producing tonic sEMG activity in at least one muscle innervated by a peroneal nerve of the patient and using at least one observed sEMG signal as an indicator of efficacy of electrostimulation treatment of the at least one of RLS or PLMD.

20. The system of claim 19, wherein the electrostimulation unit is configured to generate and apply the first high-frequency electrostimulation signal for modulating phasic sEMG activity, including reducing or minimizing phasic sEMG activity.

21. A system for treating a patient having one or more symptoms associated with at least one of Restless Legs Syndrome (RLS) and Periodic Limb Movement Disorder (PLMD) using applied high-frequency electrostimulation, the system comprising:
- at least one electrostimulation electrode configured for location at a first external target body location on a leg near a target nerve or a branch thereof; and
- a wearable external, non-implantable electrostimulation unit coupled to the at least one electrostimulation electrode for generating and applying to the target nerve or branch thereof a first high-frequency electrostimulation signal, having signal parameters including a frequency of about 4000 hertz (Hz), a pulse width of about 125 microseconds (μs), and a maximum current amplitude between 15 milliamps (mA) and 40 mA, thereby establishing a root means squared (RMS) current greater than 15 mA; and
- onboard power management circuitry coupled to the electrostimulation unit for powering the electrostimulation unit via a battery.

22. The system of claim 21, wherein the electrostimulation unit comprises controller circuitry to establish or adjust at least one parameter signal parameter of the electrostimulation signal to produce tonic motor activation of a tibialis anterior muscle.

\* \* \* \* \*